(12) United States Patent
Mitelberg et al.

(10) Patent No.: US 12,171,425 B2
(45) Date of Patent: Dec. 24, 2024

(54) ENDOSCOPIC NEEDLE ASSEMBLY

(71) Applicant: BOSTON SCIENTIFIC SCIMED, INC., Maple Grove, MN (US)

(72) Inventors: Vladimir Mitelberg, Austin, TX (US); Andrew Gant, Austin, TX (US); Donald K. Jones, Dripping Springs, TX (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/473,831

(22) Filed: Sep. 25, 2023

(65) Prior Publication Data

US 2024/0008870 A1    Jan. 11, 2024

Related U.S. Application Data

(63) Continuation of application No. 16/456,692, filed on Jun. 28, 2019, now Pat. No. 11,812,951, which is a
(Continued)

(51) Int. Cl.
*A61B 17/062*    (2006.01)
*A61B 1/00*    (2006.01)
(Continued)

(52) U.S. Cl.
CPC ...... *A61B 17/0625* (2013.01); *A61B 1/00087* (2013.01); *A61B 1/00089* (2013.01);
(Continued)

(58) Field of Classification Search
CPC .......... A61B 17/00234; A61B 17/0401; A61B 17/0469; A61B 17/0482; A61B 17/0483;
(Continued)

(56) References Cited

U.S. PATENT DOCUMENTS 2,023,807 A    12/1935 Gruss et al.
3,495,703 A    2/1970 Calabrese
(Continued)

FOREIGN PATENT DOCUMENTS

WO    2008069816 A1    6/2008

OTHER PUBLICATIONS

U.S. Appl. No. 61/483,679, filed May 8, 2011, Vladimir Mitelberg.
(Continued)

*Primary Examiner* — Robert A Lynch
(74) *Attorney, Agent, or Firm* — Seager, Tufte & Wickhem, LLP

(57) ABSTRACT

An anchor and suture assembly is provided for use with an endoscopic suturing device with a needle holder arm. The anchor assembly includes an anchor tip and an anchor body. The anchor tip has a blunt end that may be rounded or beaded, a capture groove, a tab groove and a plug portion positioned between the capture groove and the tab groove. The anchor body has first and second ends, tip tabs, retainers for removably retaining the anchor body relative to the needle holder arm, and a suture opening. The anchor tip is fixed relative to the anchor body by plastic deformation of the tip tabs into the tab groove. A suture extends into the suture opening of the anchor body and is fixed therein.

20 Claims, 76 Drawing Sheets

Related U.S. Application Data continuation-in-part of application No. 14/924,087, filed on Oct. 27, 2015, now Pat. No. 11,534,160, which is a continuation of application No. 13/328,003, filed on Dec. 16, 2011, now Pat. No. 9,198,562, which is a continuation-in-part of application No. 12/485,576, filed on Jun. 16, 2009, now Pat. No. 8,287,556.

(60) Provisional application No. 61/495,970, filed on Jun. 11, 2011, provisional application No. 61/483,679, filed on May 8, 2011, provisional application No. 61/162,249, filed on Mar. 20, 2009, provisional application No. 61/073,340, filed on Jun. 17, 2008.

(51) Int. Cl.
  A61B 1/018 (2006.01)
  A61B 17/00 (2006.01)
  A61B 17/04 (2006.01)
  A61B 17/06 (2006.01)
  A61B 17/064 (2006.01)
  A61B 17/068 (2006.01)
  A61B 17/29 (2006.01)

(52) U.S. Cl.
  CPC ...... *A61B 1/00101* (2013.01); *A61B 1/00137* (2013.01); *A61B 1/018* (2013.01); *A61B 17/0401* (2013.01); *A61B 17/0487* (2013.01); *A61B 17/06123* (2013.01); *A61B 17/06133* (2013.01); *A61B 17/068* (2013.01); *A61B 17/00234* (2013.01); *A61B 2017/00296* (2013.01); *A61B 2017/00349* (2013.01); *A61B 2017/0042* (2013.01); *A61B 2017/00477* (2013.01); *A61B 2017/0409* (2013.01); *A61B 2017/0414* (2013.01); *A61B 2017/0417* (2013.01); *A61B 2017/0446* (2013.01); *A61B 2017/0448* (2013.01); *A61B 2017/045* (2013.01); *A61B 2017/0451* (2013.01); *A61B 2017/0454* (2013.01); *A61B 2017/0464* (2013.01); *A61B 2017/0496* (2013.01); *A61B 2017/06047* (2013.01); *A61B 2017/06052* (2013.01); *A61B 2017/0608* (2013.01); *A61B 2017/0649* (2013.01); *A61B 2017/2912* (2013.01)

(58) Field of Classification Search
  CPC .......... A61B 17/0487; A61B 17/06123; A61B 17/06133; A61B 17/0625; A61B 17/068; A61B 2017/00296; A61B 2017/00349; A61B 2017/0042; A61B 2017/00477; A61B 2017/0409; A61B 2017/0414; A61B 2017/0417; A61B 2017/0446; A61B 2017/0448; A61B 2017/045; A61B 2017/0451; A61B 2017/0454; A61B 2017/0464; A61B 2017/0496; A61B 2017/06047; A61B 2017/06052; A61B 2017/0608; A61B 2017/0649; A61B 2017/2912; A61B 1/00087; A61B 1/00089; A61B 1/00101; A61B 1/00137; A61B 1/018
  See application file for complete search history.

(56) References Cited

U.S. PATENT DOCUMENTS

| | | |
|---|---|---|
| 3,592,196 A | 7/1971 | Daikhovsky et al. |
| 3,603,492 A | 9/1971 | Schantz |
| 3,749,328 A | 7/1973 | Dusenbery |
| 3,901,244 A | 8/1975 | Schweizer |
| 4,084,692 A | 4/1978 | Bilweis |
| 4,183,431 A | 1/1980 | Schmidt et al. |
| D263,505 S | 3/1982 | Black |
| 4,575,548 A | 3/1986 | Ueda et al. |
| 4,794,911 A | 1/1989 | Okada |
| 4,805,292 A | 2/1989 | Noguchi |
| 5,026,379 A | 6/1991 | Yoon |
| 5,041,129 A | 8/1991 | Hayhurst et al. |
| 5,116,358 A | 5/1992 | Granger |
| 5,131,534 A | 7/1992 | Brown et al. |
| 5,141,520 A | 8/1992 | Goble et al. |
| 5,196,022 A | 3/1993 | Bilweis |
| 5,217,486 A | 6/1993 | Rice et al. |
| 5,249,671 A | 10/1993 | Sinn |
| 5,263,585 A | 11/1993 | Lawhon et al. |
| 5,284,240 A | 2/1994 | Alpern et al. |
| 5,304,185 A | 4/1994 | Taylor |
| 5,307,924 A | 5/1994 | Manosalva et al. |
| 5,356,424 A | 10/1994 | Buzerak et al. |
| 5,364,408 A | 11/1994 | Gordon |
| 5,389,103 A * | 2/1995 | Melzer ............... A61B 17/0469 606/147 |
| 5,403,328 A | 4/1995 | Shallman |
| 5,407,071 A | 4/1995 | Lawhon et al. |
| 5,433,725 A | 7/1995 | Christian et al. |
| 5,437,266 A | 8/1995 | McPherson et al. |
| 5,437,680 A | 8/1995 | Yoon |
| 5,454,823 A | 10/1995 | Richardson et al. |
| 5,464,424 A | 11/1995 | O'Donnell, Jr. |
| 5,466,241 A | 11/1995 | Leroy et al. |
| 5,470,338 A | 11/1995 | Whitfield et al. |
| 5,474,568 A | 12/1995 | Scott |
| 5,478,344 A | 12/1995 | Stone et al. |
| 5,478,345 A | 12/1995 | Stone et al. |
| 5,514,159 A | 5/1996 | Matula et al. |
| 5,520,702 A | 5/1996 | Sauer et al. |
| 5,527,321 A | 6/1996 | Hinchliffe |
| 5,545,180 A | 8/1996 | Le et al. |
| 5,569,301 A | 10/1996 | Granger et al. |
| 5,573,496 A | 11/1996 | McPerson et al. |
| 5,575,800 A | 11/1996 | Gordon |
| 5,578,044 A | 11/1996 | Gordon et al. |
| 5,584,860 A | 12/1996 | Goble et al. |
| 5,584,861 A | 12/1996 | Swain et al. |
| 5,601,557 A | 2/1997 | Hayhurst |
| 5,626,590 A | 5/1997 | Wilk |
| 5,626,614 A | 5/1997 | Hart |
| 5,628,395 A | 5/1997 | Daniele et al. |
| 5,643,320 A | 7/1997 | Lower et al. |
| 5,649,940 A | 7/1997 | Hart et al. |
| 5,653,717 A | 8/1997 | Ko et al. |
| 5,662,588 A | 9/1997 | Tida |
| 5,662,658 A | 9/1997 | Wenstrom, Jr. |
| 5,669,917 A | 9/1997 | Sauer et al. |
| 5,681,331 A | 10/1997 | De La Torre et al. |
| 5,685,823 A | 11/1997 | Ito et al. |
| 5,690,655 A | 11/1997 | Hart et al. |
| 5,700,272 A | 12/1997 | Gordon et al. |
| 5,707,379 A | 1/1998 | Fleenor et al. |
| 5,713,910 A | 2/1998 | Gordon et al. |
| 5,720,766 A | 2/1998 | Zang et al. |
| 5,730,747 A | 3/1998 | Ek et al. |
| 5,733,293 A | 3/1998 | Scirica et al. |
| 5,741,277 A | 4/1998 | Gordon et al. |
| 5,755,729 A | 5/1998 | De La Torre et al. |
| 5,765,740 A | 6/1998 | Ferguson |
| 5,782,862 A | 7/1998 | Bonutti |
| 5,792,152 A | 8/1998 | Klein et al. |
| 5,792,153 A * | 8/1998 | Swain ................ A61B 17/0469 606/139 |
| 5,810,848 A | 9/1998 | Hayhurst |
| 5,814,054 A | 9/1998 | Kortenbach et al. |
| 5,814,071 A | 9/1998 | McDevitt et al. |
| 5,817,013 A | 10/1998 | Ginn et al. |
| 5,819,918 A | 10/1998 | Scanlon |
| 5,824,009 A | 10/1998 | Fukuda et al. |
| 5,833,055 A | 11/1998 | Cerwin et al. |

(56) References Cited

U.S. PATENT DOCUMENTS

| | | |
|---|---|---|
| 5,843,099 A | 12/1998 | Nichols et al. |
| 5,860,992 A | 1/1999 | Daniel et al. |
| 5,879,371 A | 3/1999 | Gardiner et al. |
| 5,887,594 A | 3/1999 | Locicero, III |
| 5,891,160 A | 4/1999 | Williamson, IV et al. |
| 5,897,563 A | 4/1999 | Yoon et al. |
| 5,897,564 A | 4/1999 | Schulze et al. |
| 5,908,428 A | 6/1999 | Scirica et al. |
| 5,910,105 A | 6/1999 | Swain et al. |
| 5,918,733 A | 7/1999 | Cerwin et al. |
| 5,944,739 A | 8/1999 | Zlock et al. |
| 5,947,982 A | 9/1999 | Duran |
| 5,951,587 A | 9/1999 | Qureshi et al. |
| 5,954,731 A | 9/1999 | Yoon |
| 5,954,732 A | 9/1999 | Hart et al. |
| 5,954,733 A | 9/1999 | Yoon |
| 5,964,764 A | 10/1999 | West, Jr. et al. |
| 5,993,466 A | 11/1999 | Yoon |
| 5,993,467 A | 11/1999 | Yoon |
| 6,010,525 A | 1/2000 | Bonutti et al. |
| 6,036,699 A | 3/2000 | Andreas et al. |
| 6,048,351 A | 4/2000 | Gordon et al. |
| 6,051,006 A | 4/2000 | Shluzas et al. |
| 6,053,935 A | 4/2000 | Brenneman et al. |
| 6,068,648 A | 5/2000 | Cole et al. |
| 6,071,233 A | 6/2000 | Ishikawa et al. |
| 6,071,289 A | 6/2000 | Stefanchik et al. |
| 6,077,286 A | 6/2000 | Cuschieri et al. |
| 6,086,600 A | 7/2000 | Kortenbach |
| 6,086,601 A | 7/2000 | Yoon |
| 6,086,608 A | 7/2000 | Ek et al. |
| 6,095,323 A | 8/2000 | Ferguson |
| 6,096,051 A | 8/2000 | Kortenbach et al. |
| 6,117,144 A | 9/2000 | Nobles et al. |
| 6,126,666 A | 10/2000 | Trapp et al. |
| 6,135,385 A | 10/2000 | Lahidalga |
| 6,136,010 A * | 10/2000 | Modesitt ............ A61B 17/0482 606/139 |
| RE36,974 E | 11/2000 | Bonutti |
| 6,149,658 A | 11/2000 | Gardiner et al. |
| 6,159,234 A | 12/2000 | Bonutti et al. |
| 6,171,316 B1 | 1/2001 | Kovac et al. |
| 6,224,614 B1 | 5/2001 | Yoon |
| 6,277,064 B1 | 8/2001 | Yoon |
| 6,277,132 B1 | 8/2001 | Brhel |
| 6,293,961 B2 | 9/2001 | Schwartz et al. |
| 6,306,081 B1 | 10/2001 | Ishikawa |
| 6,312,448 B1 | 11/2001 | Bonutti |
| 6,352,503 B1 | 3/2002 | Matsui et al. |
| 6,358,259 B1 | 3/2002 | Swain |
| 6,443,962 B1 | 9/2002 | Gaber |
| 6,467,612 B1 | 10/2002 | Rosenfeld |
| 6,467,230 B1 | 11/2002 | Bonutti et al. |
| 6,533,795 B1 | 3/2003 | Tran et al. |
| 6,533,796 B1 | 3/2003 | Sauer et al. |
| 6,569,085 B2 | 5/2003 | Kortenbach et al. |
| 6,585,744 B1 | 7/2003 | Griffith |
| 6,596,001 B2 | 7/2003 | Stormby et al. |
| 6,635,073 B2 | 10/2003 | Bonutti |
| 6,656,182 B1 | 12/2003 | Hayhurst |
| 6,663,639 B1 | 12/2003 | Laufer et al. |
| 6,663,641 B1 | 12/2003 | Kovac et al. |
| 6,663,643 B2 | 12/2003 | Field et al. |
| 6,695,852 B2 | 2/2004 | Gleason |
| 6,699,183 B1 | 3/2004 | Wimmer |
| 6,719,763 B2 | 4/2004 | Chung et al. |
| 6,719,764 B1 | 4/2004 | Gellman et al. |
| 6,733,509 B2 | 5/2004 | Nobles et al. |
| 6,740,030 B2 | 5/2004 | Martone et al. |
| 6,755,843 B2 | 6/2004 | Chung et al. |
| 6,804,937 B2 | 10/2004 | Dey et al. |
| 6,808,491 B2 | 10/2004 | Kortenbach et al. |
| 6,866,673 B2 | 3/2005 | Oren et al. |
| 6,893,393 B2 | 5/2005 | Carillo |
| 6,896,686 B2 | 5/2005 | Weber |
| 6,921,361 B2 | 7/2005 | Suzuki et al. |
| 6,921,408 B2 | 7/2005 | Sauer |
| 6,923,819 B2 | 8/2005 | Meade et al. |
| 6,955,643 B2 | 10/2005 | Gellman et al. |
| 6,966,916 B2 | 11/2005 | Kumar |
| 6,986,737 B2 | 1/2006 | Suzuki et al. |
| 6,988,985 B2 | 1/2006 | Suzuki et al. |
| 6,988,987 B2 | 1/2006 | Ishikawa et al. |
| 6,997,931 B2 | 2/2006 | Sauer et al. |
| 7,033,370 B2 | 4/2006 | Gordon et al. |
| 7,033,379 B2 | 4/2006 | Peterson |
| 7,041,111 B2 | 5/2006 | Chu |
| 7,048,755 B2 | 5/2006 | Bonutti et al. |
| 7,060,025 B2 | 6/2006 | Long et al. |
| 7,060,077 B2 | 6/2006 | Gordon et al. |
| 7,063,710 B2 | 6/2006 | Takamoto et al. |
| 7,087,012 B2 | 6/2006 | Ishibiki |
| 7,070,044 B2 | 7/2006 | Rosenfeld |
| 7,083,630 B2 | 8/2006 | DeVries et al. |
| 7,083,638 B2 | 8/2006 | Foerster et al. |
| 7,090,686 B2 | 8/2006 | Nobles |
| 7,090,690 B2 | 8/2006 | Foerster et al. |
| 7,094,246 B2 | 8/2006 | Anderson et al. |
| 7,112,208 B2 | 9/2006 | Morris et al. |
| 7,131,979 B2 | 11/2006 | Di Carlo |
| 7,144,401 B2 | 12/2006 | Yamamoto et al. |
| 7,147,652 B2 | 12/2006 | Bonutti et al. |
| 7,150,757 B2 | 12/2006 | Fallin et al. |
| 7,153,314 B2 | 12/2006 | Laufer et al. |
| 7,175,636 B2 | 2/2007 | Yamamoto et al. |
| 7,179,277 B2 | 2/2007 | Cunningham |
| 7,191,900 B2 | 3/2007 | Opie et al. |
| 7,198,599 B2 | 4/2007 | Goto et al. |
| 7,204,802 B2 | 4/2007 | Laval |
| 7,220,266 B2 | 5/2007 | Gambale |
| 7,223,230 B2 | 5/2007 | Zirps et al. |
| 7,235,086 B2 | 6/2007 | Sauer et al. |
| 7,264,624 B2 | 9/2007 | Nash et al. |
| 7,318,802 B2 | 1/2008 | Suzuki et al. |
| 7,322,161 B2 | 1/2008 | Prescott |
| 7,326,221 B2 | 2/2008 | Sakamoto et al. |
| 7,338,504 B2 | 3/2008 | Gibbens, III et al. |
| 7,344,545 B2 | 3/2008 | Takemoto et al. |
| 7,371,215 B2 | 5/2008 | Colliou et al. |
| 7,431,694 B2 | 10/2008 | Stefanchik et al. |
| 7,527,590 B2 | 5/2009 | Suzuki et al. |
| 7,566,300 B2 | 7/2009 | Devierre et al. |
| 7,601,161 B1 | 10/2009 | Nobles et al. |
| 7,637,369 B2 | 12/2009 | Kennedy et al. |
| 7,665,279 B2 | 2/2010 | Prescott |
| 7,703,459 B2 | 4/2010 | Saadat et al. |
| 7,727,144 B2 | 6/2010 | Suzuki |
| 7,766,162 B2 | 8/2010 | Maki et al. |
| 7,775,973 B2 | 8/2010 | Okada et al. |
| 7,776,066 B2 | 8/2010 | Onuki et al. |
| 7,785,348 B2 | 8/2010 | Kuhns et al. |
| 7,918,867 B2 | 4/2011 | Dana et al. |
| 7,931,661 B2 | 4/2011 | Saadat et al. |
| 7,935,128 B2 | 5/2011 | Rioux et al. |
| 7,988,656 B2 | 8/2011 | Uesugi et al. |
| 8,016,840 B2 | 9/2011 | Takemoto et al. |
| 8,021,376 B2 | 9/2011 | Takemoto et al. |
| 8,287,556 B2 | 10/2012 | Gilkey et al. |
| 9,198,562 B2 | 12/2015 | Mitelberg et al. |
| 11,534,160 B2 | 12/2022 | Mitelberg et al. |
| 2002/0040227 A1 | 4/2002 | Harari et al. |
| 2002/0087190 A1 | 7/2002 | Benavitz et al. |
| 2002/0107530 A1 | 8/2002 | Sauer et al. |
| 2003/0176762 A1 | 9/2003 | Kammerer |
| 2003/0181924 A1 | 9/2003 | Yamamoto |
| 2003/0216613 A1 | 11/2003 | Suzuki et al. |
| 2004/0015177 A1 | 1/2004 | Chu |
| 2004/0249393 A1 | 12/2004 | Weisel et al. |
| 2004/0249394 A1 | 12/2004 | Morris et al. |
| 2004/0260314 A1 | 12/2004 | Lizardi et al. |
| 2005/0065401 A1 | 3/2005 | Saadat et al. |
| 2005/0149067 A1 | 7/2005 | Takemoto et al. |
| 2005/0154403 A1 | 7/2005 | Sauer et al. |
| 2005/0250985 A1 | 11/2005 | Saadat et al. |

(56) References Cited

U.S. PATENT DOCUMENTS

| | | |
|---|---|---|
| 2006/0281970 A1 | 12/2006 | Stokes |
| 2007/0032799 A1* | 2/2007 | Pantages ............ A61B 17/0487 |
| | | 606/144 |
| 2007/0162052 A1 | 7/2007 | Hashimoto et al. |
| 2007/0270637 A1 | 11/2007 | Takemoto et al. |
| 2008/0039255 A1 | 2/2008 | Jinno et al. |
| 2008/0045979 A1 | 2/2008 | Ma |
| 2009/0043335 A1 | 2/2009 | Capurro |
| 2009/0312775 A1 | 12/2009 | Gilkey et al. |
| 2010/0298630 A1 | 11/2010 | Wingall |
| 2012/0123471 A1 | 5/2012 | Woodward, Jr. et al. |
| 2017/0086819 A1* | 3/2017 | Raybin .............. A61B 17/0491 |
| 2023/0181183 A1 | 6/2023 | Mitleberg et al. |

OTHER PUBLICATIONS

U.S. Appl. No. 61/495,970, filed Jun. 11, 2011, Vladimir Mitelberg.
U.S. Appl. No. 61/073,340, filed Jun. 17, 2008, J. Landon Gilkey.
U.S. Appl. No. 61/162,249, filed Mar. 20, 2009, J. Landon Gilkey.

* cited by examiner

FIG. 18
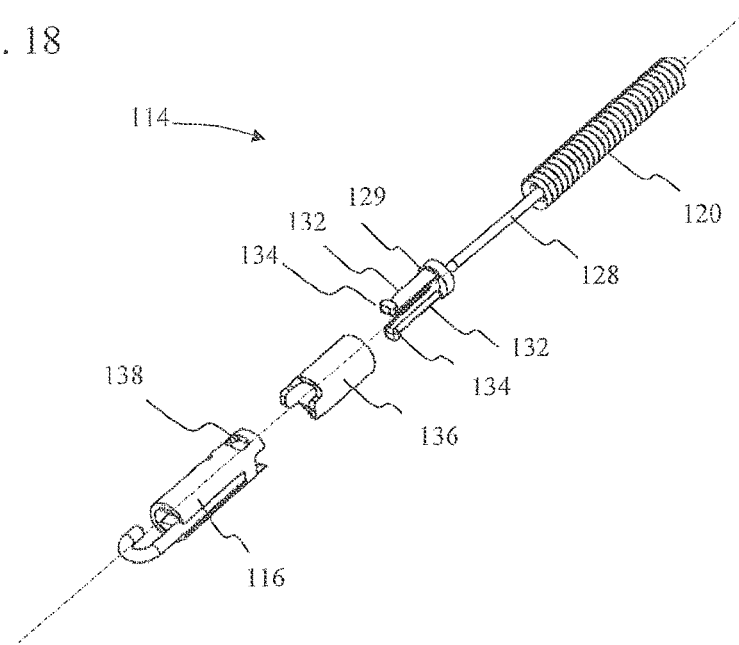
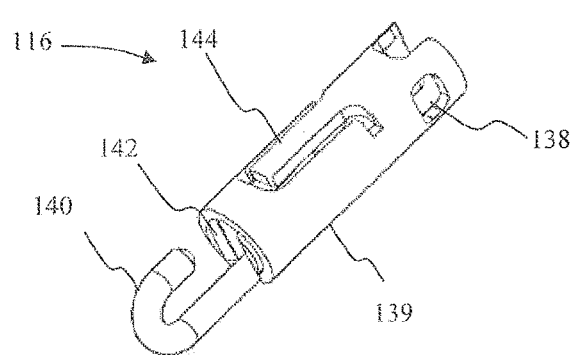
FIG. 19
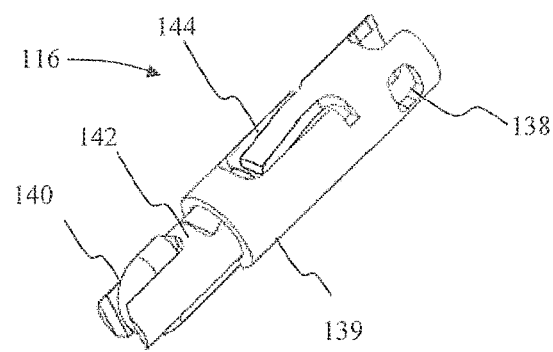
FIG. 20

FIG. 74
FIG. 75A
FIG. 75
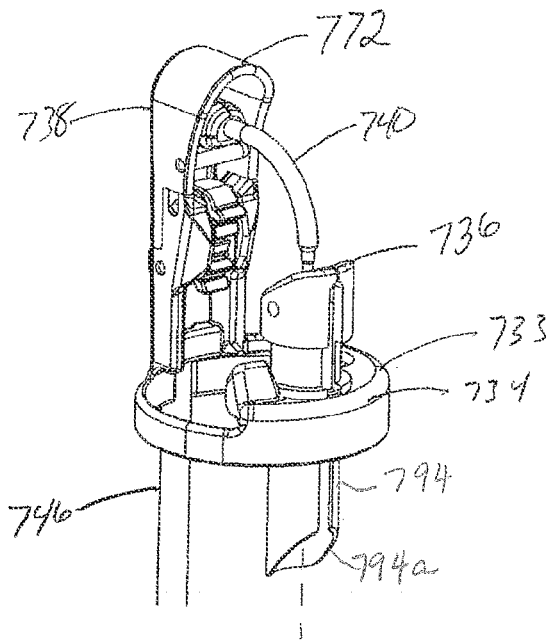
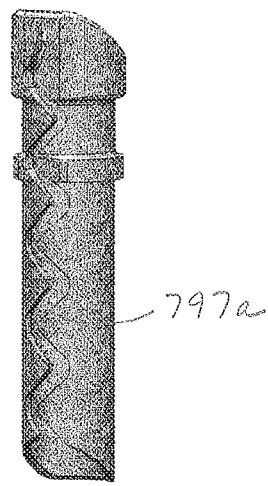
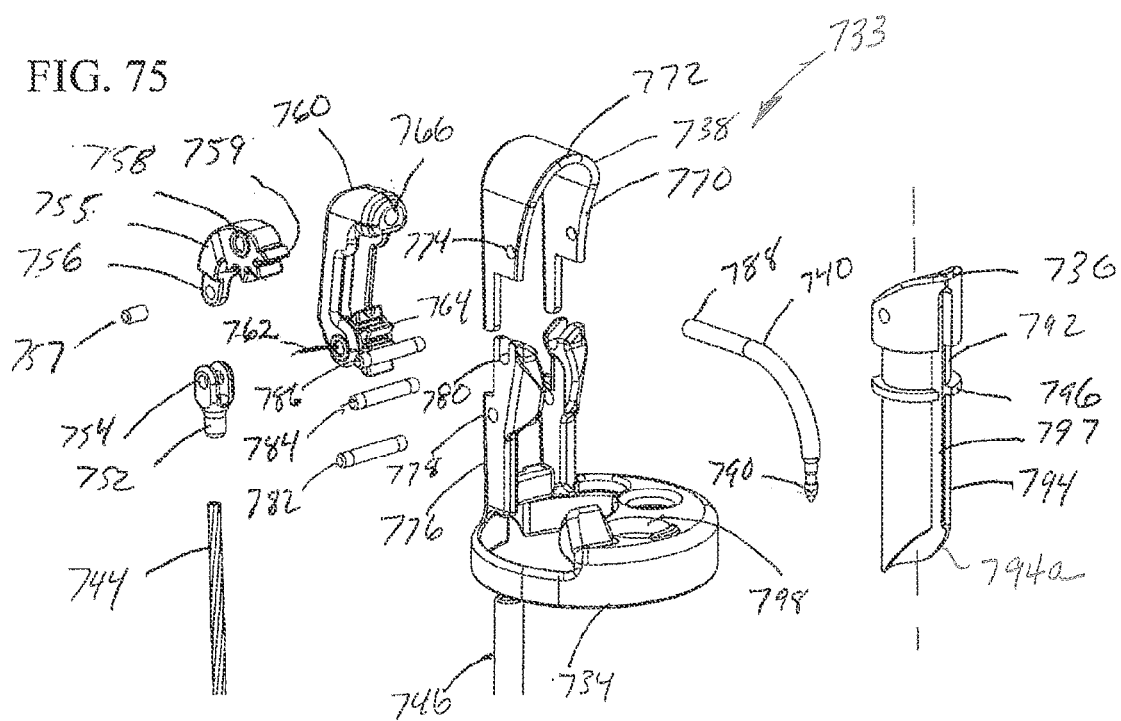

FIG. 76A
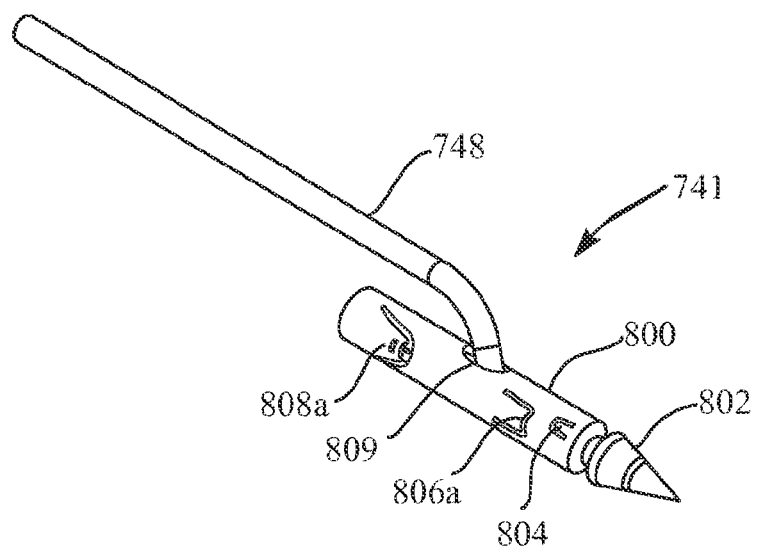
FIG. 76B
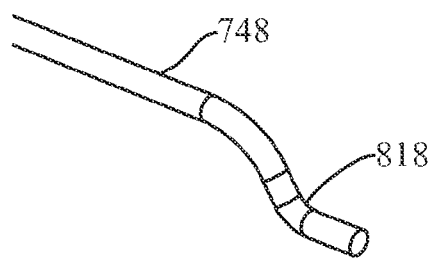
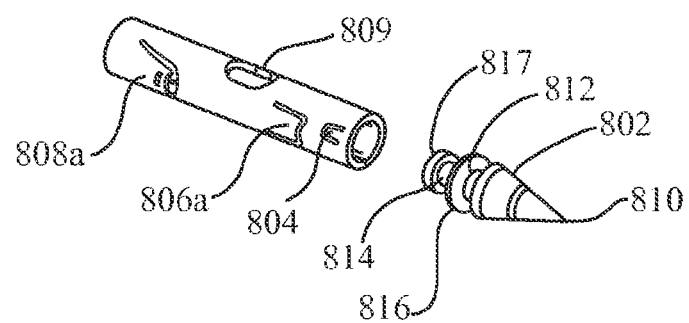

ENDOSCOPIC NEEDLE ASSEMBLY

CROSS-REFERENCE TO RELATED APPLICATIONS

This application is a continuation of U.S. application Ser. No. 16/456,692, filed Jun. 28, 2019, which is a continuation-in-part of U.S. application Ser. No. 14/924,087, filed Oct. 27, 2015, now U.S. patent Ser. No. 11/534,160, issued on Dec. 27, 2022, which is a continuation of U.S. application Ser. No. 13/328,003, filed Dec. 16, 2011, now U.S. Pat. No. 9,198,562, issued on Dec. 1, 2015, which claims priority from U.S. Provisional Application No. 61/483,679, filed May 8, 2011, and U.S. Provisional Application 61/495,970, filed Jun. 11, 2011, and which also is a continuation-in-part of U.S. application Ser. No. 12/485,576, filed Jun. 16, 2009, now U.S. Pat. No. 8,287,556, issued on Oct. 16, 2012, which claims benefit of U.S. Provisional Application No. 61/073,340, filed Jun. 17, 2008, and U.S. Provisional Application No. 61/162,249, filed Mar. 20, 2009, all of which applications are hereby incorporated by reference herein in their entireties.

BACKGROUND OF THE INVENTION

1. Field

The present invention relates to a treatment device which can be inserted into a body through a natural orifice with an endoscope or other steerable guide member. The present invention may be used to perform suturing on the tissue of a mammal, whether human or not, and whether or not alive, but is not limited thereto.

2. Description of the Related Art

U.S. Pat. No. 7,344,545 (Olympus Corporation) discloses an endoscopic suturing system having many embodiments to perform a surgical operation. This suturing system generally comprises an assembly having first and second arms which are actuatable by a push rod to rotatably approach each other while one arm grasps tissue and the second arm drives a curved needle through the tissue. The system also includes a needle recovery member requiring a rigid alignment with the curved needle arm. While this system affords the ability to grasp thick tissue, the tissue grasping arm and the arrangement of the needle recovery member provides bulk to the system making it difficult to use in endoscopic procedures.

SUMMARY

The present invention provides an endoscopic treatment device having a structure enabling a small profile for delivery while providing both a large opening and closing angle and producing a large needle force for piercing tissue to perform a surgical operation such as tissue approximation and suturing within the body.

In accordance with an aspect of the present invention there is provided an endoscopic treatment device which is used to perform treatment in a body while being operated outside the body. The treatment device comprises a flexible member coupled to a proximal handle assembly for operation outside of the body and a distal cap assembly where the cap assembly is adapted to engage the distal end of an endoscope. The flexible member is connected to a link mechanism and is actuated to cause a needle assembly having a needle holder arm and needle which are coupled to the cap assembly to move in a direction to puncture tissue and a direction to be removed from tissue.

In accordance with another aspect of the present invention there is provided an endoscopic treatment device which is used to perform treatment in a body while being operated outside the body. The treatment device comprises a flexible member coupled to a proximal handle assembly for operation outside of the body and a distal cap assembly where the cap assembly is adapted to engage the distal end of an endoscope or articulable guide member or tube. The flexible member is connected to a link mechanism and is actuated to cause a needle assembly having a needle arm with a sharpened tip, coupled to the cap assembly, to move in a direction to puncture tissue and a direction to be removed from tissue. The needle arm being configured so that after puncturing tissue, a blunt anchor assembly can be remove ably attached to the needle arm tip. As the needle arm is opened to remove it from tissue the blunt anchor assembly (which includes affixed suture) is drawn through the previously pierced tissue.

According to another aspect of the present invention there is provided an endoscopic treatment system for use with an endoscope having a cap assembly adapted to be positioned at the distal end of an endoscope where the cap assembly has at least one mounting bracket which is fixedly attached. A transmission member with a flexible structure has a distal end portion that is inserted into a body and is capable of being operated outside the body by a proximal portion coupled to a handle assembly. A push rod is coupled to the distal end portion of the transmission member. A connecting member having a needle holder arm is coupled to the push rod and pivotally coupled to the mounting bracket. A removable needle is connected to the needle holder arm and is adapted to pierce tissue. When the push rod is actuated by the transmission member, the connecting member moves the needle holder arm in a direction to pierce tissue or in a direction to remove it from tissue. An elongate needle capture device is positioned within the instrument channel of the endoscope and has a distal end adapted to receive and grasp the needle and a proximal end coupled to a handle assembly.

In accordance with another aspect of the present invention there is provided a removable needle assembly having a needle tip member and a needle base member. The needle tip member has a sharpened end which is adapted to pierce tissue and a hollow end to receive the needle base member. The needle tip member also includes an aperture which may take the form of a longitudinal slot through the wall adjacent the hollow end which is adapted to allow suture to extend there from. The needle base member has a first end which is adapted to engage the hollow end of the needle tip member and a second end which is adapted to removably engage a needle holder arm. The needle base member further includes a stop member which when coupled with the needle holder arm limits the depth to which the needle base is inserted into the needle holder arm. The coupling engagement of needle tip member and the first end of the needle base member are adapted to secure a length of suture material to the needle assembly and allow it to extend through the aperture adjacent the hollow end of the needle tip member.

In accordance with still another aspect of the present invention there is provided a needle clip assembly having first and second ends where a needle tip adapted for piercing tissue is positioned at the first end and a tissue stop member is positioned at the second end. The needle clip assembly has a constrained first configuration and an unconstrained second configuration where the needle clip assembly is resiliently biased to move from the first configuration to the second configuration. The constrained first configuration may take the form of a generally straightened elongate member. The unconstrained second configuration may take the form of a loop, helix or substantially closed loop form.

In accordance with yet another aspect of the present invention there is provided an endoscopic treatment system for use with an endoscope having a cap assembly adapted to be positioned at the distal end of an endoscope where the cap assembly has two pair of fixedly attached mounting brackets. A transmission member with a flexible structure has a distal end portion that is inserted into a body and is capable of being operated outside the body. A push rod is coupled to the distal end portion of the transmission member. A connecting member having a needle holder arm is coupled to the push rod and pivotally coupled to the outer pair of mounting brackets. A link member having two ends is pivotally coupled to the inner pair of mounting brackets at one end and pivotally coupled to the needle holder arm at the other end. A removable needle is connected to the needle holder arm and is adapted to pierce tissue. When the push rod is actuated by the transmission member, the connecting member moves the needle holder arm in a direction to pierce tissue or a direction to remove it from tissue. An elongate needle capture device is positioned within the instrument channel of the endoscope having a proximal handle and a distal end adapted to receive and grasp the needle.

In accordance with yet another aspect of the present invention there is provided a combination handle assembly adapted to operate the movement of the transmission member thereby opening and closing the needle arm and adapted to operate the needle capture device to thereby grasp and release the needle. The handle assembly includes a handle main body coupled to an endoscope channel coupling which is adapted to engage the instrument channel of an endoscope. An elongate needle capture device includes a proximal housing which is removably coupled to the handle main body and a distal end is which positioned through the endoscope channel coupling into the instrument channel of an end. An actuatable trigger lever is coupled to handle main body and operates the transmission member to axially advance or retract the transmission member.

In accordance with another aspect of the present invention there is provided an endoscopic treatment system that further includes a tissue grasping member. The tissue grasping member takes the form of an elongate member having proximal and distal ends and is positioned with a channel of an endoscope. The distal end of the tissue grasping member may take the form of a helix or tapered spiral in which rotation of the helix when at a desired site adjacent tissue, causes the helix to substantially engage the tissue and allow the tissue to be retracted.

In accordance with still another aspect of the present invention there is provided an endoscopic treatment system that further includes a tissue grasping member. The tissue grasping member takes the form of an elongate member having proximal and distal ends and is positioned with a channel of an endoscope. The distal end of the tissue grasping member may take the form of a pair of jaws such that when at a desired site adjacent tissue, operation of the jaws causes the jaws to substantially engage the tissue and allow the tissue to be retracted.

In accordance with another aspect of the present invention there is provided an endoscopic treatment device which is used to perform treatment in a body while being operated outside the body. The treatment device comprises a flexible member coupled to a proximal handle assembly for operation outside of the body and a distal cap assembly where the cap assembly is adapted to engage the distal end of an endoscope. The cap assembly includes an elongate channel lock member having one end which is fixedly attached to the cap assembly and extends through the channel of an endoscope and is removably secured to the proximal end of the endoscope channel. The channel lock member may take the form of a small diameter flexible wire assembly or wire braid assembly.

In accordance with yet another aspect of the present invention there is provided an endoscopic suturing system for use with an endoscope having a cap assembly adapted to be positioned at the distal end of an endoscope where the cap assembly defines mounting locations. A transmission member with a flexible structure has a distal end portion that is inserted into a body and is capable of being operated outside the body. A push member is optionally coupled to the distal end portion of the transmission member. A link member having a geared portion is coupled to the push member or the transmission member and pivotally coupled at a first mounting location. A connecting member having a geared portion and a needle holding arm at one end is pivotally coupled at a second mounting location such that the geared portions of the link member and the connecting member intermesh.

In accordance with another aspect of the present invention there is provided an endoscopic suturing system for use with an endoscope having a cap assembly adapted to be positioned at the distal end of the endoscope where the cap assembly includes an elongate needle guard. The needle guard generally extends from a base of the cap in a direction distal to the end of the endoscope. Preferably the needle guard extends in a distal direction parallel to the axis of the endoscope. The needle guard is adapted to prevent tissue from inadvertently contacting the needle tip while the needle tip is in an open position and the tissue is being positioned for suturing.

In accordance with another aspect of the present invention there is provided an endoscopic suturing system for use with an endoscope having a cap assembly adapted to be positioned at the distal end of the endoscope where the cap assembly includes an elongate channel guard. The channel guard generally extends from a base of the cap in a direction distal to the end of the endoscope and is coaxial with the endoscope channel which used by the needle capture device. The channel guard is adapted to aid in suturing by positioning tissue a sufficient distance away from the end of the endoscope channel allowing for better visualization and providing a surface to support the tissue during the suturing operation. Preferably, the distal end of the channel guard is inclined to provide a plane which is generally perpendicular to the needle tip as the needle tip intersects the plane along the needle suturing path. Preferably, the minimum length that the channel guard extends from the cap is related to the field of view from the endoscope such that minimum length allows sufficient tissue to be visualized when the tissue is placed in a position for suturing.

In accordance with another aspect of the present invention there is provided an endoscopic treatment device which is used to perform treatment in a body while being operated outside the body. The treatment device comprises a flexible member coupled to a proximal handle assembly for operation outside of the body and a distal cap assembly where the cap assembly is adapted to engage the distal end of an endoscope. The cap assembly includes an elongate channel lock member having one end which is removably secured to the cap assembly and extends through the channel of an endoscope and is removably secured to the proximal end of the endoscope channel by a tensioning assembly. The channel lock member may take the form of a small diameter flexible wire assembly or wire braid assembly. Preferably, the channel lock member includes retaining members fixedly secured to each end. The tensioning assembly includes a bayonet lock fitting adapted to engage a bayonet prong on the endoscope, a housing member, a rotatable wheel member having a tab member and a tensioner member. The proximal end of the channel lock member is secured to the tab member of the rotatable wheel such that rotation of the wheel applies a preset tension to the channel lock member. The housing member of the tensioning assembly in conjunction with the tensioner member, preferably formed of a spring, maintains the tension on the channel lock member by resisting compression during normal bending operation of the endoscope.

According to another aspect of the endoscopic treatment system of the present invention there is provided a cinch system including a cinch delivery device and a cinch device. The cinch delivery device takes the form of an elongate tubular member having proximal end coupled to a handle assembly and a distal end. The distal end of the cinch delivery device is removably coupled to the cinch device. The cinch device has a housing that incorporates a suture capture hook at is distal end for capturing suture that has been placed through tissue. A cinch plug is positioned within the cinch housing and is movable from a first suture non-retaining position to a second suture retaining position for securing suture in a fixed position by operating the handle assembly. Once suture has been secured by the cinch plug in the cinch housing the handle assembly may be operated to uncouple the cinch device from the cinch delivery tool.

According to still another aspect of the present invention, there is provided a suturing method using an endoscopic suturing system. This method comprises the steps of:
(1) inserting a guide tube and/or endoscope into a body with a suturing device coupled to the endoscope and or guide tube;
(2) opening a needle arm of the suturing device having a removable needle;
(3) pushing the needle against tissue at a desired suture site;
(4) closing the needle arm of the suturing device;
(5) piercing the tissue with the needle;
(6) recovering the needle by using a needle capture device;
(7) removing the needle from the tissue;
(8) opening the needle arm to remove it from tissue;
(9) closing the needle arm; and
(10) removing the suturing device from the body.

According to yet still another aspect of the present invention, there is provided a suturing method using an endoscopic suturing system. This method comprises the steps of:
(1) inserting a guide tube and/or endoscope into a body with a suturing device coupled to the endoscope and or guide tube;
(2) opening a needle arm of the suturing device having a sharp tip;
(3) pushing the needle arm tip against tissue at a desired suture site;
(4) closing the needle arm of the suturing device;
(5) piercing the tissue with the needle arm tip;
(6) attaching an blunt anchor assembly to the needle arm tip by using a capture device;
(7) opening the needle arm to remove it from tissue;
(8) advancing the blunt anchor assembly through the pierced tissue;
(9) closing the needle arm;
(10) recovering the blunt anchor assembly from the needle arm using a capture device;
(11) releasing the blunt anchor assembly from the capture device; and
(12) removing the suturing device from the body.

According to yet another aspect of the present invention, there is provided a suturing method using an endoscopic suturing system including a tissue grasper. This method comprises the steps of:
(1) inserting a guide tube into a body;
(2) inserting a suturing device coupled to an endoscope into the guide tube and into the body;
(3) opening a needle arm of the suturing device having a removable needle;
(4) engaging a tissue adjacent a desired suture site using a tissue grasper;
(5) pushing the needle against tissue at a desired suture site;
(6) closing the needle arm of the suturing device;
(7) piercing the tissue with the needle;
(8) recovering the needle by using a needle capture device;
(9) removing the needle from the tissue;
(10) opening the needle arm to remove it from tissue;
(11) releasing the tissue from the tissue grasper;
(12) closing the needle arm; and
(13) removing the suturing device from the body.

According to another aspect of the present invention, there is provided a suturing method of performing a running stitch using an endoscopic suturing system. This method comprises the steps of:
(1) inserting a guide tube into a body;
(2) inserting a suturing device coupled to the endoscope into the guide tube and inserting the suturing device into the body;
(3) opening a needle arm of the suturing device having a removable needle;
(4) pushing the needle against tissue at a desired suture site;
(5) closing the needle arm of the suturing device;
(6) piercing the tissue with the needle;
(7) recovering the needle by using a needle capture device;
(8) removing the needle from the tissue;
(9) opening the needle arm to remove it from tissue;
(10) closing the needle arm;
(11) inserting the needle into the needle arm endoscopically using the needle capture device;
(12) performing steps (3) through (11) as needed.

According to yet another aspect of the present invention, there is provided a suturing method of performing a running stitch using an endoscopic suturing system. This method comprises the steps of:
(1) inserting a guide tube and/or endoscope into a body with a suturing device coupled to the endoscope and or guide tube;
(2) positioning the suturing device adjacent to a target tissue location in the body;
(3) opening a needle arm of the suturing device having a sharp tip;
(4) pushing the needle arm tip against tissue at a desired suture site;
(5) closing the needle arm of the suturing device;
(6) piercing the tissue with the needle arm tip;

(7) attaching an blunt anchor assembly to the needle arm tip by using a capture device;

(8) opening the needle arm to remove it from tissue;

(9) advancing the blunt anchor assembly through the pierced tissue;

(10) closing the needle arm;

(11) recovering the blunt anchor assembly from the needle arm using a capture device;

(12) performing steps (2) through (11) as needed.

According to still yet another aspect of the present invention there is provided a method of securing tissue using an endoscopic suturing system including a resilient pre-biased needle clip and a tissue grasper. This method comprises the steps of:

(1) inserting a guide tube into a body;

(2) inserting a suturing device coupled to the endoscope into the guide tube and inserting the suturing device into the body;

(3) opening a needle holding arm of the suturing device having a removable needle clip;

(4) engaging a tissue adjacent a desired suture site using a tissue grasper (5) pushing the needle clip against tissue at a desired suture site;

(6) closing the needle holding arm of the suturing device;

(7) piercing the tissue with the needle clip;

(8) grasping the needle clip tip using a needle capture device;

(9) opening the needle holding arm to remove it from tissue;

(10) releasing the needle clip from the needle capture device

(11) releasing the tissue from the tissue grasper;

(12) closing the needle holding arm; and

(13) removing the suturing device from the body.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 18 is an enlarged exploded view of the distal end of the cinch and cinch delivery device;

FIG. 19 is an enlarged view of the cinch device in an open configuration;

FIG. 20 is an enlarged view of the cinch device in a closed configuration;

FIG. 24 through FIG. 34 illustrate steps in a surgical suturing procedure using an endoscopic suturing system according to an embodiment of the present invention wherein FIG. 24 is a view of a step in which a an endoscopic suturing device is positioned adjacent a wound at a desired treatment location;

FIG. 25 is a view of a step in which a tissue grasper is extended adjacent a wound at a desired treatment location;

FIG. 26 is a view of a step in which a tissue grasper engages tissue and is slightly retracted to bring tissue closer to the endoscope;

FIG. 27 is a view of an alternative step in which a tissue grasper engages tissue and is substantially retracted to bring tissue in contact with the endoscope;

FIG. 28 is a view of a step in which the needle pierces tissue;

FIG. 29 is a view of a step in which the needle holder arm is removed from the tissue depositing a suture through the tissue;

FIG. 30 is a view of a step in which the tissue grasper disengages the tissue;

FIG. 31 is a view of a step in which the needle is reloaded into the needle holder arm;

FIG. 32 is a view of a step in which a cinch device captures suture;

FIG. 33 is a view of a step in which the suture is tightened using the cinch device to thereby close the wound;

FIG. 34 is a view of a cinch device released from the cinch delivery device;

FIG. 35 through FIG. 38 illustrate steps in a surgical suturing procedure using an endoscopic suturing system according to another embodiment of the present invention wherein FIG. 35 is a view of a step in which a an endoscopic suturing device has delivered a needle through tissue at a desired treatment location;

FIG. 36 is a view of a step in which a cinch device captures suture;

FIG. 37 is a view of a step in which the suture is tightened using the cinch device to thereby close the wound;

FIG. 38 is a view of a cinch device released from the cinch delivery device;

FIG. 39 through FIG. 42 illustrate steps in a surgical suturing procedure using an endoscopic suturing system according to yet another embodiment of the present invention wherein FIG. 39 is a view of a step in which an endoscopic suturing device having a needle clip is positioned at a desired treatment location;

FIG. 40 is a view of a step in which the needle clip pierces tissue;

FIG. 41 is a view of a step in which the needle holder arm is removed from the tissue depositing the needle clip through the tissue;

FIG. 42 is a view of a step in which the tissue grasper disengages the tissue and the needle clip close the wound;

FIG. 56A illustrates the needle capture assembly in a normally closed configuration and FIG. 56B illustrates the needle capture assembly in an open configuration;

FIG. 63 through FIG. 69 illustrate steps in a surgical suturing procedure using an endoscopic suturing system according to another embodiment of the present invention wherein FIG. 63 is a view of a step in which a an endoscopic suturing device is positioned adjacent a wound at a desired treatment location;

FIG. 64 is a view of a step in which a tissue grasper is extended adjacent a wound at a desired treatment location;

FIG. 65 is a view of a step in which a tissue grasper engages tissue and is slightly retracted to bring tissue closer to the endoscope;

FIG. 66 is a view of an alternative step in which a tissue grasper engages tissue and is substantially retracted to bring tissue in contact with the endoscope;

FIG. 67 is a view of a step in which the needle partially pierces tissue;

FIG. 68 is a view of a step in which the needle completely pierces tissue;

FIG. 69 is a view of a step in which the needle holder arm is removed from the tissue depositing a suture through the tissue;

FIG. 74 is a perspective enlarged view of the cap assembly of an endoscopic suturing system according to an embodiment of the present invention where the actuating arm of the suturing device is closed;

FIG. 75 is a perspective enlarged exploded view of the cap assembly of an endoscopic suturing system according to an embodiment of the present invention;

FIG. 75A is a perspective view of an alternate embodiment of an integral tissue guard and mounting portion for the cap assembly of FIG. 75;

FIG. 76A is an illustrative view of a needle assembly for use with an endoscopic suturing device according to another embodiment of the present invention;

FIG. 76B is an exploded view of a needle assembly of FIG. 76A;

FIG. 92 through FIG. 99 illustrate steps in a surgical suturing procedure using an endoscopic suturing system according to yet another embodiment of the present invention wherein FIG. 92 is a view of a step in which a an endoscopic suturing device is positioned adjacent a wound at a desired treatment location;

FIG. 93 is a view of a step in which a tissue grasper is extended adjacent a wound at a desired treatment location;

FIG. 94 is a view of a step in which a tissue grasper engages tissue and is slightly retracted to bring tissue closer to the endoscope;

FIG. 95 is a view of an alternative step in which a tissue grasper engages tissue and is substantially retracted to bring tissue in contact with the endoscope;

FIG. 96 is a view of a step in which the needle partially pierces tissue;

FIG. 97 is a view of a step in which the needle completely pierces tissue;

FIG. 98 is a view of a step in which the needle holder arm is partially removed from tissue;

FIG. 99 is a view of a step in which the needle holder arm is removed from the tissue depositing a suture through the tissue;

FIGS. 103A and 103B are cross sectional views of the proximal and distal portions of a helical tissue grasper in a second position;

FIG. 104A is an illustrative view of an anchor assembly for use with an endoscopic suturing device according to another embodiment of the present invention;

FIG. 104B is an exploded view of an anchor assembly of FIG. 104A;

FIG. 105A is a partial section view of an anchor assembly for use with an endoscopic suturing device according to an embodiment of the present invention;

FIG. 105B is a partial section view of an anchor assembly for use with an endoscopic suturing device according to an embodiment of the present invention;

FIG. 106 is a partial section view of an anchor assembly engaged with a needle holder arm for use with an endoscopic suturing device according to an embodiment of the present invention;

FIG. 107 is an enlarged partial section view of a distal end of a needle capture device of FIG. 79 engaged with an anchor assembly for use with an endoscopic suturing device according to another embodiment of the present invention;

FIG. 108 through FIG. 115 illustrate steps in a surgical suturing procedure using an endoscopic suturing system according to yet another embodiment of the present invention wherein FIG. 108 is a view of a step in which a an endoscopic suturing device is positioned adjacent a wound at a desired treatment location;

FIG. 109 is a view of a step in which a tissue grasper is extended adjacent a wound at a desired treatment location;

FIG. 110 is a view of a step in which a tissue grasper engages tissue and is slightly retracted to bring tissue closer to the endoscope;

FIG. 111 is a view of an alternative step in which a tissue grasper engages tissue and is substantially retracted to bring tissue in contact with the endoscope;

FIG. 112 is a view of a step in which the needle partially pierces tissue;

Figure 113:
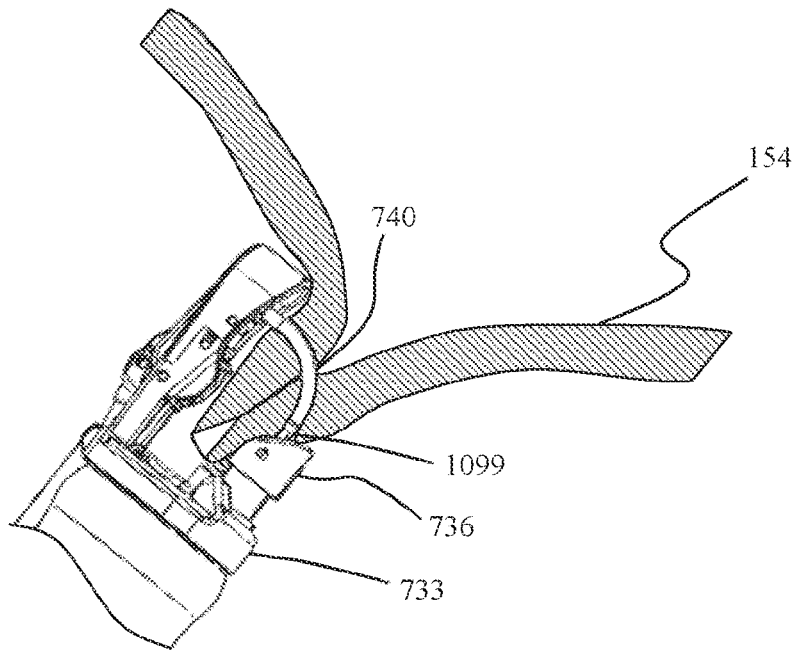
Figure 114:
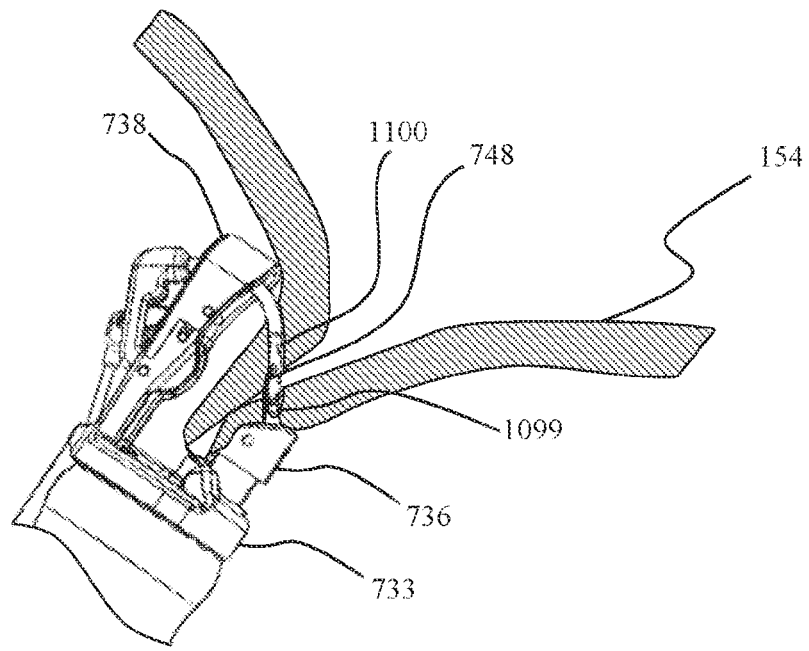
Figure 115:
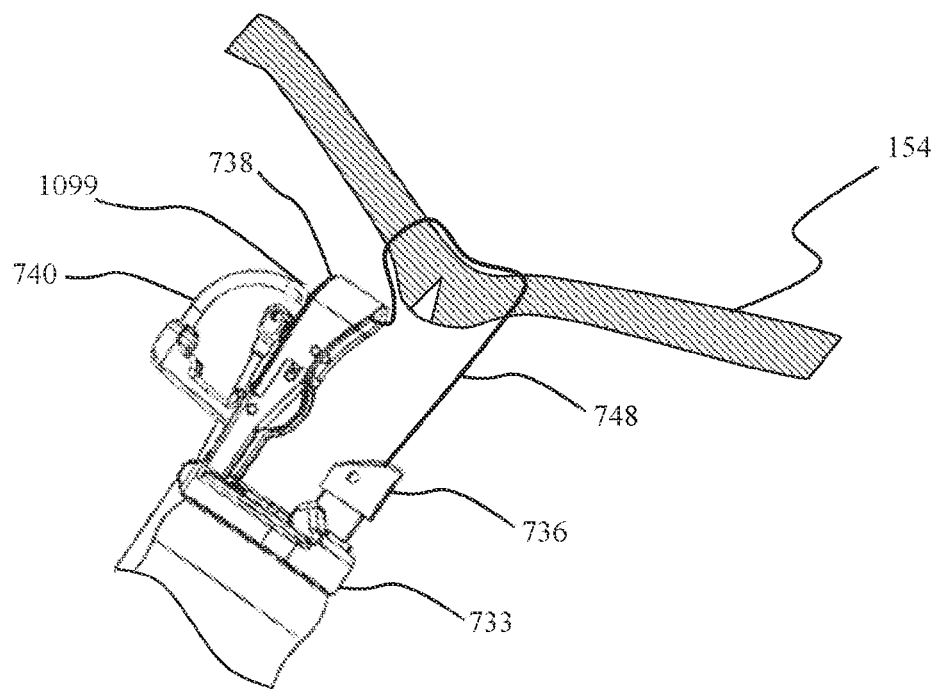

FIG. 113 is a view of a step in which the needle completely pierces tissue;

FIG. 114 is a view of a step in which the needle holder arm is partially removed from tissue;

FIG. 115 is a view of a step in which the needle holder arm is removed from the tissue depositing a suture through the tissue;

DETAILED DESCRIPTION

Figure 1:
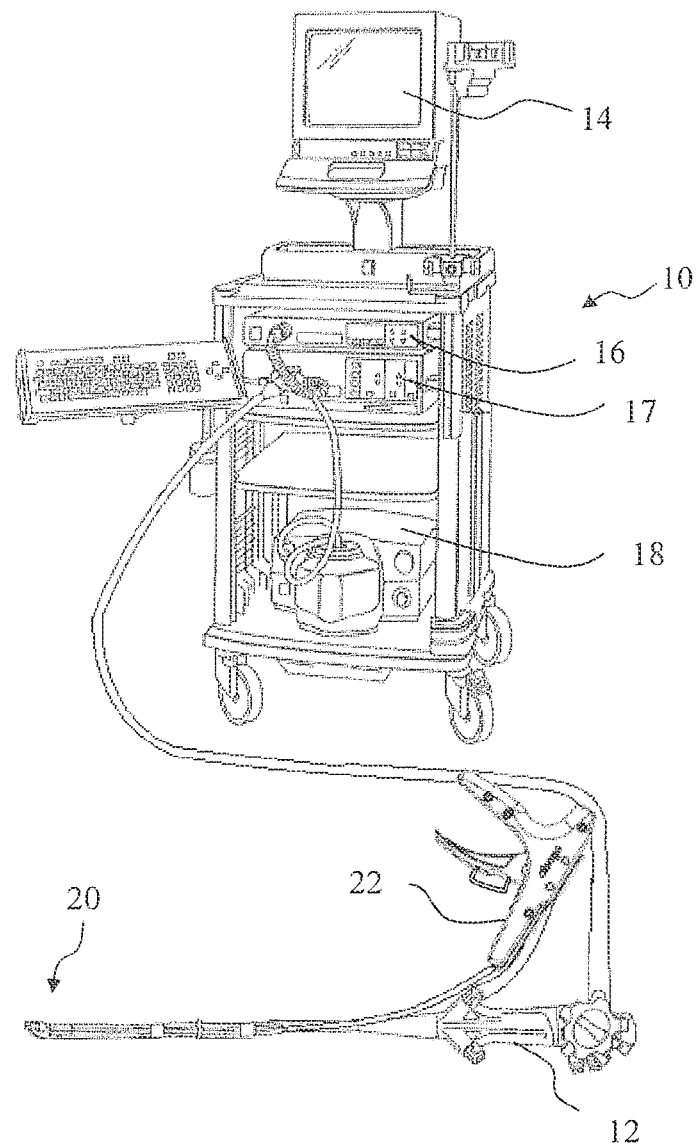
FIG. 1 is an illustrative view showing an endoscopic suturing system with endoscope system according to a first embodiment of the present invention.
Figure 2:
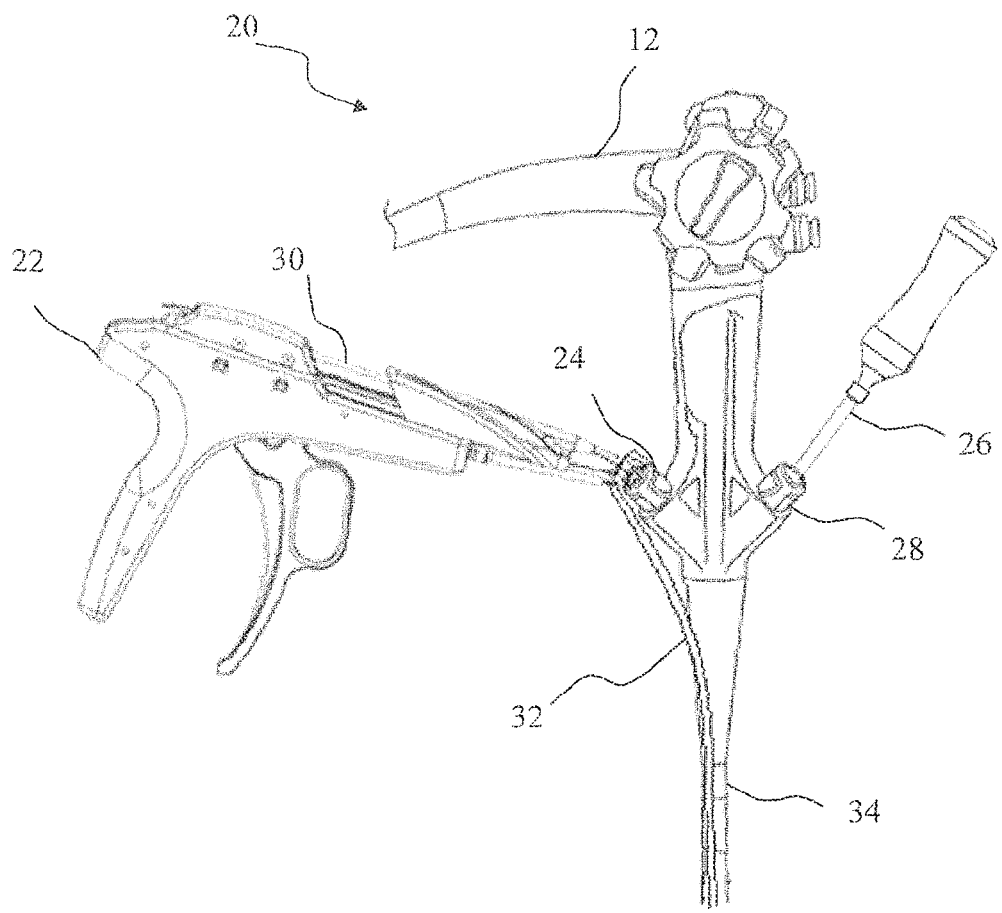
FIG. 2 is an enlarged view of the proximal portion of an endoscope and an endoscopic suturing system shown in FIG. 1.
Figure 3:
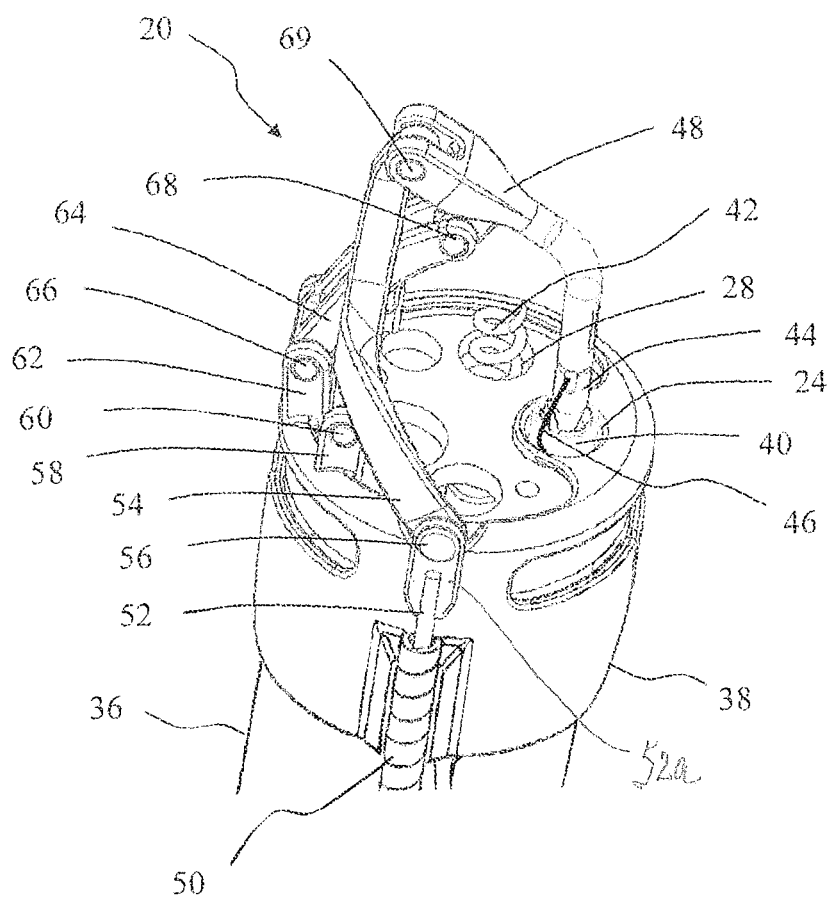
FIG. 3 is a perspective enlarged view of the distal end of an endoscopic suturing system according to an embodiment of the present invention where the actuating arm of the suturing device is closed.

As shown in FIG. 1 an endoscope system 10 which comprises an endoscope 12, a video display unit 14, an image processing device 16, a light source 17, a suction device 18 is used with and an endoscopic suturing device 20 as part of an endoscopic treatment system according to one embodiment of the present invention. FIG. 2 and FIG. 3 illustrate respectively the proximal and distal portions of endoscope 12 and endoscopic suturing device 20. The endoscopic suturing device 20 has an operable handle 22 which is removably coupled to endoscope 12 at a first instrument channel 24. A tissue grasper 26 which is used to gather tissue is shown positioned within a second instrument channel 28 of endoscope 12. The endoscopic suturing device 20 includes an elongate needle capture device 30 which is removably coupled to handle 22 and extends to the distal end of endoscope 12 slidably positioned within instrument channel 24. The endoscopic suturing device 20 is operated by handle 22 which is proximally coupled to transmission assembly 32 which extends distally along the exterior of insertion tube 34 to the distal end 36 of endoscope 12. The transmission assembly is coupled at its distal end to a cap assembly 38 which is positioned over the distal end 36 of endoscope 12. FIG. 3 shows the distal end 40 of needle capture device 30 and the distal end helical tip 42 of tissue grasper 26 extending from instrument channels 24 and 28 respectively. Positioned adjacent to needle capture device distal end 40 is needle assembly 44 which is connected to suture 46. Needle assembly 44 is removably inserted into needle holder arm 48. Transmission assembly 32 comprises an outer sheath 50 which is preferably formed of a flexible coil and a push rod 52 positioned within the lumen and extending from the distal end of outer sheath 50. Outer sheath 50 is fixedly secured to cap assembly 38. Push rod 52 is coupled to a connecting member 54 via a pivot pin 56, and optionally via a push member 52a which may couple the rod 52 and the pivot pin 56. The connecting member 54 is also connected to a pair of outer mounting brackets 58 via pivot pin 60. The mounting brackets 58 are fixedly attached to cap assembly 38. A pair of inner mounting brackets 62 are fixedly attached to the cap assembly 38 and pivotally connected to one end of a link member 64 via pivot pin 66. The other end of link member 64 is connected to the needle holder arm 48 via pivot pin 68. Needle holder arm 48 is coupled to connecting member 54 via pivot pin 69.

Figure 4:
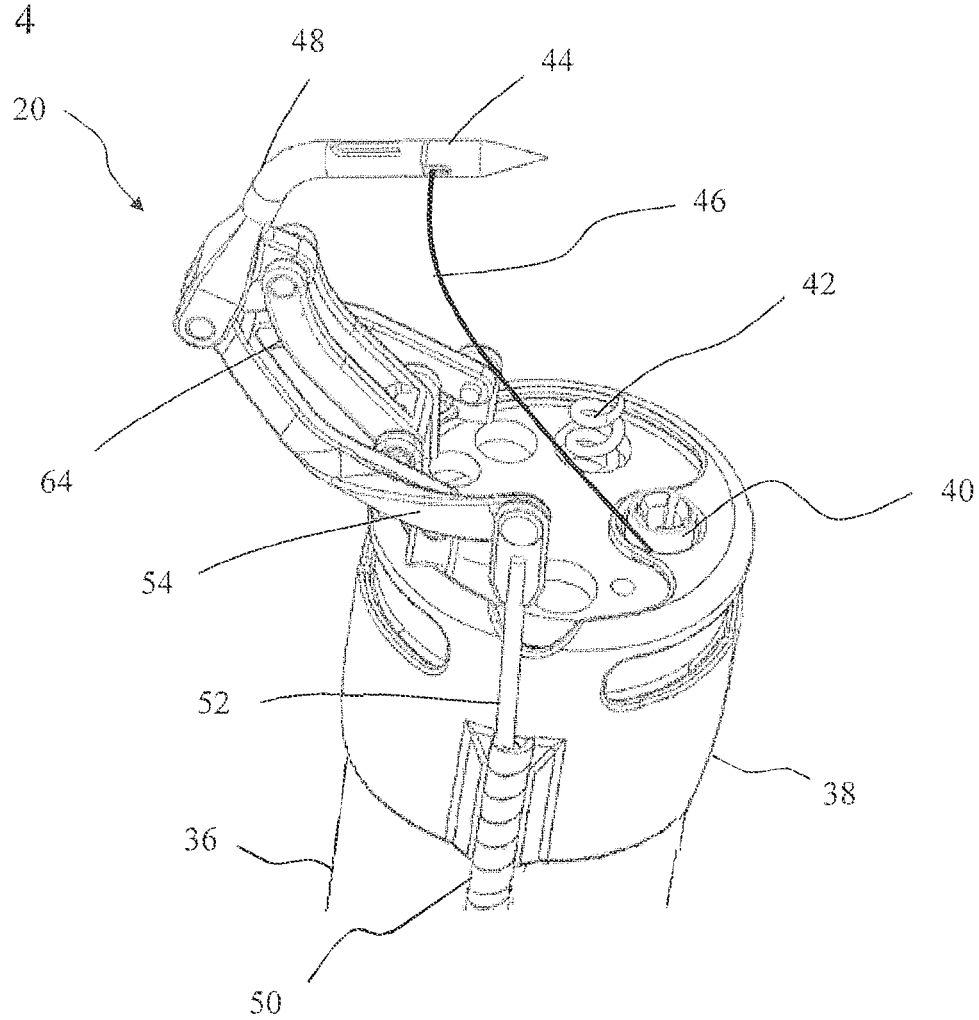
FIG. 4 is a perspective enlarged view of the distal end of an endoscopic suturing system according to an embodiment of the present invention where the actuating arm of the suturing device is open.
Figure 5:
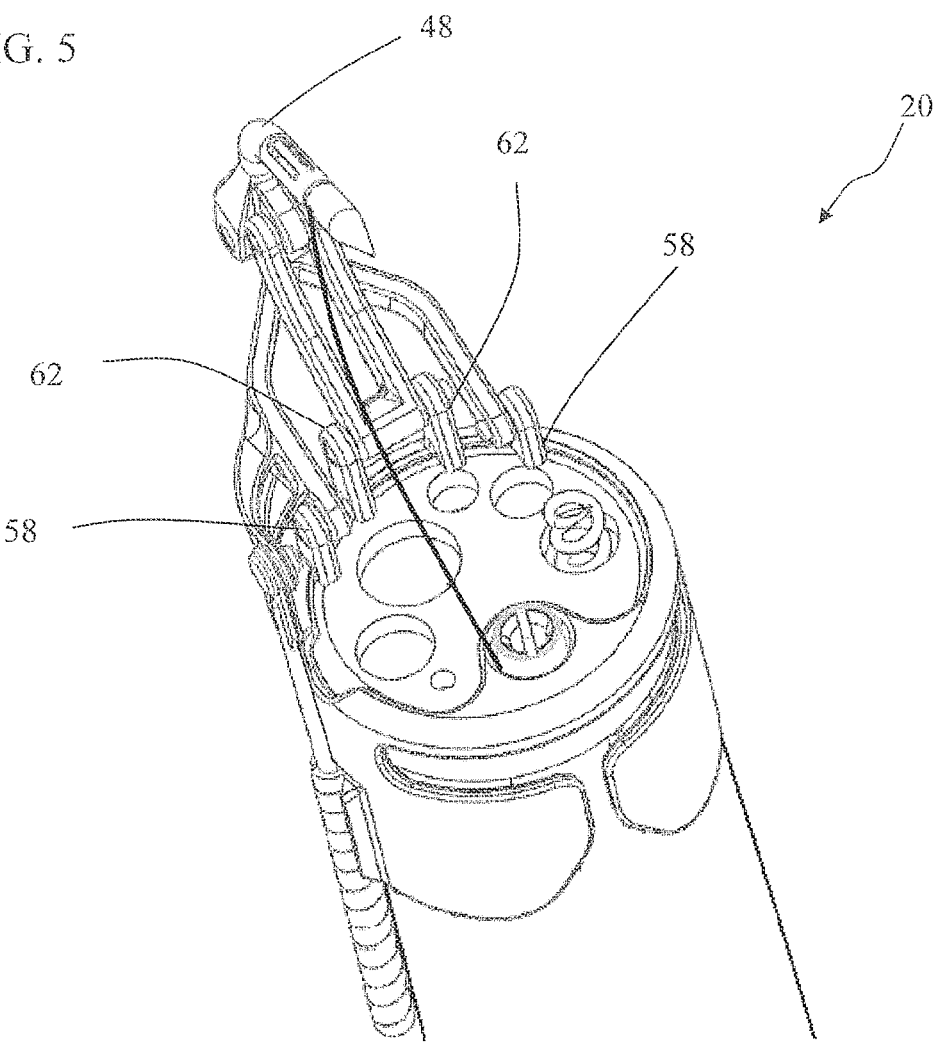
FIG. 5 is another perspective enlarged view of the distal end of an endoscopic suturing system according to an embodiment of the present invention where the actuating arm of the suturing device is open.

As shown in FIG. 3, FIG. 4, and FIG. 5, the pivotable connections of connecting member 54 and link member 64 to outer and inner mounting brackets 58 and 62 respectively, allow the rotation of needle holder arm 48 when push rod 52 is axially advanced or retracted. In FIG. 4, the cap assembly 38 is shown in an open configuration with push rod 52 advanced (compare FIG. 3 where the cap assembly is in a closed configuration with push rod 52 retracted). FIG. 5 shows the endoscopic suturing device 20 in an open configuration and from another angle where outer and inner pairs of mounting brackets 58 and 62 are more visible.

Figure 6:
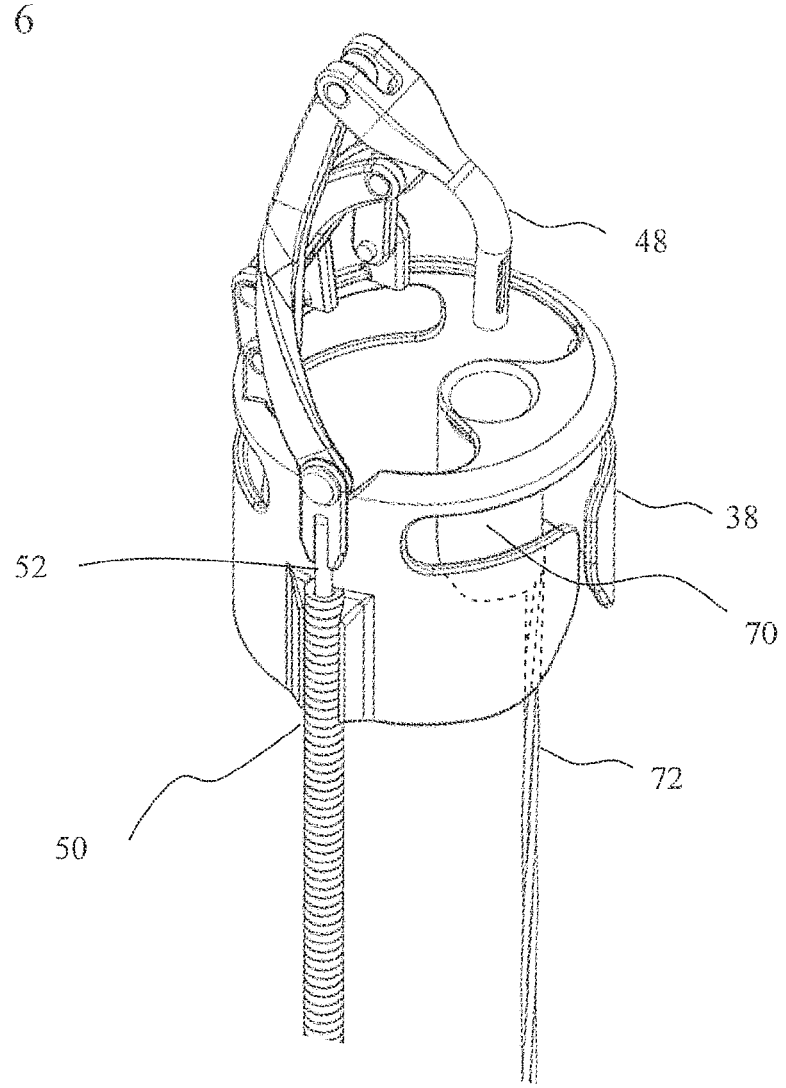
FIG. 6 is a perspective enlarged view of the cap assembly of an endoscopic suturing system according to an embodiment of the present invention where the actuating arm of the suturing device is closed.

FIG. 6 shows a view of cap assembly 38 uncoupled from an endoscope. Cap assembly 38 includes a fixedly attached insert guide 70 coupled to a flexible channel lock 72. Insert guide 70 is a tubular projection from cap assembly 38 and is adapted to be positioned within the lumen of an endoscope instrument channel at its distal end. The elongate flexible channel lock 72 extends from the insert guide 70 through an instrument channel and is secured to the proximal end of the instrument channel. The channel lock 72 ensures that the cap assembly 38 does not inadvertently disengage from the distal end of the endoscope. Preferably channel lock 72 takes the form of a small diameter single or multi stranded wire or cable formed primarily of metals or polymers. Additionally the small diameter of channel lock 72 allows room for other instruments to be positioned within the instrument channel of the endoscope.

Figure 7:
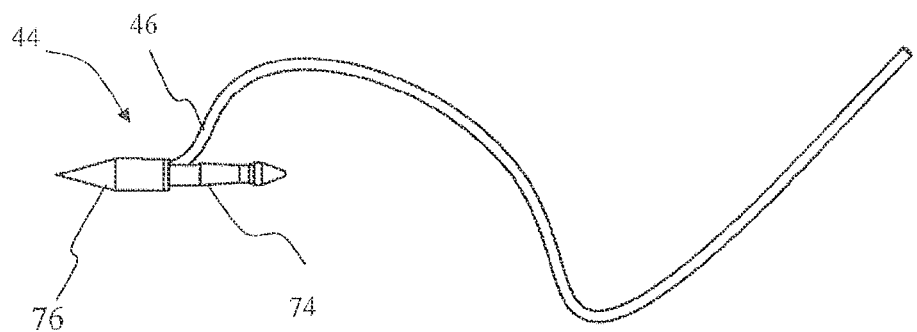
FIG. 7 is an illustrative view of a needle assembly for use with an endoscopic suturing device according to an embodiment of the present invention.
Figure 8:
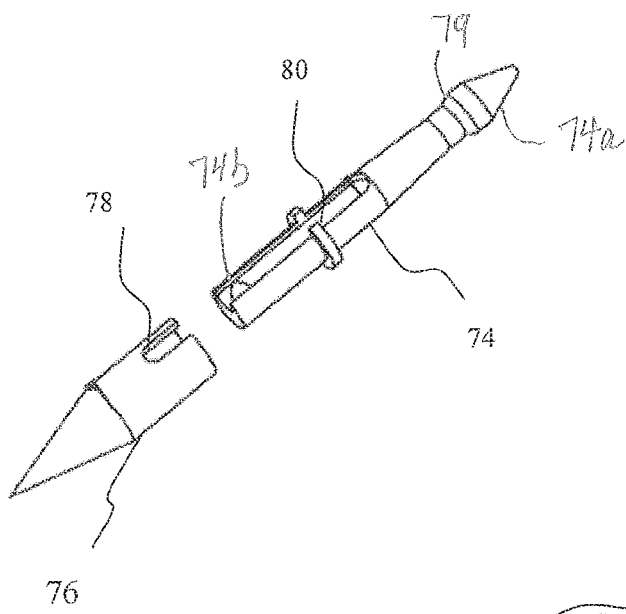
FIG. 8 is an exploded view of a needle assembly of FIG. 7.
Figure 9:
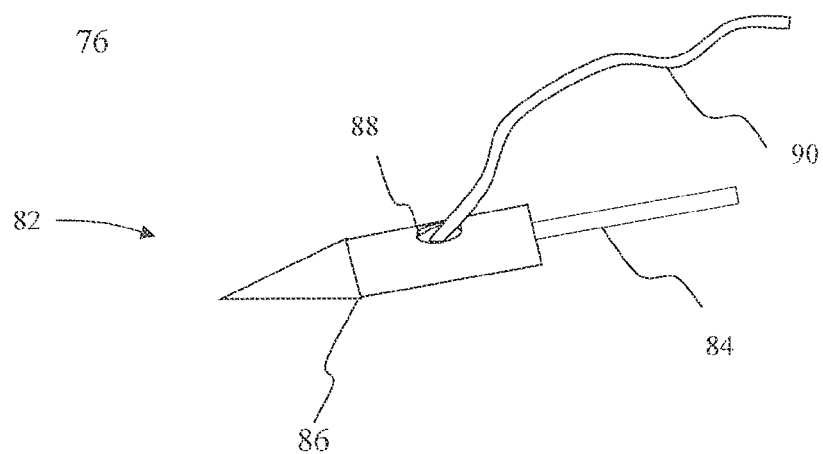
FIG. 9 is an illustrative view of a needle assembly for use with an endoscopic suturing device according to another embodiment of the present invention.

FIG. 7 illustrates needle assembly 44 which comprises a needle body 74, a needle tip 76 and suture 46. The suture 46 may be formed of any materials commonly available for surgical suture such as nylon, polyolefins, PLA, PGA, stainless steel, nitinol and others. FIG. 8 shows a detailed exploded view of two components of needle assembly 44. Needle tip 76 has a sharp distal end and a hollow proximal end having a suture slot 78 through the side wall. Needle body 74 has a rounded or blunt tapered proximal end 74a adapted to fit within the needle holder arm with the proximal end 74a presenting a shoulder 79 between end 74a and the remainder of the needle body 74. A distal end 74b of the needle body 74 has a suture slot 80 adapted to concentrically engage needle tip 76. Flexible suture material is positioned on the distal end of needle body 74 extending through the aligned suture slots 78 and 80. The needle tip 76 and needle body 74 are formed from suitable biomaterials and may be made from polymers such as nylon, PEEK, PLA, PGA, PLGA or metals such as stainless steel, nitinol or titanium. The components may be joined using standard joining techniques such as thermal bonding, ultrasonic welding laser welding, adhesives or mechanical crimping. FIG. 9 illustrates an alternative needle assembly 82 having a needle tail 84 and a needle tip 86. Needle tip 86 has a sharpened distal end, a suture aperture 88 and a hollow proximal end which is adapted to receive needle tail 84. Suture is positioned within the hollow end of needle tip 86 and extends through aperture 88. Needle tail 84 and suture 90 are secured in the hollow end of needle tip 86 using any of the aforementioned joining techniques. Needle tail 84 is preferably formed in a straightened shape and of a resilient material such as nitinol. When needle tail 84 is placed in a curved needle holder arm the needle tail bends and applies a force to the inner wall of the needle holder arm maintaining the needle assembly 82 securely in place.

Figure 10:
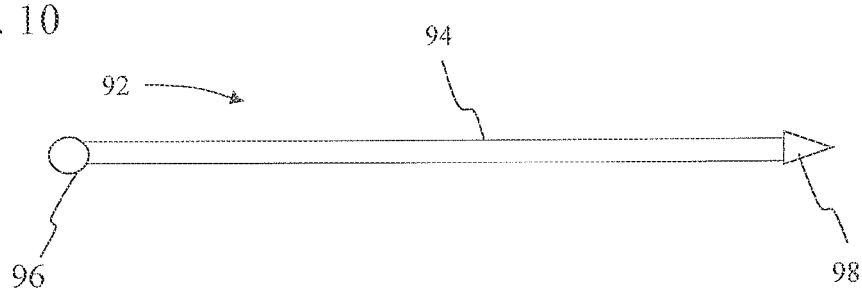
FIG. 10 is a view of an endoscopic clip for use with an endoscopic suturing system according to an embodiment of the present invention.
Figure 11:
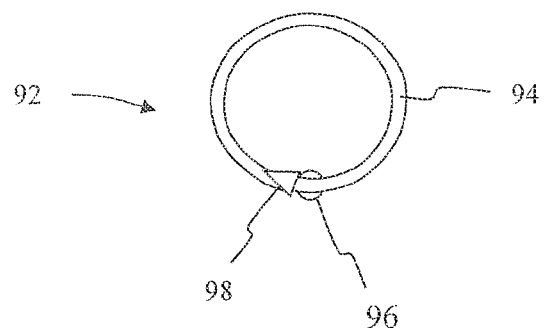
FIG. 11 is a view of the preferentially biased resilient endoscopic clip of FIG. 10 when unconstrained.
Figure 12:
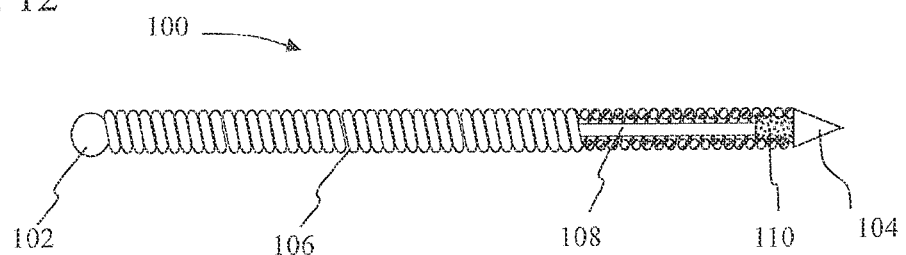
FIG. 12 is a view of an endoscopic clip for use with an endoscopic suturing system according to another embodiment of the present invention.
Figure 13:
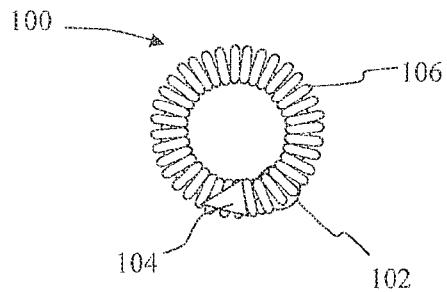
FIG. 13 is a view of the preferentially biased resilient endoscopic clip of FIG. 12 when unconstrained.
Figure 13A:
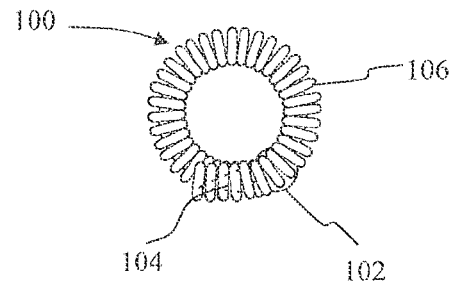
FIG. 13A is a view of the preferentially biased resilient modified endoscopic clip of FIG. 13 when unconstrained and having a coil that extends over the sharp tip.

FIG. 10 through FIG. 13A illustrate alternate versions of needle assemblies for use in closing tissue defects. FIG. 10 shows a needle clip 92 in a straightened configuration having a body portion 94 a proximal beaded end 96 and a piercing tip 98. The needle clip 92 is preferably formed of nitinol or other resilient material and biased into a generally circular shape. Needle clip 92 may be constrained in a generally straightened configuration but when unconstrained transitions to its biased generally circular configuration as shown in FIG. 11. FIG. 12 shows an alternate needle clip 100 having a proximal bead 102, a piercing tip 104, an outer coil covering 106, and a body portion 108 connecting the proximal and distal ends. The needle clip 100 also includes a securing member 110 to fixedly attach at least a portion of coil 106 to body portion 108. The needle clip 100 is preferably comprised of nitinol or other resilient material and is biased into a generally circular shape. Needle clip 100 may be constrained in a generally straightened configuration but when unconstrained transitions to its biased generally circular configuration as shown in FIG. 13. The coil 106 may be formed of suitable biomaterials such as polymers of nylon, polyester, PEEK, PLA, PGA, PLGA or metals such as stainless steel, nitinol, titanium or platinum. The coil 106 provides increased surface area for tissue in growth and encapsulation as well as distributing the force placed on tissue when closing a tissue defect. FIG. 13A shows a needle clip 100 in which the coil 106 extends over the sharp piercing tip thereby shielding the tip from inadvertent damage to surrounding tissue.

Figure 14:
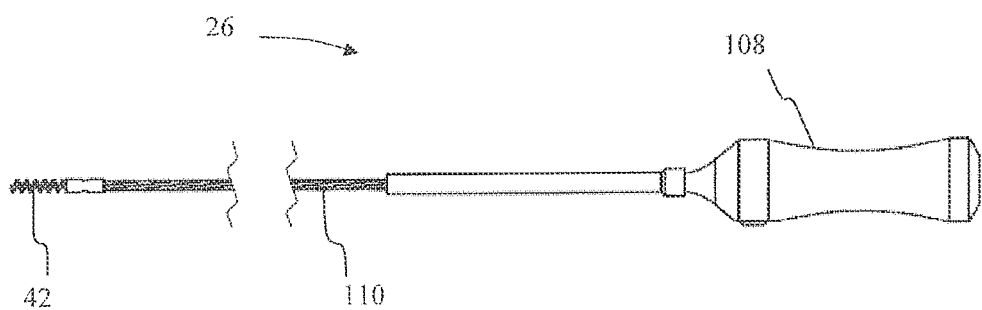
FIG. 14 is a view of the helical tissue grasper.
Figure 15:
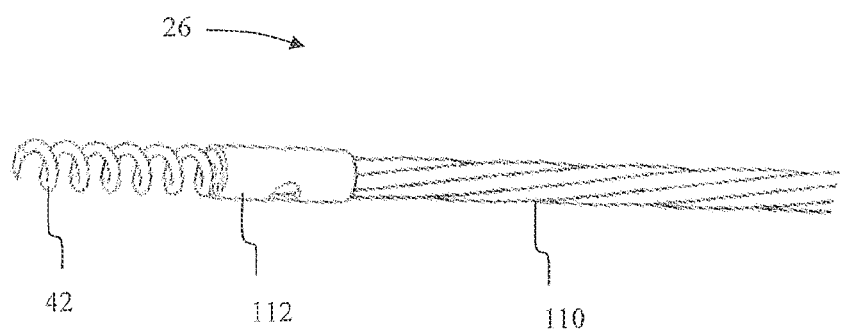
FIG. 15 is an enlarged view of the distal end of the helical tissue grasper.

FIG. 14 shows the tissue grasper 26 which has a proximal handle 109, an elongate shaft member 111 and a helical tip 42. Shaft member 111 is formed of a wire or multi-stranded cable or any torque transmitting configuration that provides flexibility which does not impede the steering capabilities of the endoscope. FIG. 15 shows an enlarged view of the distal end of tissue grasper 26. Shaft member 111 is coupled to helical tip 42 by tip coupling member 112. Tip coupling member 112 may be fixedly joined to helical tip 42 and shaft member 111 by any of the aforementioned joining techniques.

Figure 16:
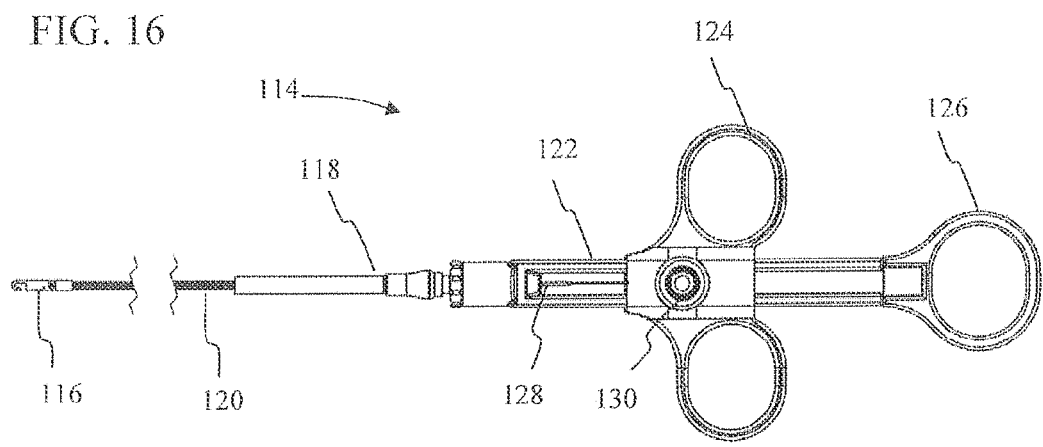
FIG. 16 is a top view of a cinch device and cinch delivery device.
Figure 17:
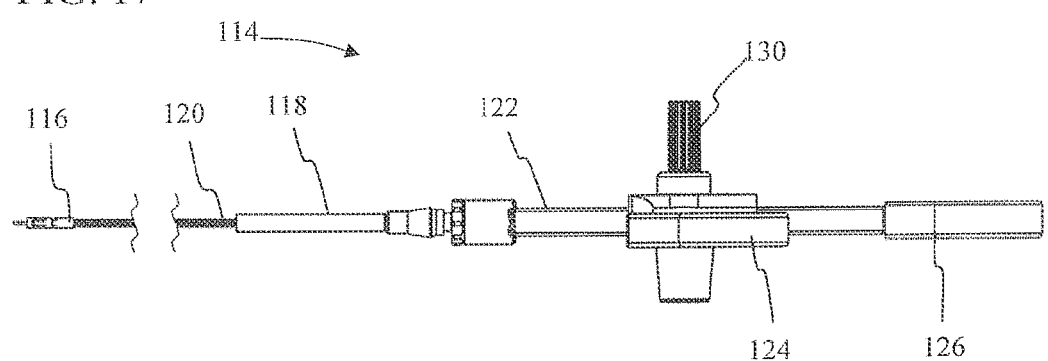
FIG. 17 is a side view of a cinch device and cinch delivery device.

FIG. 16 and FIG. 17 show a cinch deployment system 114 for securing suture placed at a tissue defect site. The cinch deployment system 114 comprises a cinch assembly 116 and a cinch delivery device 118. The cinch delivery device 118 has an elongate flexible tubular shaft 120 which is removably coupled at its distal end to cinch assembly 116 and fixedly attached at its proximal end to handle member 122. Handle member 122 includes a slidable finger ring assembly 124 and a thumb ring 126. Slidably disposed within the lumen of tubular shaft 120 is push rod 128. Push rod 128 extends from the distal end of tubular shaft 120 to the proximal end of tubular shaft 120 and is coupled to the slidable finger ring assembly 124 with fixation screw 130, such that movement of the finger ring assembly relative to the thumb ring 126 causes the axial movement of push rod 128 within the lumen of tubular shaft 120. A partially exploded view of the distal end of the cinch deployment system 114 is shown in FIG. 18. As depicted, push rod 128 extends from tubular shaft 120 and through latch assembly 129. Latch assembly 129 is fixedly attached to tubular shaft 120 and has two latch arms 132 with latch tabs 134 at their distal ends. Latch arms 132 are biased inwardly towards the central longitudinal axis of tubular shaft 120. Latch assembly 129 is positioned within the lumen of a latch coupling 136 and is fixedly secured. Latch coupling 136 is configured at its distal end to engage with the proximal end of cinch 116 such that the latch arms 132 extend within the proximal lumen of cinch 116 and when push rod 128 is positioned within latch assembly 129 the latch arms 132 are forced outwardly such that the latch tabs 134 locking engage the cinch tab apertures 138. When push rod 128 is axially retracted from latch assembly 129 the latch arms 132 move inwardly towards their biased configuration causing latch tabs 134 to release their locking engagement with cinch tab apertures 138 to thereby release the cinch assembly 116. FIG. 19 illustrates the cinch assembly 116 in an open configuration. Cinch assembly 116 has a tubular housing member 139 having cinch tab apertures 138 located at its proximal end and a suture hook 140 fixedly attached at its distal end. A securing clasp 142 is slidably positioned within the lumen of housing member 139. A retention tab 144 is preferably formed from the wall of housing member 139 and biased inwardly towards the central axis at of housing member 139 at its distal end. When suture has been captured by suture hook 140 the suture may be secured within cinch assembly 116 by advancing push rod 128 such that securing clasp 142 extends from housing member 139 and engages suture hook 140. With securing clasp 142 in extended configuration retention tab 144 moves to its inwardly biased configuration restricting the proximal movement of the securing clasp 142 thereby fixing the suture in place.

Figure 21:
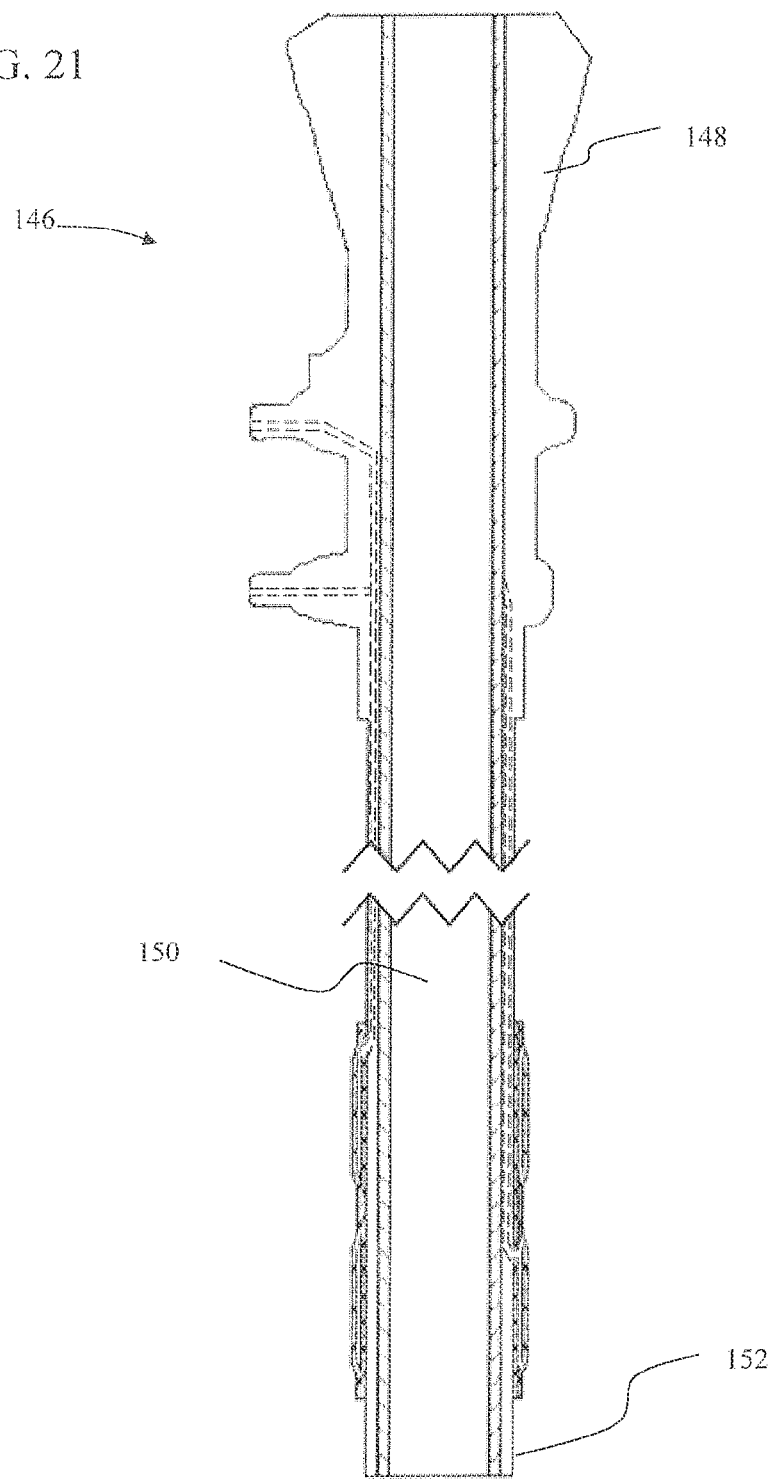
FIG. 21 is a sectional view of an endoscopic guide tube.
Figure 22:
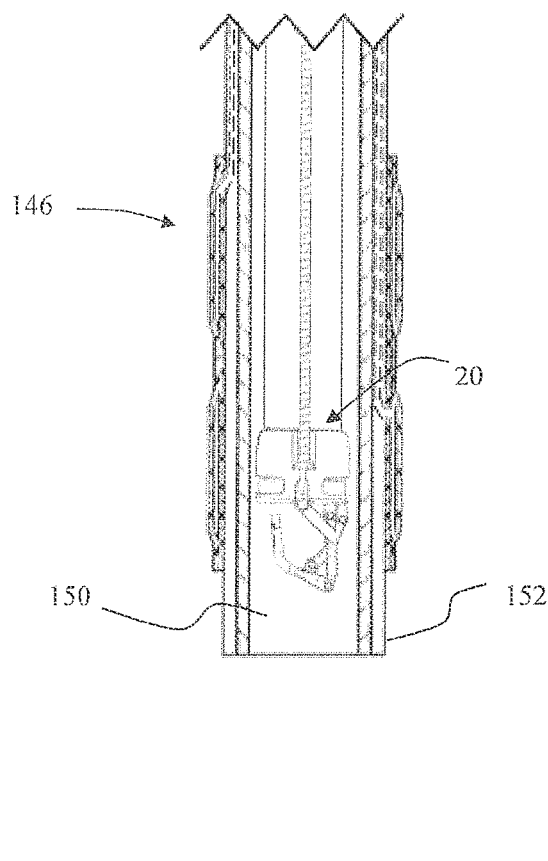
FIG. 22 is a partial sectional view of an endoscopic suturing system disposed within the lumen of an endoscopic guide tube.
Figure 23:
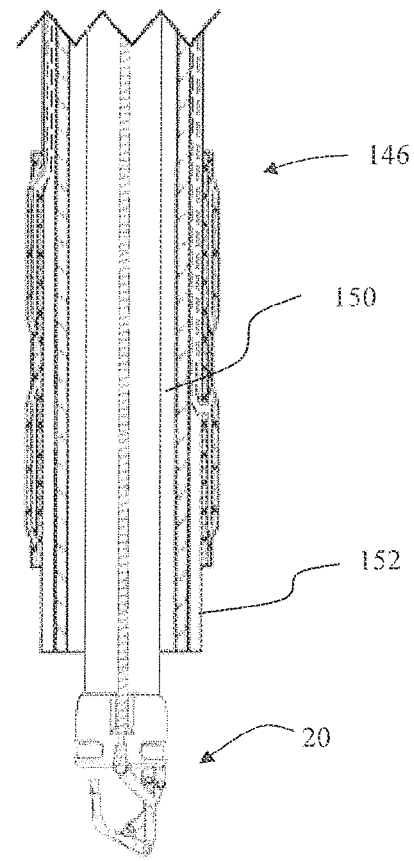
FIG. 23 is a partial sectional view of an endoscopic suturing system extending from the distal end of an endoscopic guide tube.

FIG. 21 illustrates a guide tube 146 for use in an endoscopic procedure. Guide tube 146 has a proximal end 148 including a lumen 150 that extends to the distal end 152. Generally a guide tube 146 is positioned in a patient to provide a conduit to a desired location while protecting the surrounding tissue from inadvertent damage. As shown in FIG. 22 and FIG. 23 show a guide tube 146 with an endoscopic suturing device 20 positioned in the lumen 150. Once the guide tube 146 is positioned at a desired treatment location within the body the distal end of the endoscopic suturing device 20 may be extended beyond the distal end of the guide tube 146.

Figure 24:
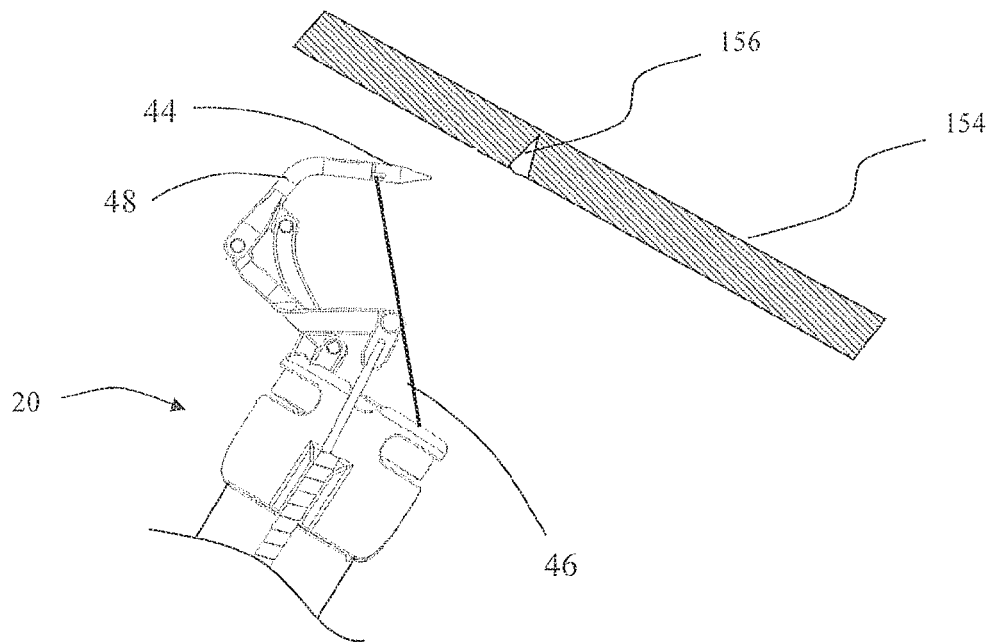
Figure 25:
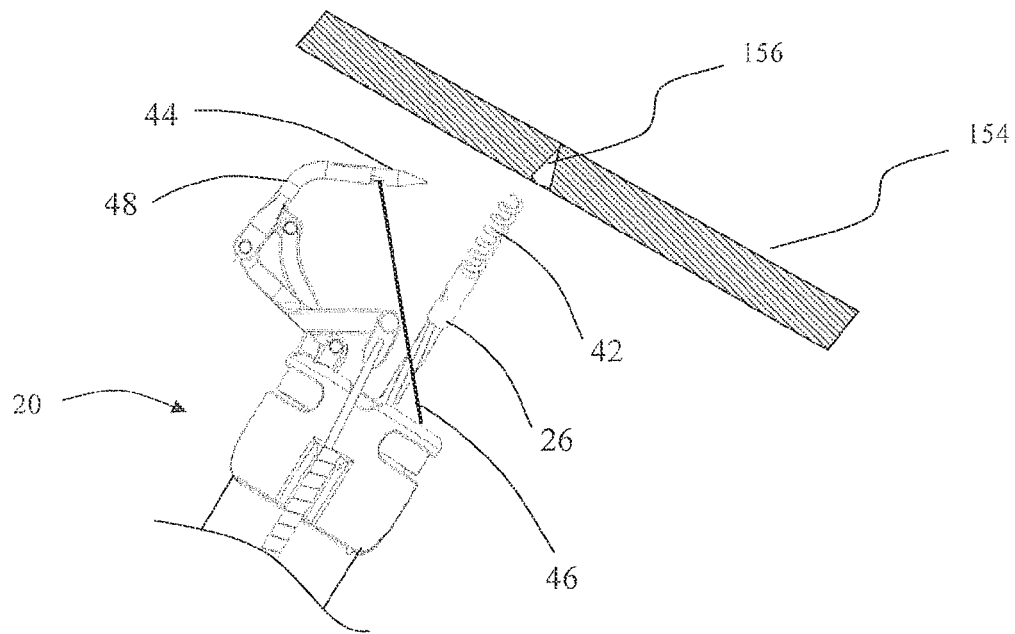
Figure 26:
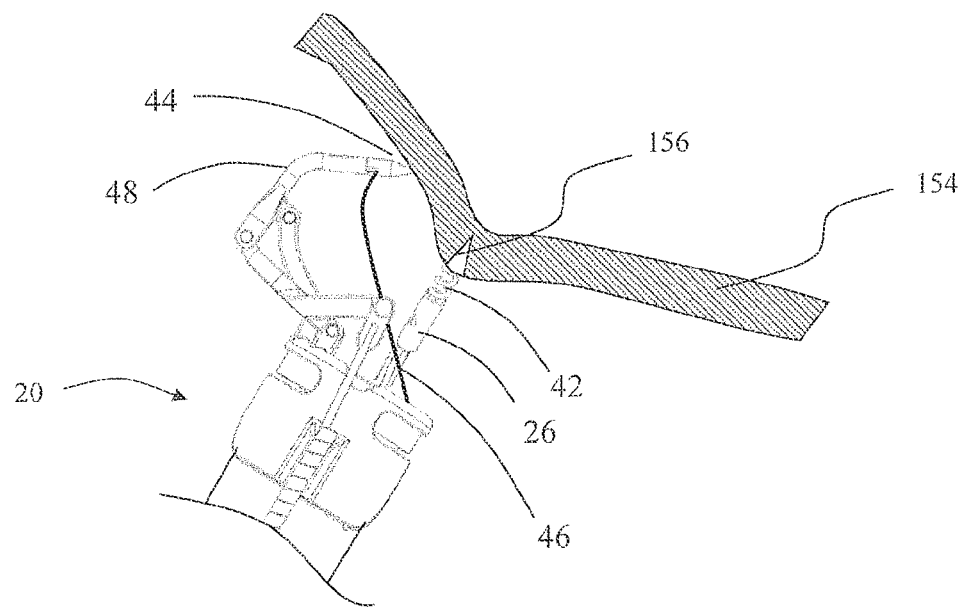
Figure 27:
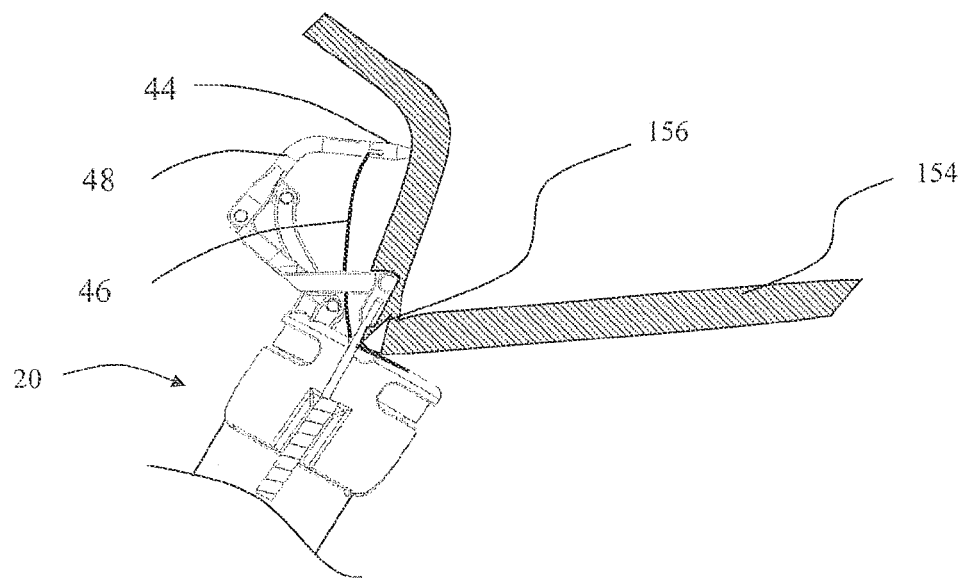
Figure 28:
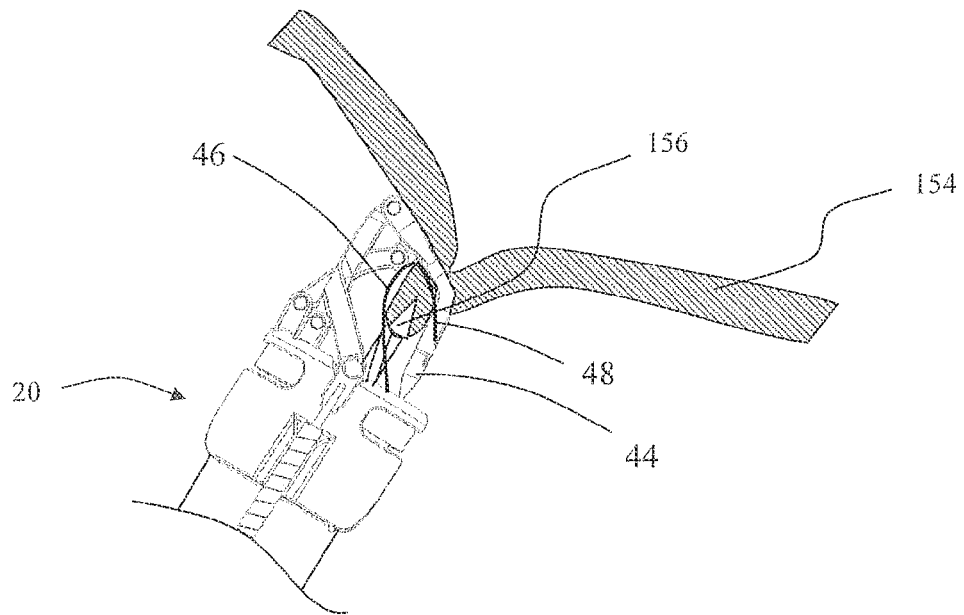
Figure 29:
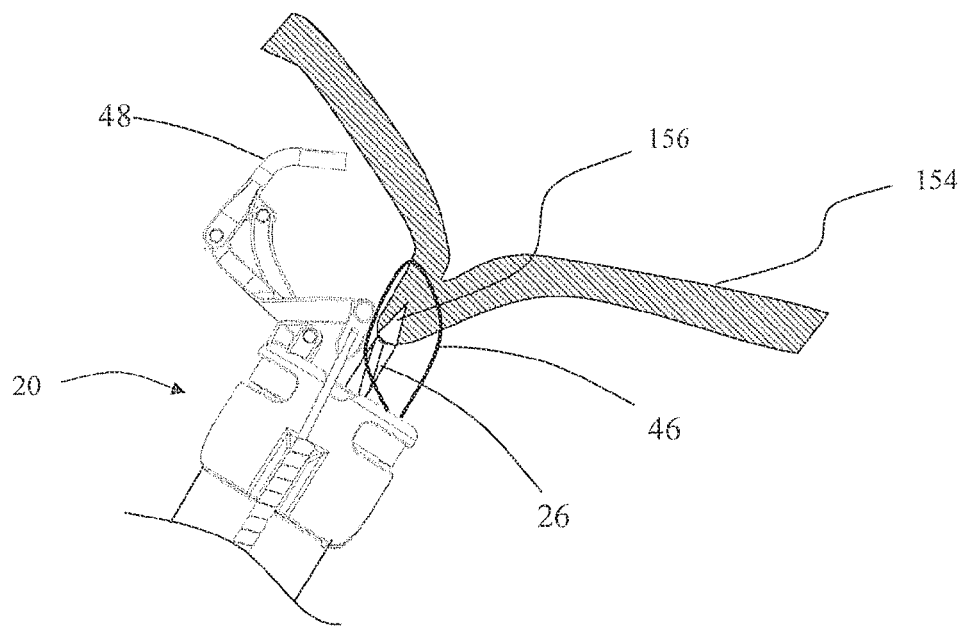
Figure 30:
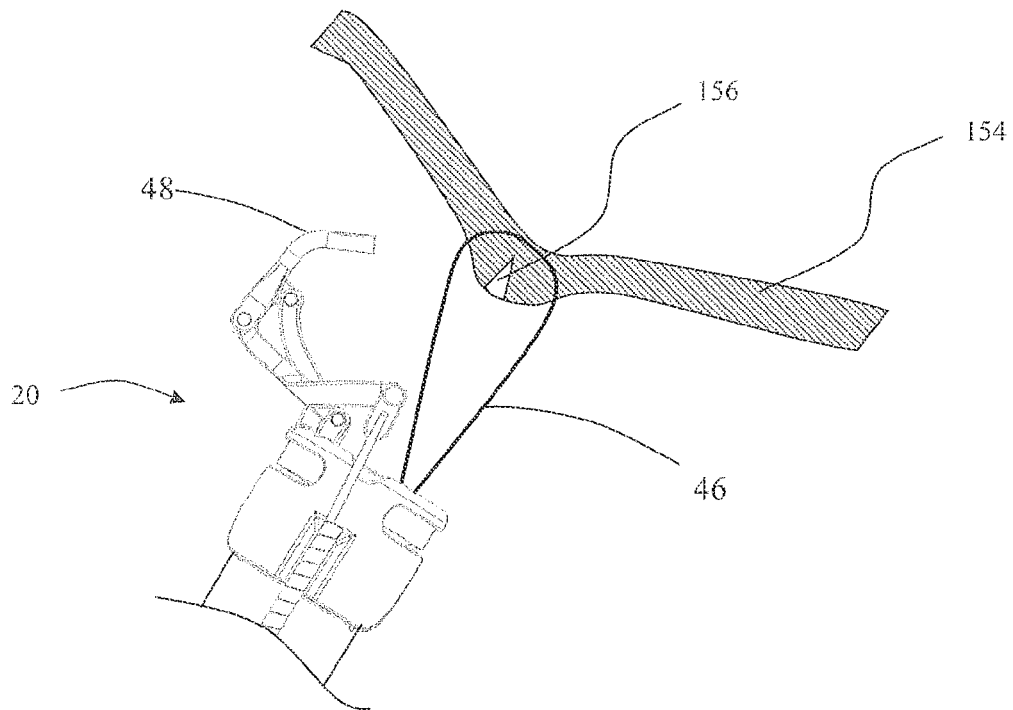
Figure 31:
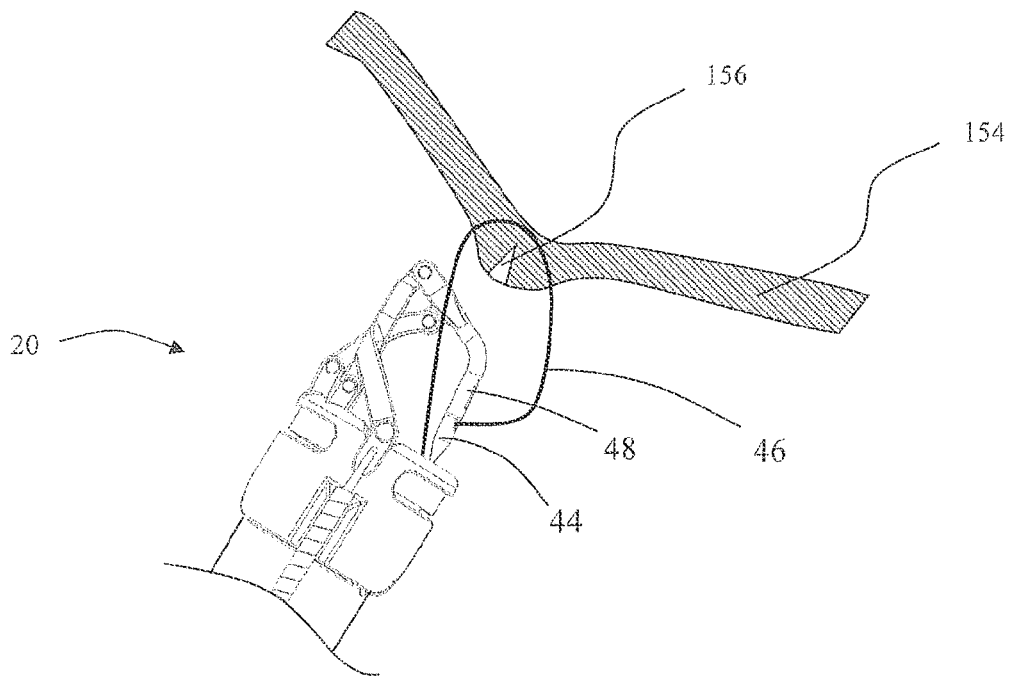
Figure 32:
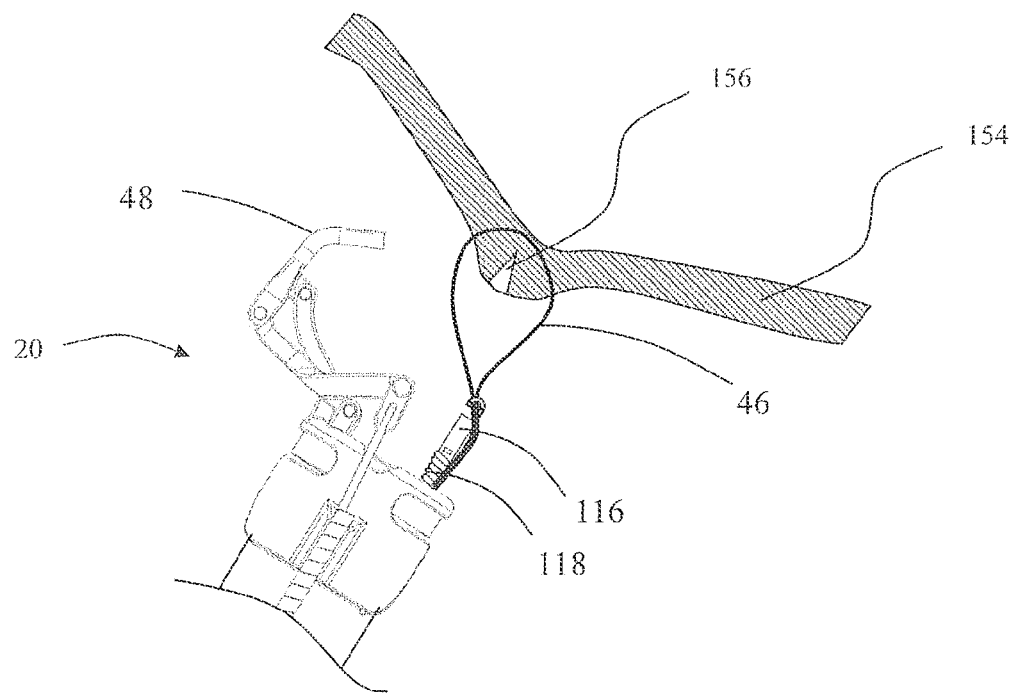
Figure 33:
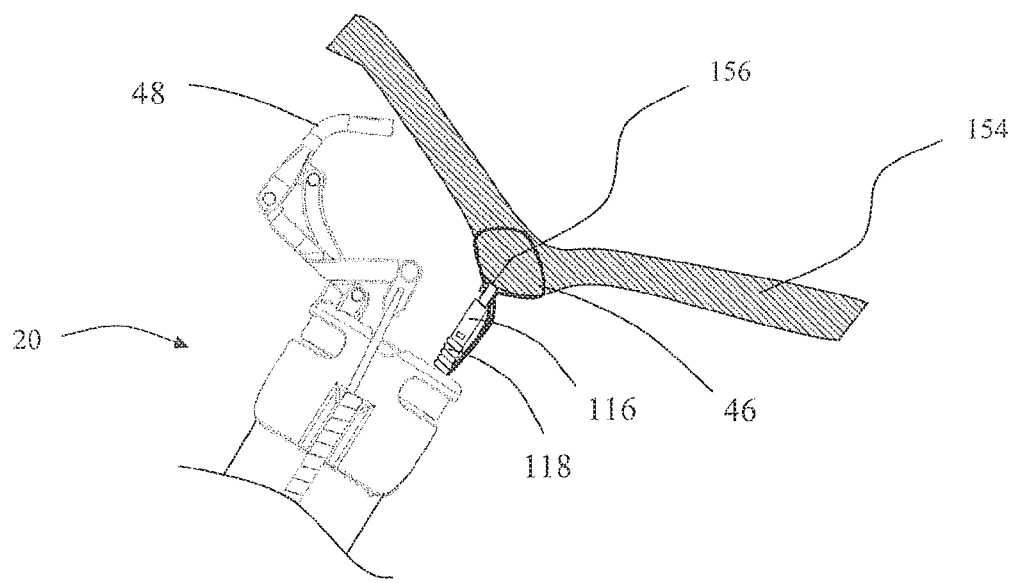
Figure 34:
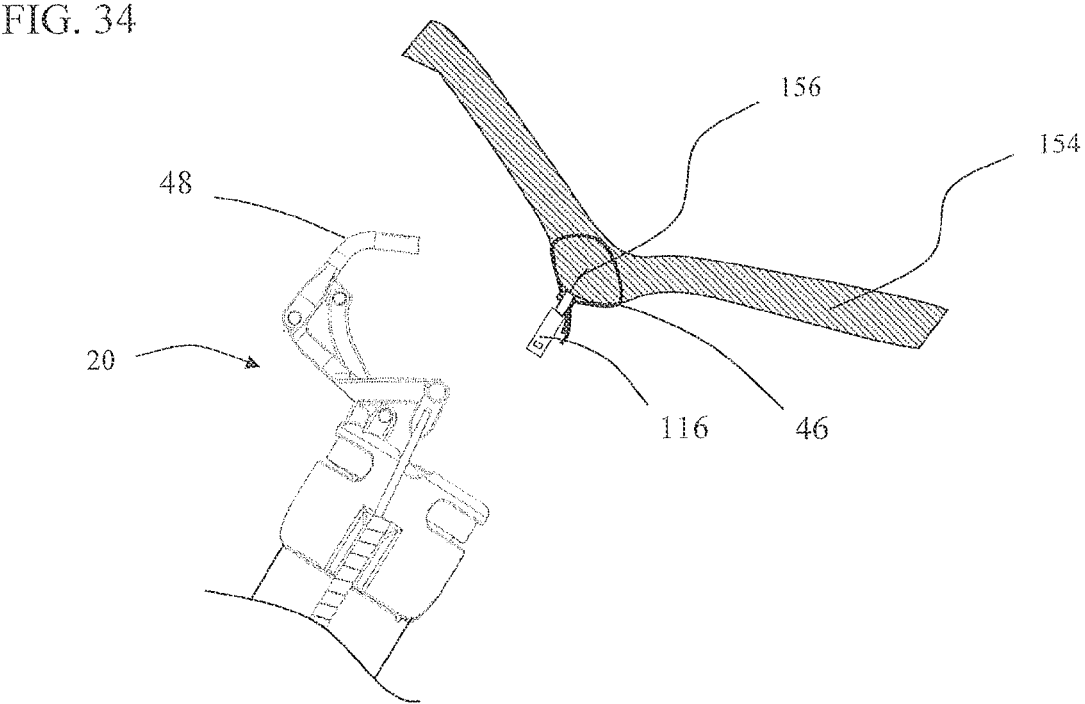

FIG. 24 through FIG. 34 depicts a method of performing a suturing operation using an endoscopic suturing device 20 of the present invention. As shown in FIG. 24, the endoscopic suturing device 20 is positioned adjacent tissue 154 which has a tissue defect 156 to be closed. The endoscopic suturing device 20 is in an open configuration. FIG. 25 shows the tissue grasper 26 extended from the endoscope instrument channel such that helical tip 42 is adjacent tissue defect 156. Rotation of the tissue grasper 26 causes the helical tip 42 to securely engage the tissue 154 adjacent to the tissue defect 156. The tissue 154 may be brought closer to the endoscope by slightly retracting the tissue grasper 26 into the instrument channel of the endoscope as shown in FIG. 26. The degree of tissue retraction correlates to the size and location of the stitch. For instance, to have a larger amount of tissue sutured, the tissue 154 may be brought into contact with the endoscope by the tissue grasper as shown in FIG. 27. The needle holder arm 48 is actuated to move to a closed position causing the needle assembly 44 to pierce tissue 154. The suture 46 is pulled through the tissue as shown in FIG. 28. The control over the amount of tissue retracted allows the physician the ability to perform a partial thickness stitch within the wall of a tissue or a full thickness stitch which extends through a wall of tissue. The needle capture device captures the needle assembly 44 by gripping it at shoulder 79 (FIG. 7) and removes it from the needle holder arm 48 (not shown). FIG. 29 shows the needle holder arm 48 moved to an open configuration and removed from tissue 154. Suture 46 remains through the tissue. FIG. 30 shows the lengthening of the suture 46 through the tissue 154 by retracting the endoscopic suturing device 20 while retaining the needle assembly 44 within the needle capture device. FIG. 31 shows the needle holder arm 48 moved to a closed configuration and needle assembly 44 reinserted into the needle holder arm 48 by advancing the needle capture device if the physician wishes to make another stitch. If the physician does not wish to make another stitch, the needle assembly with suture can be retracted through the endoscope channel and with both ends of the suture, a knot can be tied and pushed down the endoscope channel to the treatment site to secure the tissue. Alternatively, the suture can be secured using a cinch deployment system. As shown in FIG. 32 a cinch assembly 116 and a cinch delivery device 118 may be used to capture the suture 46. The suture may be pulled tight to securely close the tissue defect 156. Once the tissue defect 156 is sufficiently closed the cinch assembly 116 may be moved to a closed configuration, thereby securing the suture 46 as shown in FIG. 33. The cinch delivery device 118 can release the cinch assembly 116 as shown in FIG. 34 and the suture 46 may then be cut using any standard cutting means such as scissors. It is contemplated that the cinch assembly may incorporate cutting means after securing the suture.

Figure 35:
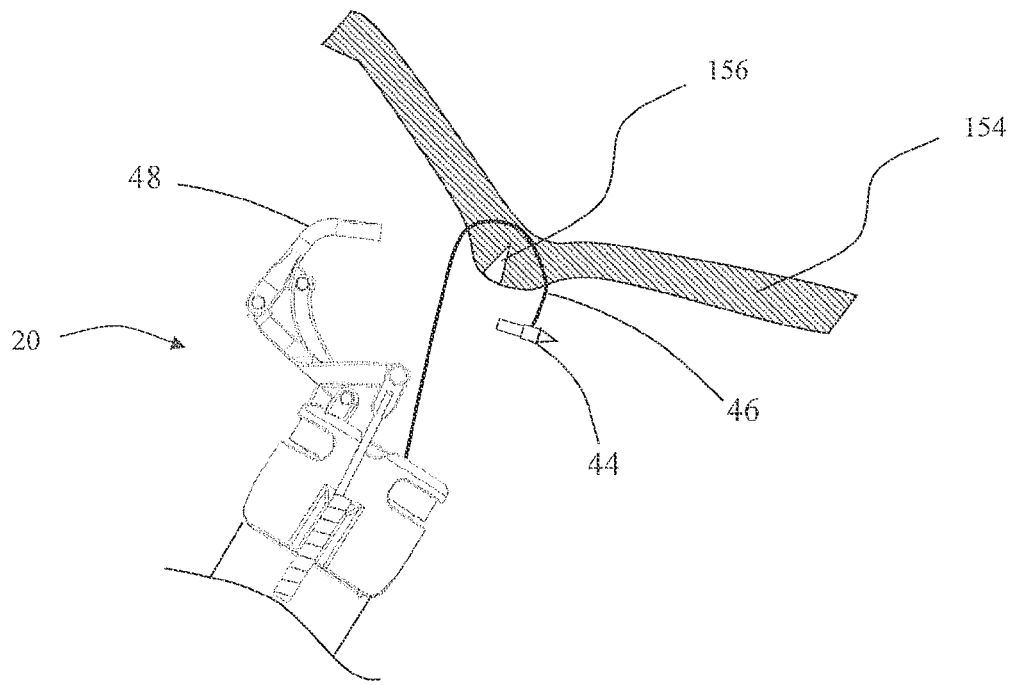
Figure 36:
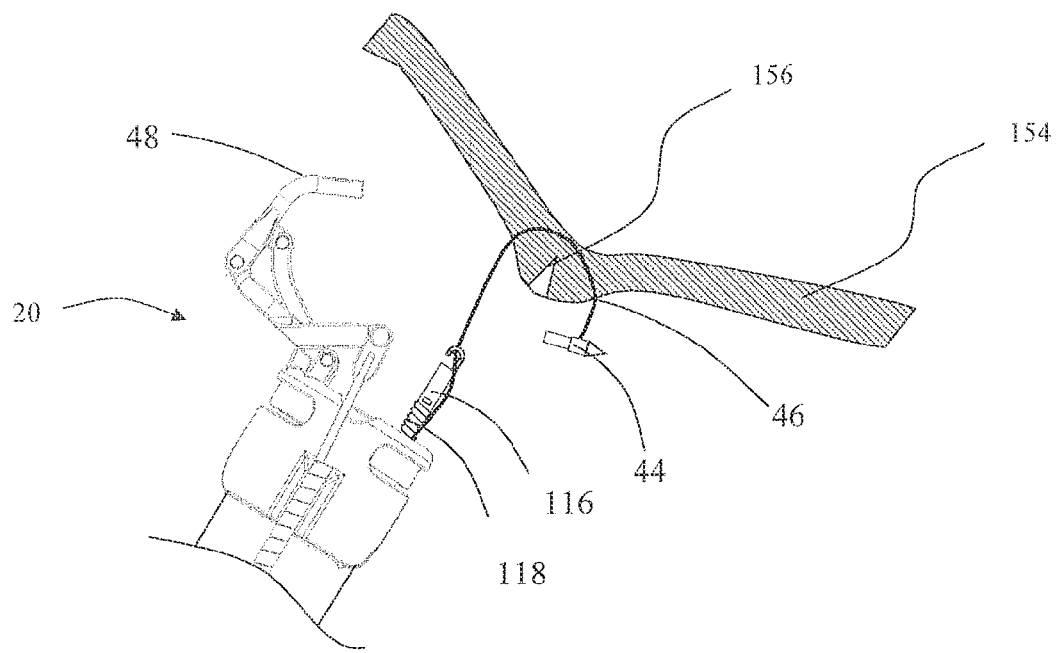
Figure 37:
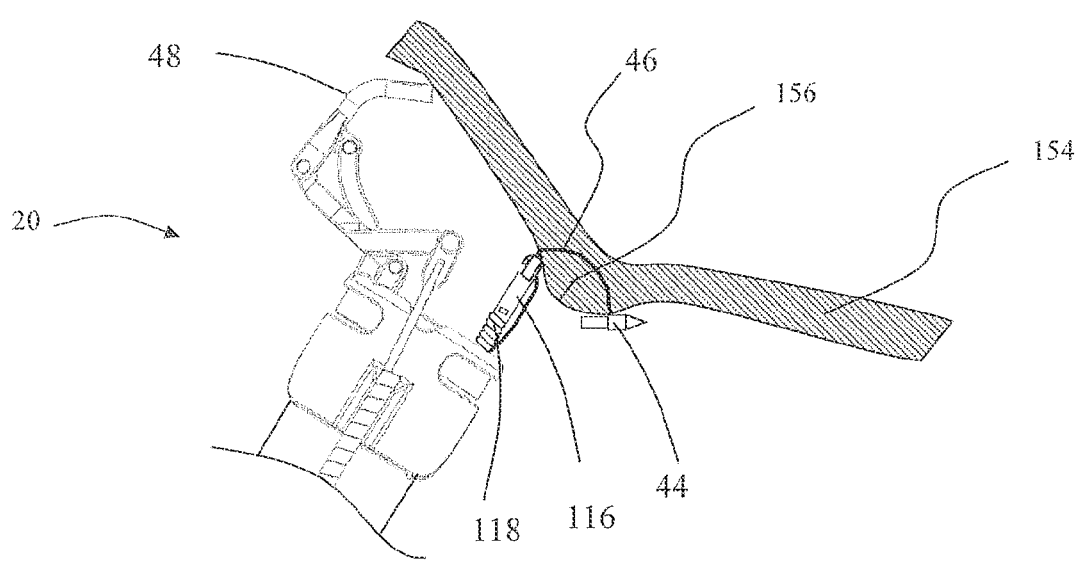
Figure 38:
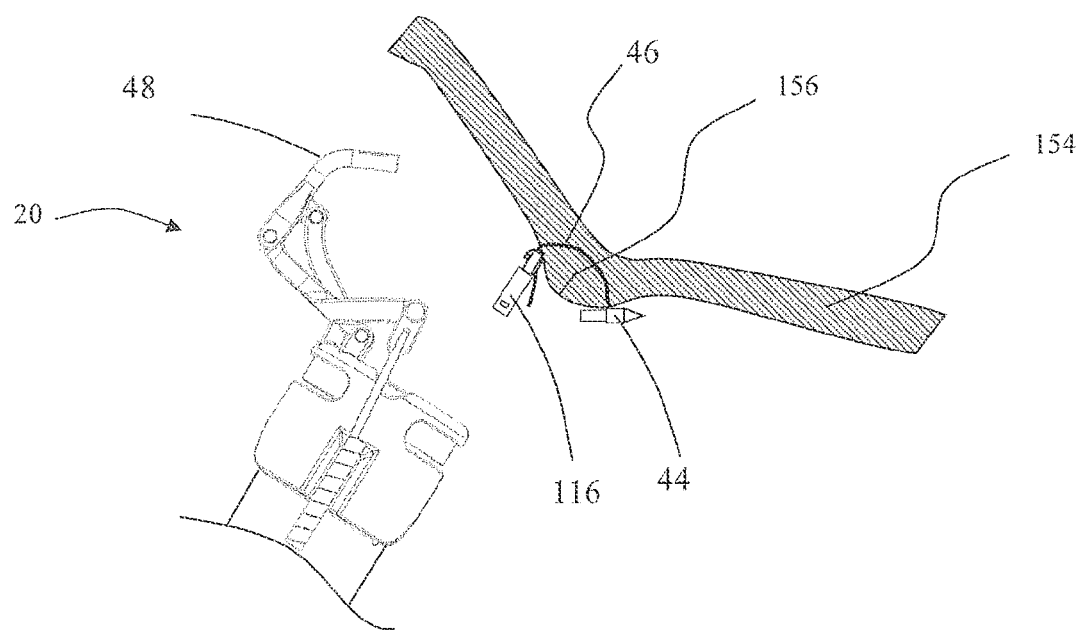

FIG. 35 through FIG. 38 shows another method of closing a tissue defect and securing the suture. FIG. 35 shows the endoscopic suturing device 20 having delivered a needle assembly 44 (shown schematically) and suture 46 through tissue 154 adjacent a tissue defect 156 where the needle assembly 44 is resting adjacent the surface of tissue 154. FIG. 36 shows a cinch deployment system having a cinch assembly 116 and a cinch delivery device 118 that has grasped a portion of suture 46. The suture is pulled tight to close the tissue defect 156 while the needle assembly prevents the end of suture 46 from pulling through the tissue 154. Once the tissue defect 156 is sufficiently closed the cinch assembly 116 may be moved to a closed configuration, thereby securing the suture 46 as shown in FIG. 37. The cinch delivery device 118 can release the cinch assembly 116 as shown in FIG. 38 and the suture 46 may then be cut using any standard cutting means such as scissors.

Figure 39:
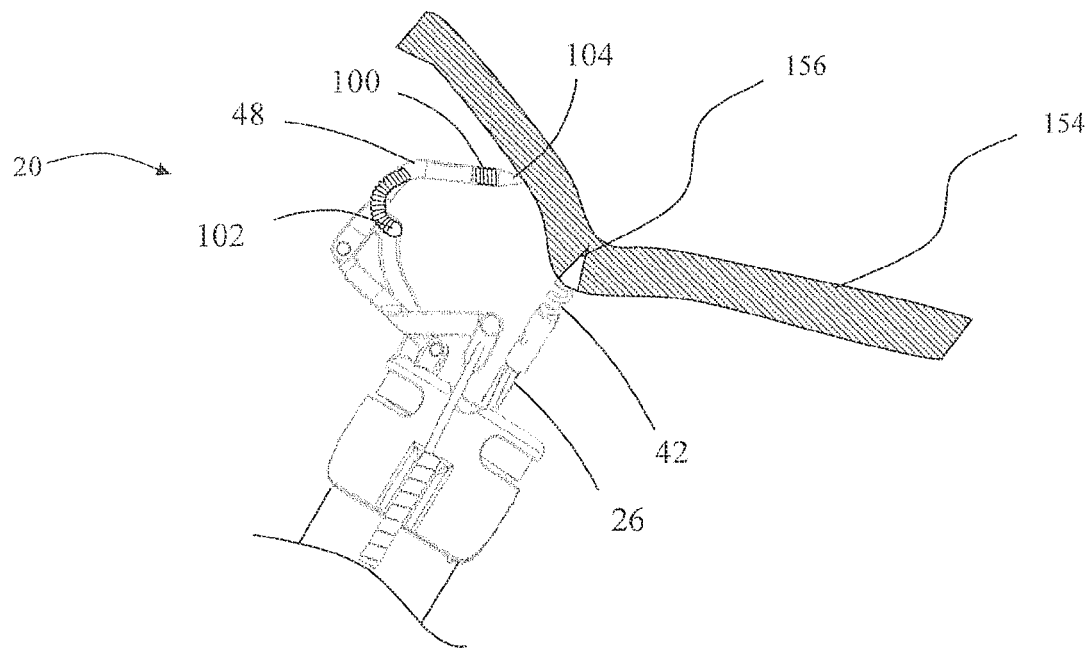
Figure 40:
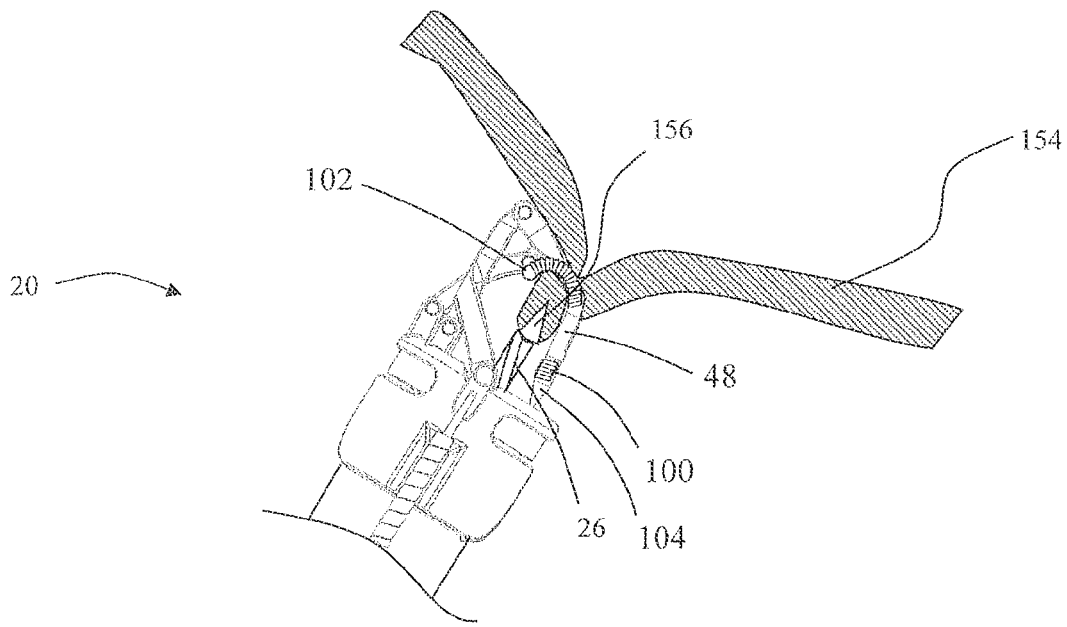
Figure 41:
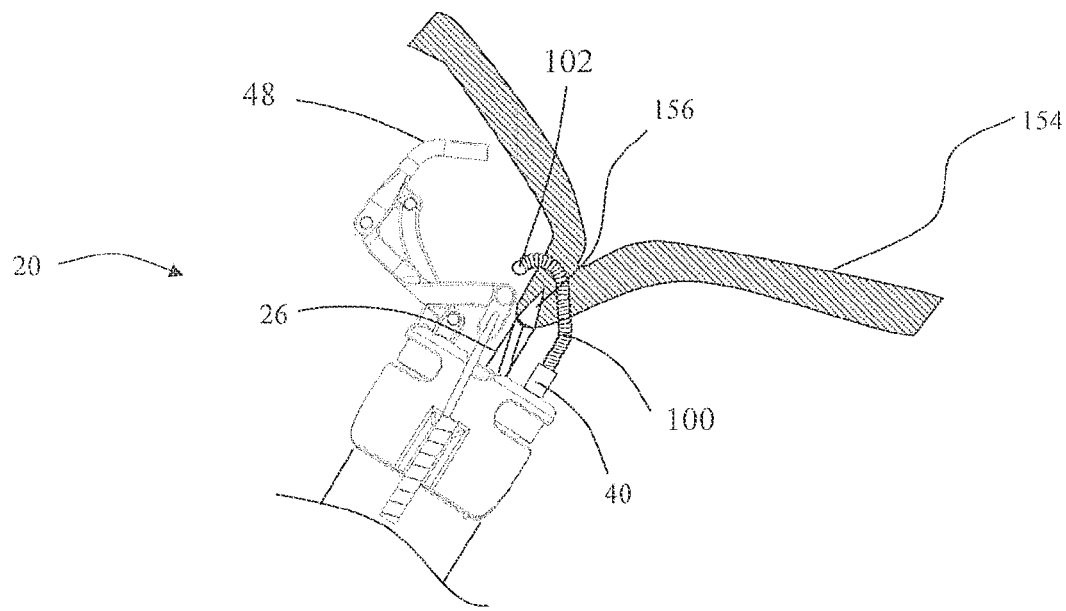
Figure 42:
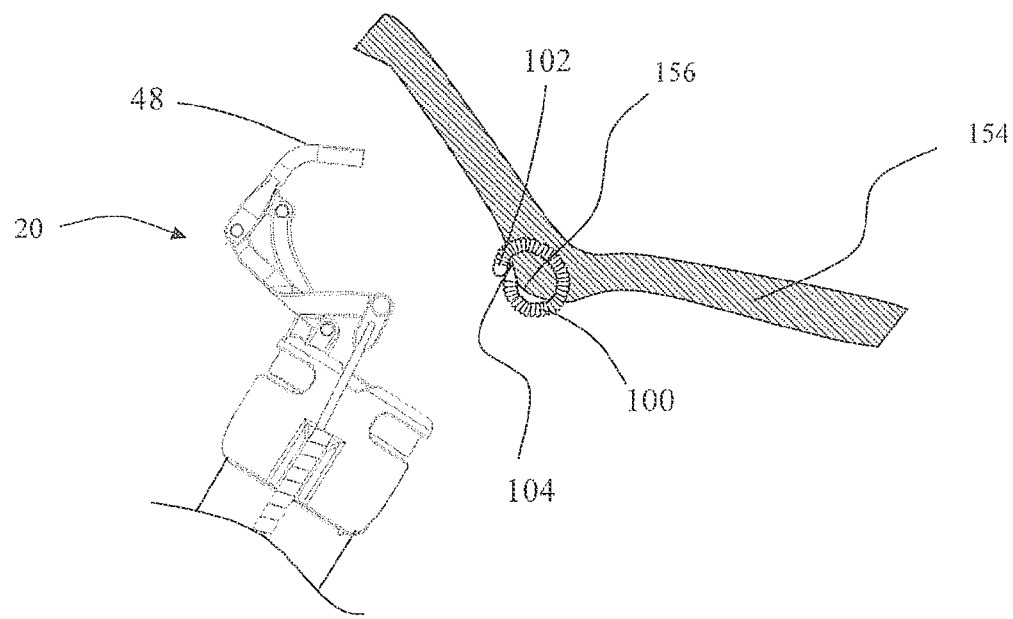

FIG. 39 through FIG. 42 shows still another method securely closing a tissue defect. FIG. 39 shows an endoscopic suturing device 20 having an open configuration and a needle clip 100 having a proximal bead 102 and a piercing tip 104 positioned in needle holder arm 48. The helical tip 42 of the tissue grasper 26 has engaged tissue 154 adjacent to the tissue defect 156 and retracted the tissue towards the endoscope. FIG. 40 shows the needle holder arm 48 in a closed configuration positioned through the tissue with the piercing tip 104 of needle clip 100 having pierced and exited the tissue. FIG. 41 shows the needle capture device grasping the piercing tip of the needle clip 100 with the needle holder arm 48 in an open configuration and removed from tissue 154. The proximal bead 102 of needle clip 100 is positioned adjacent the tissue site initially pierced by the piercing tip. FIG. 42 shows the release of tissue 154 from the tissue grasper and the resilient needle clip 100 taking its pre-biased generally circular shape thereby closing the tissue defect 156. As can be appreciated, the application of a tissue sealant or adhesive may be used to aid in the closing the tissue defect.

Figure 43:
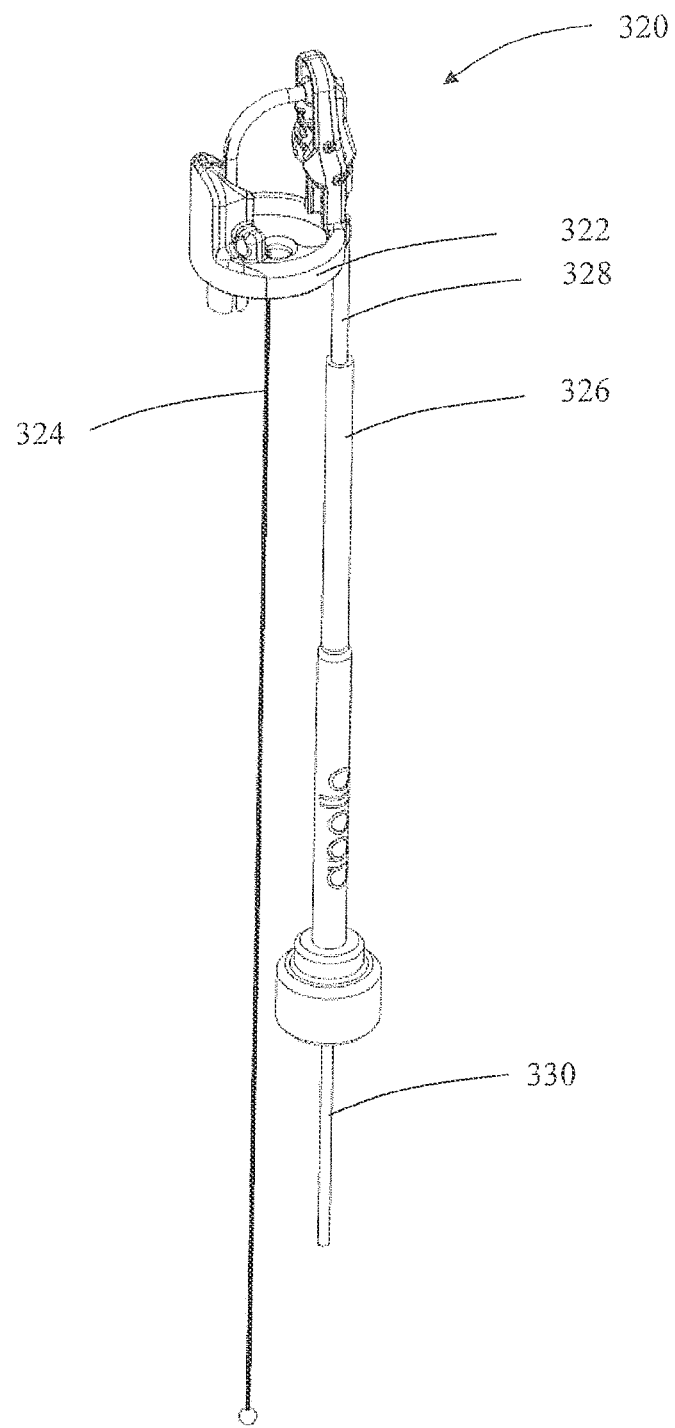
FIG. 43 is an illustrative view showing an endoscopic suturing system with a channel lock member according to another embodiment of the present invention.
Figure 44:
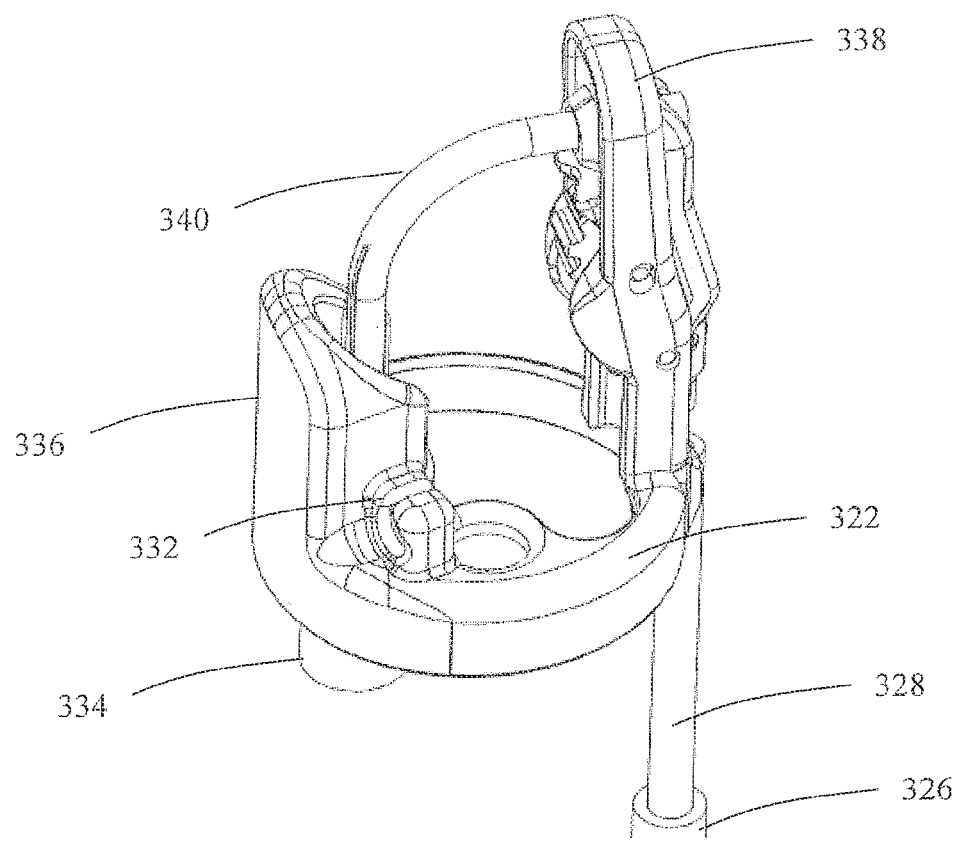
FIG. 44 is a perspective enlarged view of the cap assembly of an endoscopic suturing system according to an embodiment of the present invention where the actuating arm of the suturing device is closed.
Figure 45:
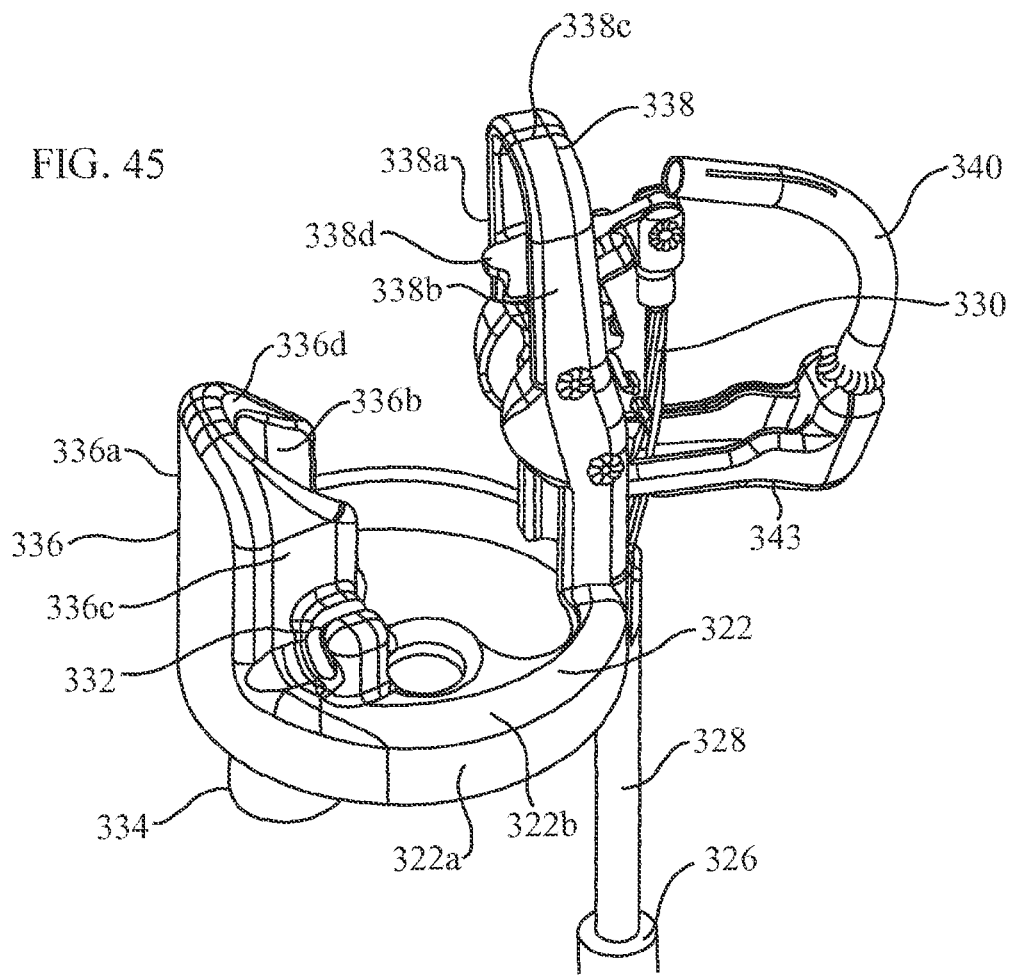
FIG. 45 is a perspective enlarged view of the cap assembly of an endoscopic suturing system according to an embodiment of the present invention where the actuating arm of the suturing device is open.

FIG. 43 shows an endoscopic suturing device 320 according to another embodiment of the present invention. Endoscopic suturing device 320 includes a cap assembly 322 which is adapted to engage with the distal end of an endoscope, an elongate channel lock member 324 which is optionally removable from cap assembly 322, an outer sheath 326, an inner sheath 328 and an elongate flexible transmission member 330. As seen in FIG. 44, cap assembly 322 further includes a fixedly attached channel lock receiver 332, an endoscope channel insert guide 334, an elongate tissue guard 336, an elongate needle guard 338 which extends distally from the base of the cap assembly and houses the mechanical assembly that provides rotational motion for needle holder arm 340 as shown in FIG. 44. Channel insert guide 334 is a tubular projection from cap assembly 322 and is adapted to be positioned within the lumen of an endoscope instrument channel at its distal end. The elongate flexible channel lock member 324 extends from the channel lock receiver 332 through an instrument channel and is secured at the proximal end of the instrument channel. The channel lock member 324 ensures that the cap assembly 322 does not inadvertently disengage from the distal end of the endoscope. Preferably channel lock member 324 takes the form of a small diameter single or multi stranded wire or cable formed primarily of metals or polymers. Additionally the small diameter of channel lock 324 allows room for other instruments to be positioned within the instrument channel of the endoscope. FIGS. 44 and 45 respectively show the cap assembly 322 in a needle arm 340 closed configuration and a needle arm open configuration.

For purposes of example only, and not by way of limitation, in the shown embodiment, the cap assembly 322 has a cap or ring element 322a having an inner diameter of approximately 13.5 mm, an outer diameter of approximately 14.2 mm, a height of a little over 2 mm, and a portion 322b having a rim width of between 1 mm and 2 mm.

For purposes of example only, and not by way of limitation, in the shown embodiment, the elongate tissue guard 336 circumscribes approximately 50.degree. of the ring 322a on its outside surface 336a and extends vertically approximately 9 mm over the top of the ring element 322a at its middle portion. The inside surface 336b of the elongate tissue guard 336 is generally semicircular (thereby helping define side walls 336d) and defines an approximately 4 mm-5 mm opening which extends above a smaller ring 322c (see FIG. 48) of the cap assembly and above a channel of the endoscope into which the needle capture device (described hereinafter with reference to FIGS. 55-57) is to be located. This channel may be the same channel of the endoscope into which the channel insert guide 334 is inserted as described hereinafter. The top surface 336d of the elongate tissue guard 336 is angled at an approximately 45.degree. angle. With the provided arrangement, and as discussed hereinafter with reference to FIGS. 63-39, the tissue guard 336 helps fold tissue for stitching and helps prevent tissue which is drawn into the cap assembly from clogging the endoscope channel and preventing stitching.

For purposes of example only, and not by way of limitation, in the shown embodiment, the elongate needle guard 338 has a height of between approximately 18 mm and 19 mm, and forms an arched opening between two arms 338a, 338b which have outside surface spaced approximately 5 mm apart from each other and inside surfaces spaced approximately 3.7 mm from each other. The arms are joined by a top arch 338c and an optional cross-member (stop) 338d located below the arch 338c. In between the arms and below cross-member 338d is a gear linkage 342 described hereinafter. In addition, the curved needle holder arm 340 is arranged such that when a needle is held in the needle holder arm 340, in a fully open position, the tip of the needle is preferably located under the arch 338c and between the arms 338a, 338b. The holder arm 340 can then rotate into a closed position through the arched opening above the gear linkage. Each arm 338a, 338b has a width of approximately 0.64 mm and a radial thickness of approximately 2.5 mm.

Figure 46:
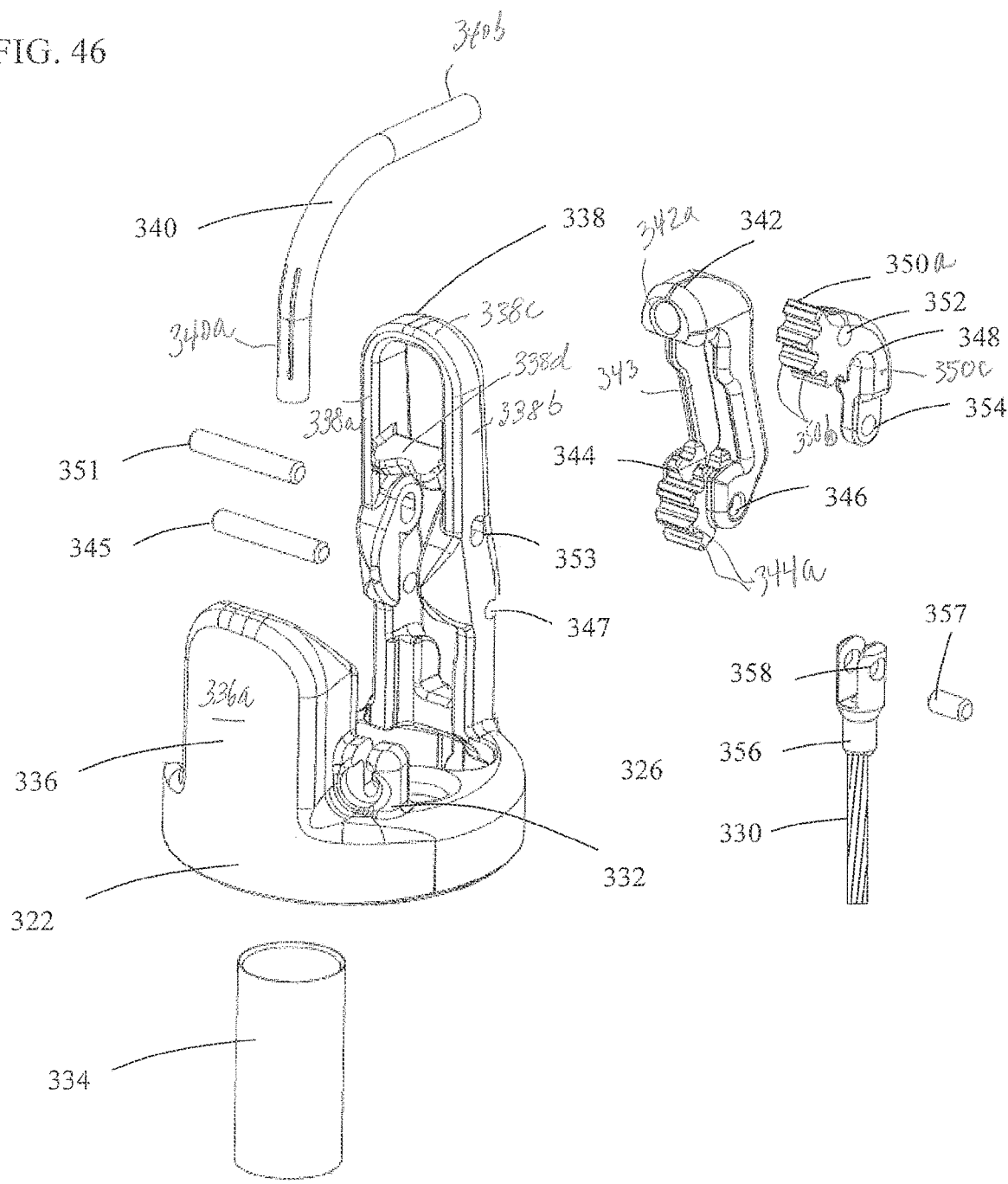
FIG. 46 is a perspective enlarged exploded view of the cap assembly of an endoscopic suturing system according to an embodiment of the present invention.
Figure 47:
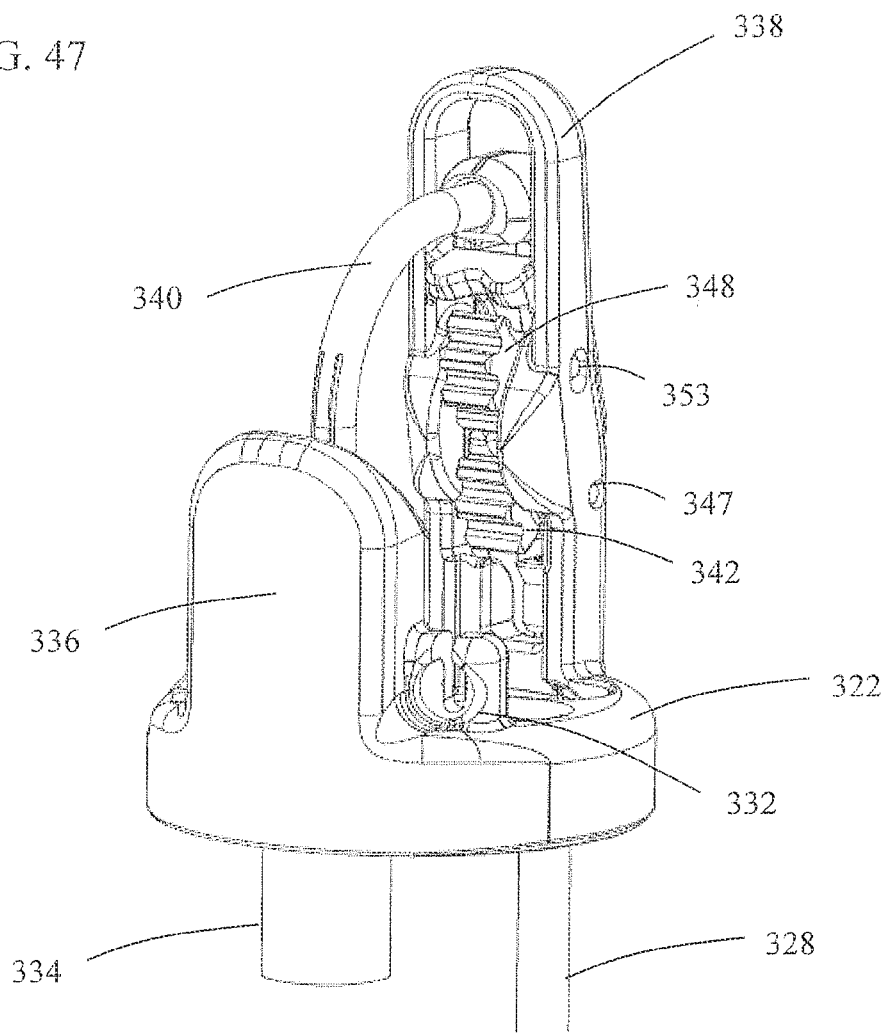
FIG. 47 is another perspective enlarged view of the cap assembly of an endoscopic suturing system according to an embodiment of the present invention where the actuating arm of the suturing device is closed.
Figure 48:
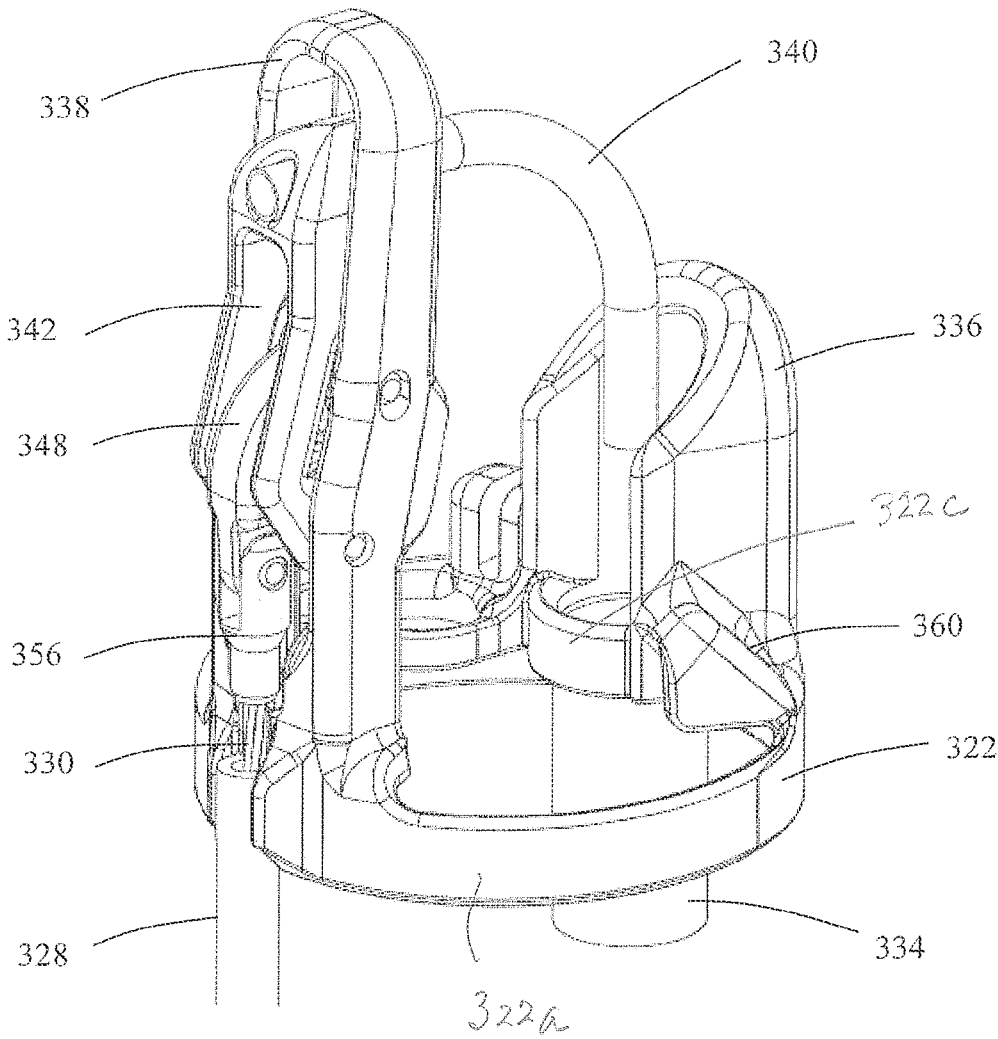
FIG. 48 is yet another perspective enlarged view of the cap assembly of an endoscopic suturing system according to an embodiment of the present invention where the actuating arm of the suturing device is closed.

FIG. 46 shows a detailed exploded view of cap assembly 322. Needle holder arm 340 includes a first end 340a which is adapted to frictionally engage a needle assembly, and a second end 340b is fixedly secured to needle arm gear link 342 (e.g., in a receiving hole 342a defined therein). By way of example only and not by way of limitation, needle holder arm 340 bends through an arc of approximately 90.degree. Gear link 342 is mounted between needle guard arms 338a, 338b and includes a gear portion 344 which is mounted using pivot pin 345 through mounting hole 346 in gear link 342 to mounting holes (first mounting locations) 347 defined in the housing (arms) of needle guard 338, and an arm or extension portion 343. Gear portion 344 includes lateral gear teeth 344a. Similarly, push member gear link 348 includes gear portion 350a with lateral gear teeth 350b which mesh with gear teeth 344a, and an arm 350c. Gear link 348 is mounted using pivot pin 351 through mounting hole 352 to mounting holes (second mounting locations) 353 defined in the housing (arms) of needle guard 338. Gear link 348 is also coupled through mounting hole 354 in arm 350c to push member joint 356 using pivot pin 357 and mounting bracket 358. Push member joint 356 is fixedly coupled to transmission member 330. FIGS. 47 and 48 show cap assembly 322 assembled where gear portion of gear link 348 intermeshes with gear portion of gear link 342 such that when transmission member 330 is advanced gear link 348 rotates and its gear portion causes the gear portion of gear link 342 to rotate causing needle holder arm 340 to move to a closed position. In the closed position, arm 343 of gear link 342 extends around and above gear link 348 and between cross-member 338d and arch 338c. In the open position (FIG. 45), the arm 343 of gear link 342 extends radially outward relative to needle guard arms 338a, 338b, and the back of the arm 350c may engage the edge of cross-member 338d which can act as a stop to gear movement.

Cap assembly 322 may also include a wash deflector 360 as shown in FIG. 48. The wash deflector redirects fluid from the endoscope to wash the gear mechanism to remove debris. The aforementioned components are all preferably made from biocompatible metals such as stainless steel and titanium although some high strength polymers may be suitable. The vertical positioning of mounting holes 347 and 353 in the needle guard arms 338a, 338b reduces the profile of cap assembly 322 and facilitates delivery of the endoscopic suturing device 320 to a treatment site.

Figure 49:
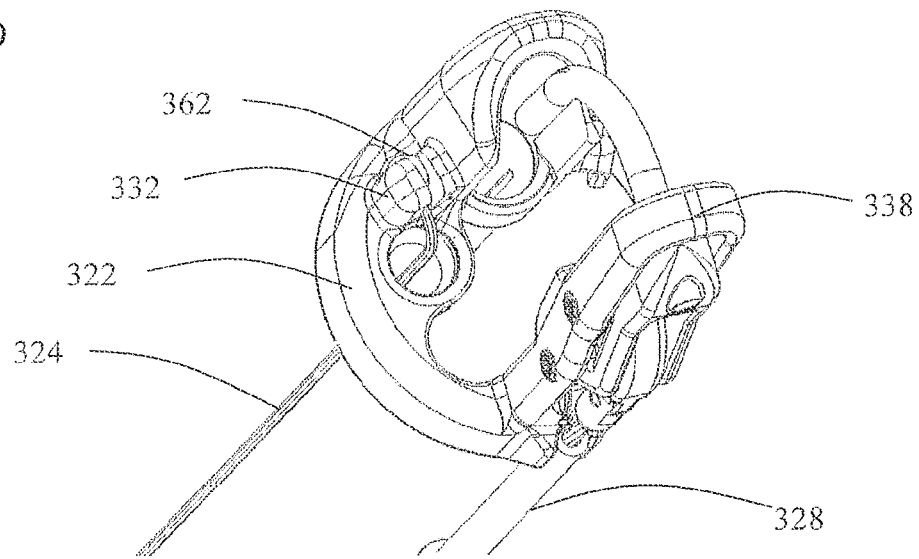
FIG. 49 is still another perspective enlarged view of the cap assembly of an endoscopic suturing system according to an embodiment of the present invention.
Figure 50:
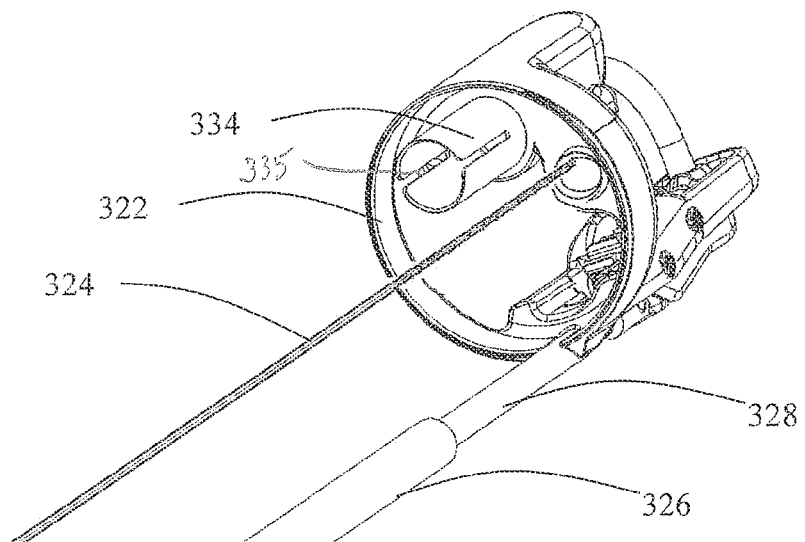
FIG. 50 is still yet another perspective enlarged view of the cap assembly of an endoscopic suturing system according to an embodiment of the present invention.
Figure 51:
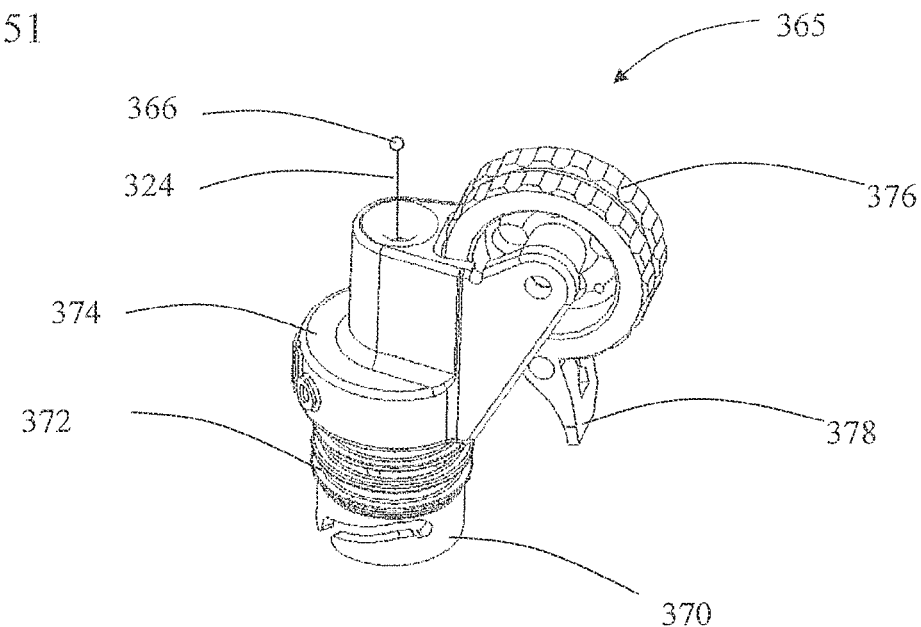
FIG. 51 is perspective enlarged view of the channel lock tensioner assembly in a first configuration according to an embodiment of the present invention.
Figure 52:
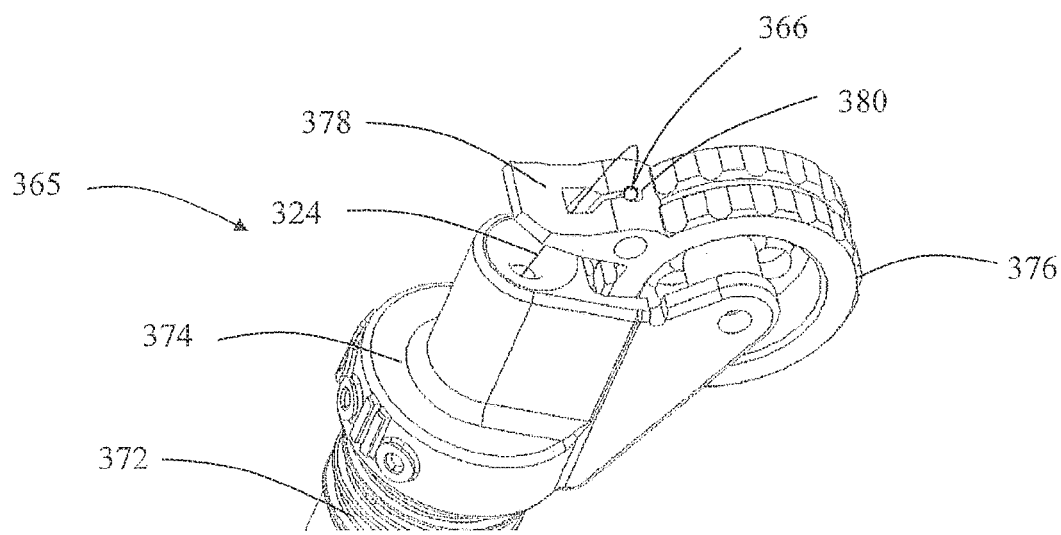
FIG. 52 is perspective enlarged view of the channel lock tensioner assembly in a second configuration according to an embodiment of the present invention.

To aid in the retention of cap assembly 322 on the distal end of the endoscope FIGS. 49 and 50 illustrate views of cap assembly 322 where channel lock member 324 is optionally removably secured in channel lock receiver 332 by channel lock retention member 362. Preferably retention member 362 is formed of a large bead fixedly secured to the distal end of channel lock member 324, whereas channel lock receiver 332 defines a groove 333 having a width smaller than the width of the bead. If desired, the channel lock wire or cable 324 can be welded or otherwise fixed to the channel lock receiver 332 or to another part of the cap assembly. An additional mechanism to increase the retention of the cap assembly to the distal end of the endoscope is show in FIG. 50 where the channel insert guide 334 has a partially split structure (i.e., one or more longitudinal slits 335 are provided). The two portions of the split may be biased outwardly such that when they are placed in the instrument channel of the endoscope they apply and outward force to the inner wall of the channel thereby aiding in the retention of the cap assembly to the distal end of the endoscope. FIGS. 51 and 52 show how tension is applied to channel lock member 324 and maintained at the proximal end of the endoscope by using a channel lock tensioner 365 that secures the proximal channel lock retention member 366 secured to the proximal end of the channel lock member. The channel lock tensioner 365 includes a bayonet lock connector 370, which couples to the endoscope instrument channel and a spring 372 which supports a tensioner housing 374 coupled to a rotatable tensioning wheel 376 having a tab member 378. The proximal end of channel lock member 324 is threaded through tensioner housing 374 and through a valve located at the top of the housing, and is positioned within a tab receptacle 380. The tab receptacle 380 secures channel lock retention member 366 to the tensioner wheel 376. The tensioner wheel 376 can then be rotated (e.g., clockwise) to apply the appropriate tension on the channel lock member and then locked into place by a locking element (not shown). Spring 372 is used to compensate, by compressing, for the bending of the endoscope to maintain a constant tension on the channel lock member. Alternatively, instead of providing a spring 372 between the bayonet lock 370 and the tensioner housing 374, the spring can be provided on the wheel 376 to spring load the wheel toward a desired position (e.g., the position of FIG. 51). As the channel lock member 324 is bent along with the scope through a tortuous path, wheel 376 can rotate against the force of the spring to maintain the desired tension on the channel lock member 324.

Figure 53:
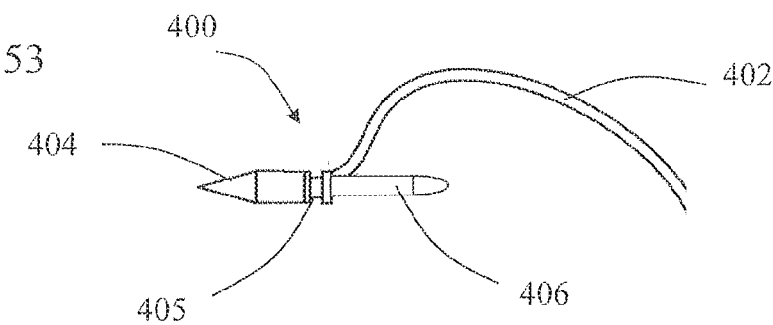
FIG. 53 is an illustrative view of a needle assembly according to an embodiment of the present invention.
Figure 54A:
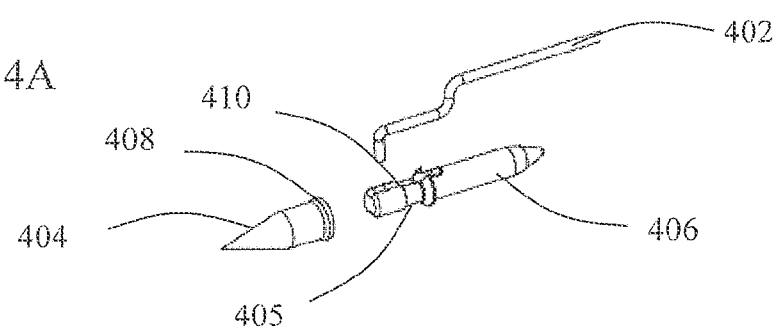
FIGS. 54A through 54C illustrate steps in assembling the components of a needle assembly according to an embodiment of the present invention.
Figure 54B:
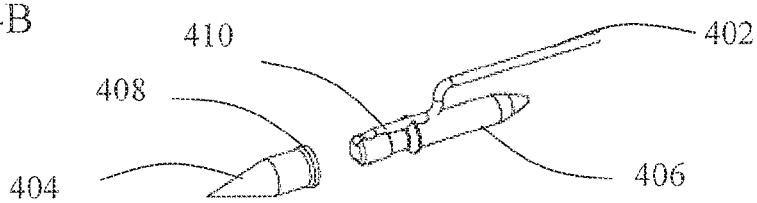
Figure 54C:
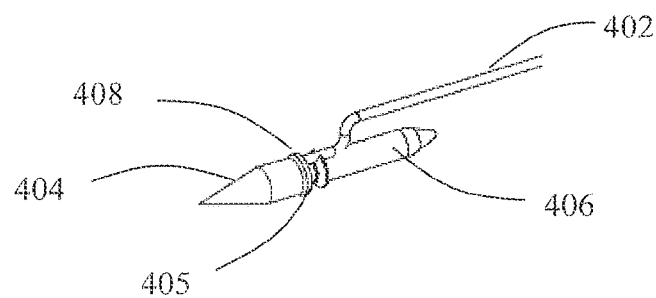

FIG. 53 illustrates needle assembly 400 which comprises suture 402, a needle tip 404, a lock gap 405 and a needle body 406. The suture 402 may be formed of any materials commonly available for surgical suture such as nylon, polyolefins, PLA, PGA, stainless steel, nitinol and others. FIGS. 54A through 54C show detailed exploded views of the components of needle assembly 400. Needle tip 404 has a sharp distal end and a hollow proximal end with a swage lip 408. Needle body 406 has a proximal end adapted to fit within the needle holder arm 340 and a distal end having a suture slot 410. Needle body 406 is adapted to concentrically engage needle tip 404 and create lock gap 405. Flexible suture material 402 is positioned on the distal end of needle body 406 extending through the suture slot 410. The needle tip 404 and needle body 406 are formed from suitable biomaterials and may be made from polymers such as nylon, PEEK, PLA, PGA, PLGA or metals such as stainless steel, nitinol or titanium. The components may be joined using standard joining techniques such as thermal bonding, ultrasonic welding laser welding, adhesives or mechanical crimping.

Figure 55:
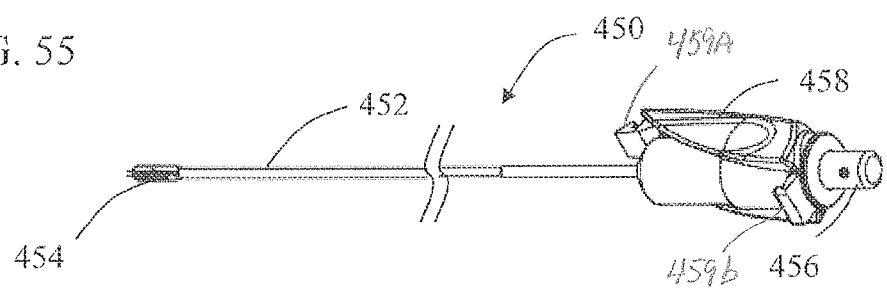
FIG. 55 is an illustrative view of a needle capture device according to an embodiment of the present invention.

FIG. 55 illustrates a needle capture device 450, which includes an elongate catheter or tube 452 having at its distal end a needle capture assembly 454 and at is proximal end a button actuator 456 coupled to handle assembly 458. By way of example only, and not by way of limitation, the needle capture device 450 is a 3 mm tool in that the tube 452 and the distal end needle capture assembly 454 are preferably at most 3 mm in diameter. The handle assembly 458 is preferably adapted to be coupled to the handle assembly operating the needle holder arm of the endoscopic suturing device 320 for ease of use. Toward that end, handle assembly 458 is provided with a deflecting tooth lock 459a and a generally rigid tooth 459b which are arranged to engage with reciprocal cavity and locking element in the handle assembly 600 of the suturing device 320 as discussed below with reference to FIGS. 58 and 59A-59C.

Figure 56A:
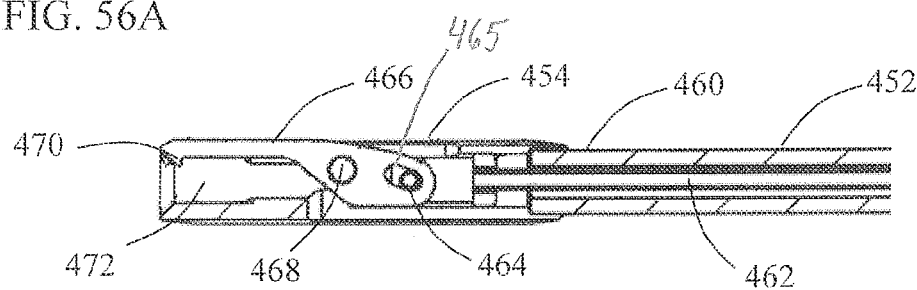
FIGS. 56A and 56B are enlarged partial section views of the distal end of a needle capture device, where
Figure 56B:
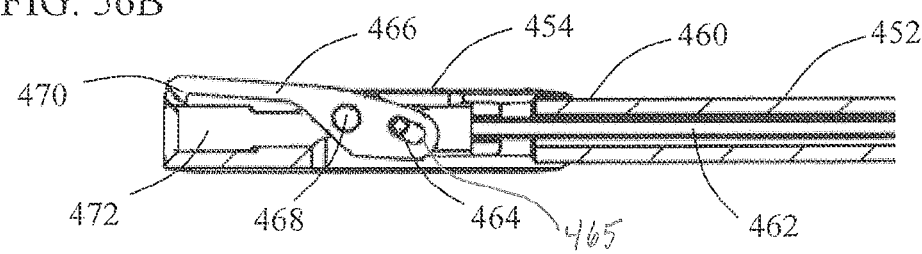
Figure 57:
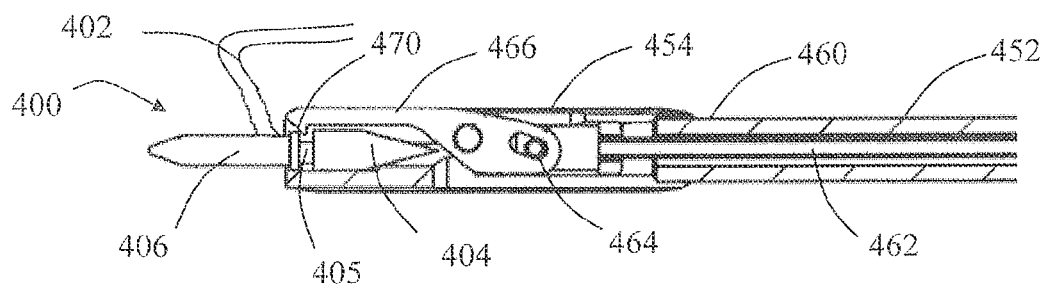
FIG. 57 is an enlarged partial section view of the needle capture assembly interlockingly engaging a needle assembly according to an embodiment of the present invention.
Figure 58:
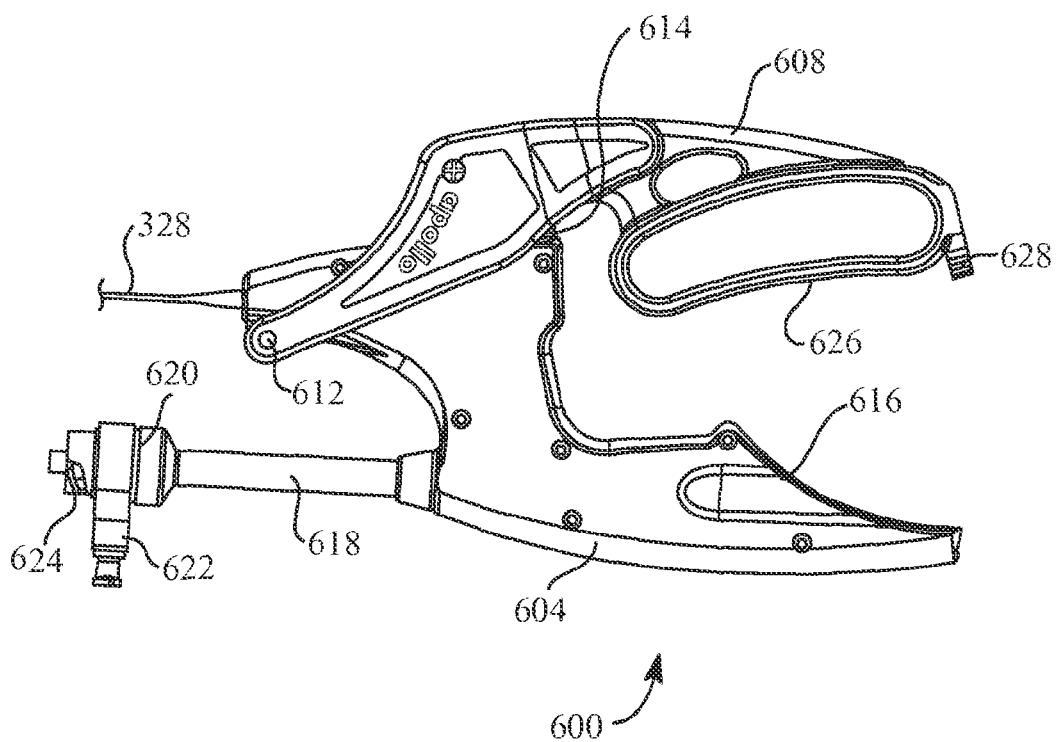
FIG. 58 is a perspective view of a handle assembly of an endoscopic suturing system according to an embodiment of the present invention.

FIGS. 56A and 56B show an enlarged partial cross-sectional view of needle capture assembly 454 and the distal end 460 of tube 452 in closed and open configurations respectively. Slidably positioned within the lumen of tube 452 is push rod or cable 462 which has a proximal end mechanically coupled to button actuator 456 and a distal end coupled to actuator pin 464. Actuator pin 464 is positioned within an angled slot 465 defined in lever arm 466 adjacent fixed pivot pin 468. At the distal end of lever arm 466 is an interlock feature 470. The distal inner portion of needle capture assembly 454 forms needle receptacle 472. Button actuator 456 incorporates a spring assembly which places push rod 462 under a tension load thereby causing lever arm 466 to remain in an engaged or closed configuration as shown in FIG. 56A. When button actuator 456 is depressed, push rod 462 is advanced, there by causing lever arm 466 and interlock feature 470 to a disengaging or open configuration as shown in FIG. 56B. FIG. 57 illustrates needle assembly 400 positioned within needle receptacle 472 of needle capture assembly 454. As shown, needle assembly 400 is secured in place by the interlocking engagement of interlock feature 470 and lock gap 405. In this configuration needle capture device 450 can be used to deliver the needle through the instrument channel of the endoscope to load the needle assembly into needle holder arm 340.

A handle assembly 600 for the endoscopic suturing device 320 is seen in FIGS. 58 and 59A-59C. The handle assembly 600 includes a first stationary handle 604 and a second rotatable handle 608 which is rotatably coupled to stationary handle by pivot axle 612. The rotatable handle 608 is spring-biased to the open position seen in FIG. 58 by a spring 614 which sits and is fixed between the handles. The stationary handle 604 defines a proximal cavity 616 for receiving the handle assembly 458 of the needle capture device 450. Extending from the stationary handle 604 is a tube 618 which terminates in a port 620. Port 620 includes a fluid valve 622 and a mechanical bayonet lock 624 for coupling to the proximal end of an endoscope. Also extending from the stationary handle is sheath 328 which houses the transmission wire 330. Second handle 608 defines a fingers grip section 626, and ratcheted locking element 628 at its proximal end. As described hereinafter, the rotatable second handle 608 is coupled to the transmission wire 330. Movement of the rotatable handle towards the fixed handle causes axial movement (retraction) of the transmission wire 330. Movement of the rotatable handle away from the fixed handle causes axial movement (extension) of the transmission wire 330 in an opposite direction.

Figure 59C:
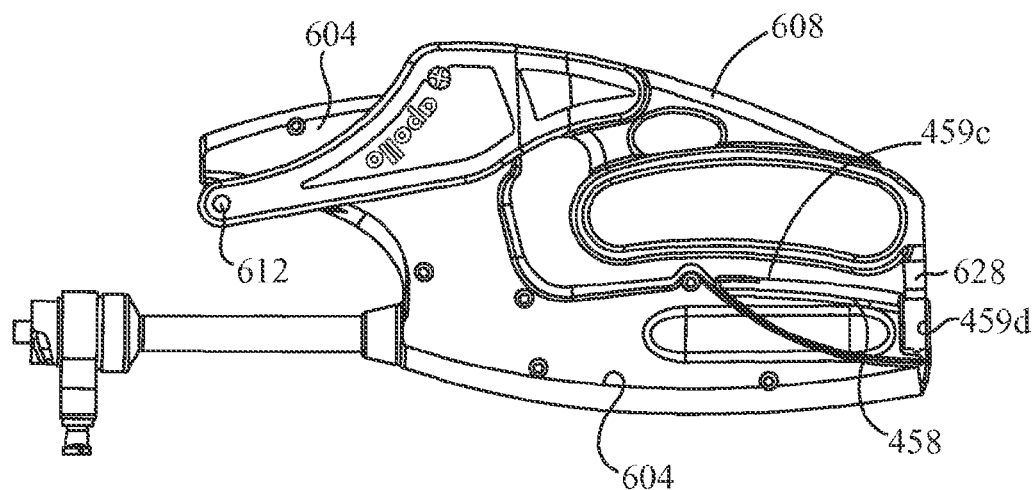
FIG. 59C is a perspective view of the handle assembly of FIG. 58 in an open position and with the handle assembly of the capture assembly locked in position therein.
Figure 59A:
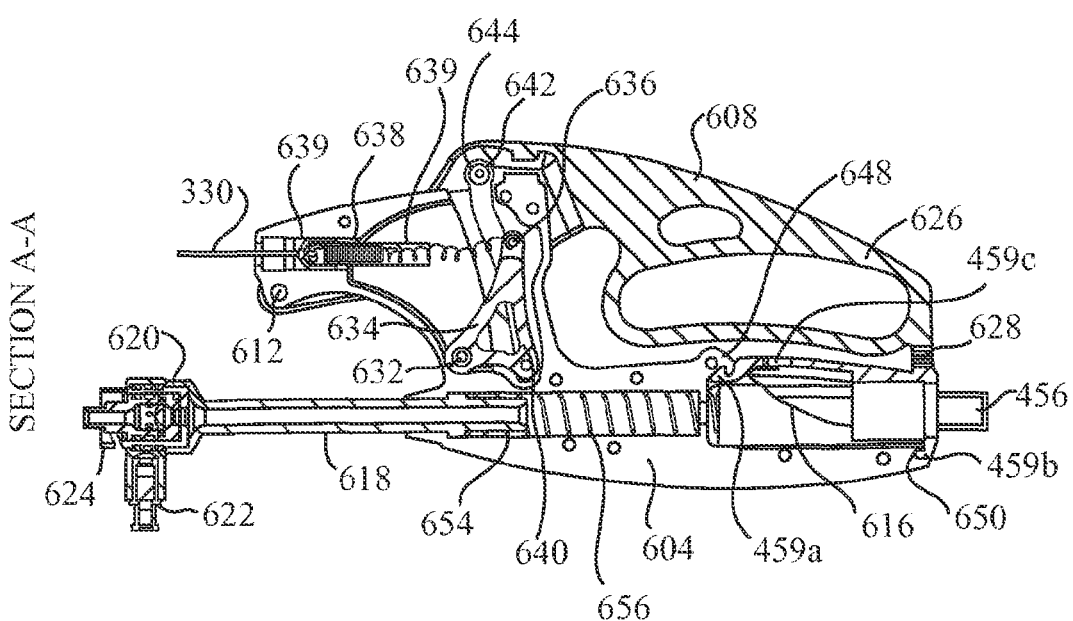
FIG. 59A is a cross-sectional view of the handle assembly of FIG. 58 in a closed position with the handle assembly of the capture assembly locked in position therein.
Figure 59B:
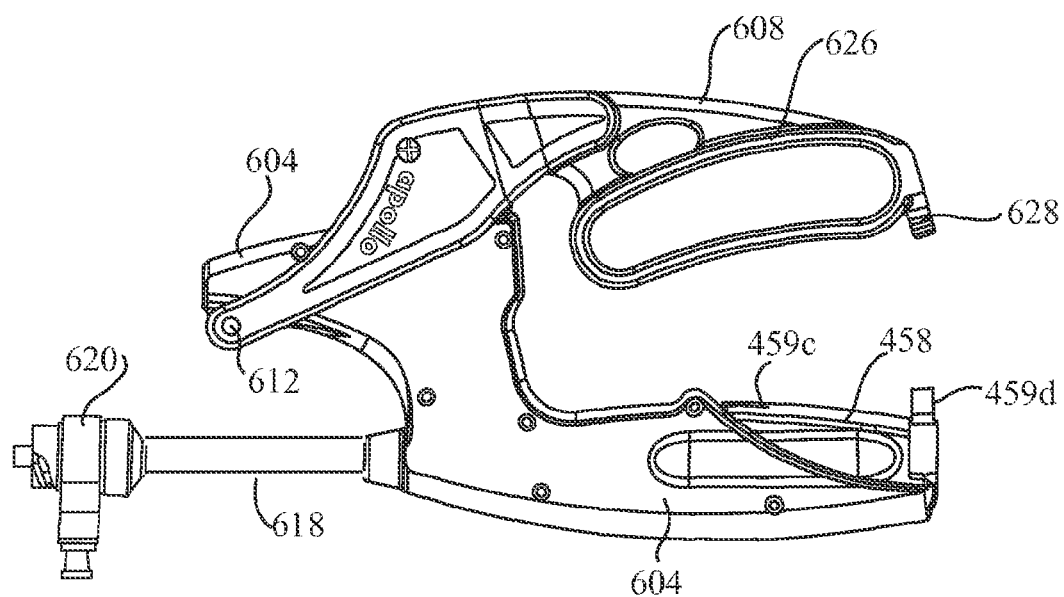
FIG. 59B is a perspective view of the arrangement of FIG. 59A.

Turning now to FIGS. 59A-59C, additional details of the handle assembly 600 are seen in addition to how the handle assembly 458 of the needle capture device 450 interacts with the handle assembly 600 of the endoscopic suturing device 320. More particularly, as seen in FIG. 59A, pivotably coupled to the inside of first handle 604 by pivot pin 632 is an actuation pivot element 634. The transmission wire 330 is coupled to the actuation pivot element 634 at a second location 636 by a spring 638 which can move in a predetermined distance in a cavity 639 defined by fixed handle 604. The rotatable handle 608 is also coupled to the actuation pivot element 634 at a third location 640 by bracket 642 which is coupled to the rotatable handle 608 by post 644. As a result, rotation of the handle 608 (i.e., squeezing) toward the closed position of FIG. 59A causes bracket 642 to pull location 640 of the actuation pivot element 634 downward. Movement of location 640 downward in turn is accompanied by clockwise rotation of the actuation pivot element 634 about pivot pin 632, and thus backward (clockwise) movement of the connection between spring 638 and the actuation pivot element 634 at location 636. Movement of spring 638 backward pulls transmission wire 330 backward.

Also seen in FIG. 59A is the interaction of handle assembly 600 with the handle assembly 458 of the needle capture device 450. More particularly, the stationary handle 604 is provided with a catch 648 which extends into cavity 616 and is designed to engage the flexible tooth (latch) 459a of the needle capture device handle assembly 458. In addition, cavity 616 has a bottom proximal ledge 650 for receiving rigid tooth 459b. Tube 618 which extends out of the stationary handle 604 extends into a tubular cavity 654 of the stationary handle 604 which houses a spring 656, thereby spring loading tube 618 outward.

When it is desired to extend the needle capture device 450 with its distal needle capture assembly 454 through the endoscope, the distal end of the needle capture assembly is threaded into cavity 616 of the stationary handle 604, tubular cavity 654, tube 618, port 620 and then into the endoscope. The needle capture assembly 454 is pushed through until the handle 458 engages the cavity 616 of the stationary handle 604. When pushed as far as possible, rigid tooth 459b aligns with ledge 650, and flexible latch 459a engages catch 648, thereby locking the needle capture device 450 in place. Cable 462 of the needle capture device 450 with sheath 452 extends from the button actuator 457 through the tubular cavity 654, through the tube 618, and through and out of the port 620. To actuate the needle capture assembly, button 456 is pushed as previously described. Disconnection of the needle capture device 450 from the handle assembly 600 is obtained by pressing down on a relieved portion 459c of the handle 458 adjacent and proximal the latch 459a, thereby causing the latch to disengage from the catch 648, and pulling proximally on the handle 458.

As seen best in FIGS. 59B and 59C, the needle capture device handle 458 is preferably provided with a ratchet locking extension or (hooked) tooth 459d. When the needle capture assembly 450 is in place in the handle 600 assembly of the endoscopic suturing device, the handles 604 and 608 may be locked into place in a closed position by engaging ratcheted locking element or tooth 628 on rotatable handle 608 with the similar ratcheted locking extension or tooth 459d of the needle capture assembly 450 (which in turn is locked in stationary handle 604) as seen best in FIG. 59C. As will be appreciated, the teeth 628 and 459d are generally laterally offset, but include hooked portions which after sliding past each other, will engage or grip each other, thereby locking in place. Disengagement is obtained by applying a relative lateral force to one or both of the handles.

Figure 60A:
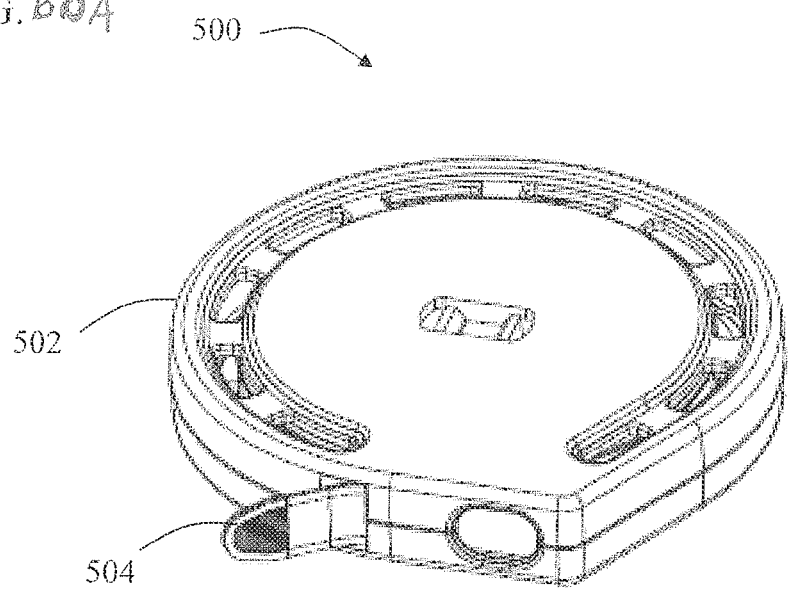
FIG. 60A is a perspective view of a molded suture dispenser including a removable needle shield tab.
Figure 60B:
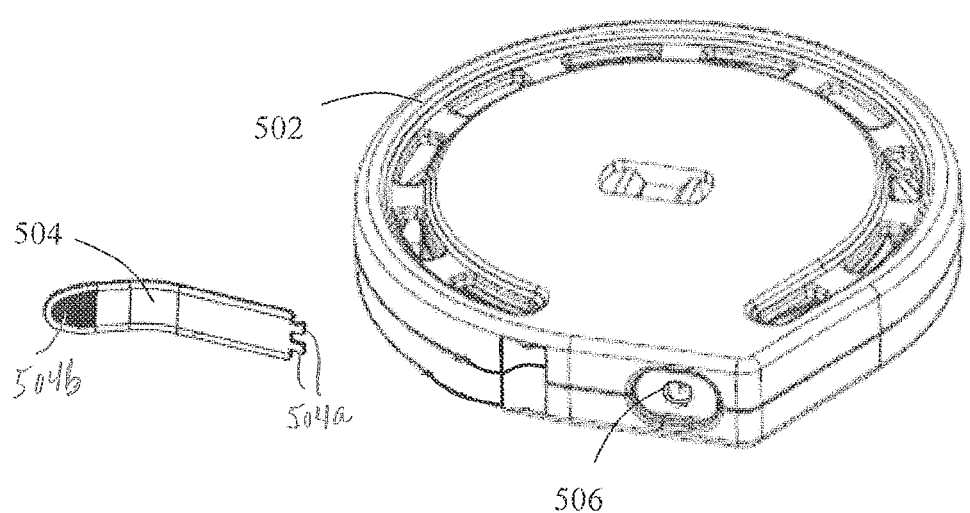
FIG. 60B is a perspective view of the suture dispenser where the needle shield tab has been removed to provide access to the needle retaining member.
Figure 60C:
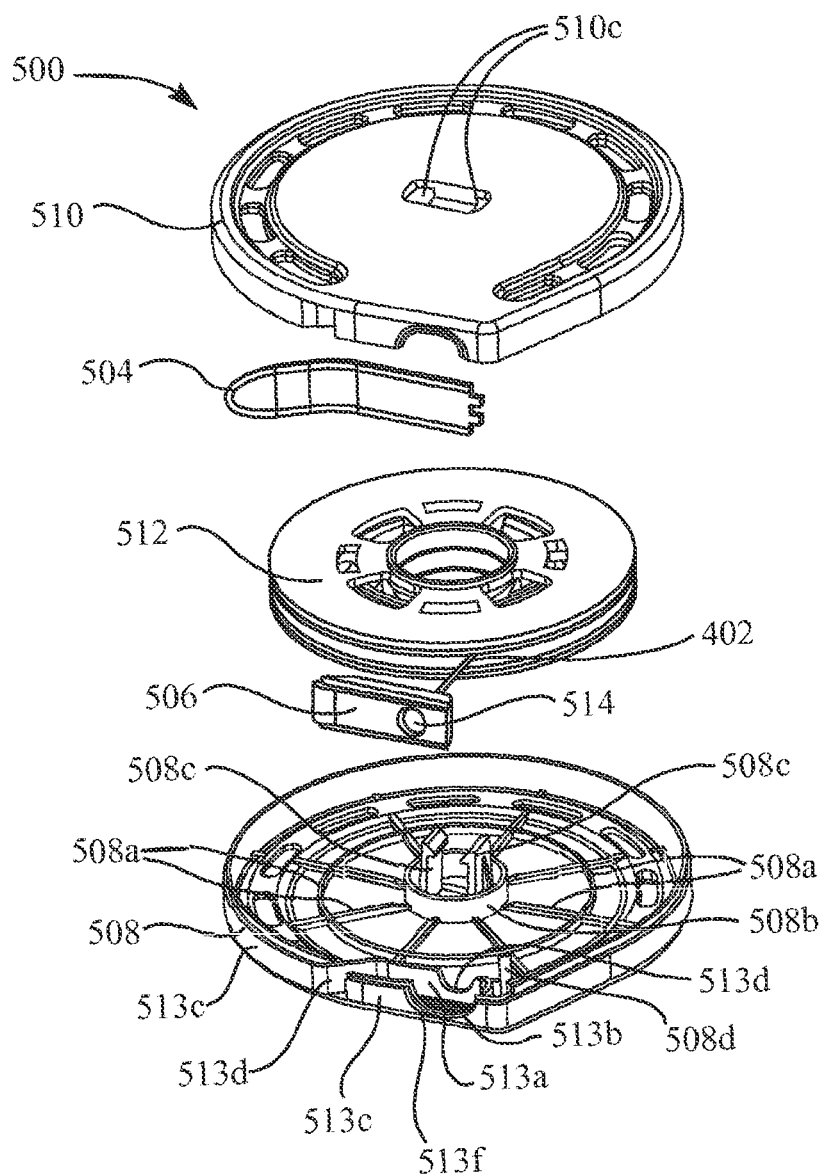
FIG. 60C is an exploded perspective view illustrating the components of the molded suture dispenser.

An innovative suture dispenser 500 having a dispenser body 502 and a removable needle shield tab 504 is shown in FIG. 60A. The suture dispenser 500 is shown in FIG. 60B with the needle shield tab 504 removed from the dispenser revealing a needle retaining member 506. To better illustrate the suture dispenser 500, FIG. 60C shows an exploded perspective view of the components. Suture dispenser 500 includes a lower body 508 and upper body 510 which together form a cavity which houses suture spool 512 containing suture 402, needle shield 504 and needle retaining member 506. The lower and upper bodies 508, 510 preferably include ribs 508a, 508b (similar ribs on upper body not shown) on and about which spool 512 rests so that spool 512 can rotate with a minimum of friction in the cavity. The lower and upper bodies 508, 510 are also each preferably provided with walls 513a, 513b, 513c (seen in FIG. 60C only with respect to lower body 508) which retain the needle retaining member 506 in place but permit the needle shield tab 504 to be removed. More particularly, wall 513a is seen to form a back wall for the needle retaining member. It includes a cutout or orifice 513d for receiving a rear portion of the needle retaining member (and needle) and it angles at 513e to join outer wall 513c. Wall 513b is a low wall which is placed in between walls 513a and 513c and is connected to the angled portion 513e of wall 513a. Wall 513b effectively forms two grooves with the first groove seating the needle retaining member 506 and holding it in place and the second groove seating a portion of the needle shield tab 504. Needle shield tab, however extends out of a radial opening or orifice in outer wall 513c and can be pulled out (i.e., can slide out) completely to reveal a receiving cavity 514 in the needle retaining member 506. The outer wall 513c is also provided with an opening or orifice 513f in front of the receiving cavity 514. The suture dispenser 500 and most of its components are easily fabricated at low cost using suitable polymers, such as polyethylene, polypropylene or polystyrene, injection molding and preferably designs which snap together (e.g., latches 508c and hollow receiving post 508d on lower body 508, and catches 510c and post (not shown) on upper body 510).

As seen in FIG. 60B, needle shield 504 is preferably provided with prongs 504a. The prongs are squeezably held between ribs (not shown) extending from the lower and upper bodies 508, 510 in order to hold the needle shield 504 in place. However, because the prongs are resilient, application of force to the tab portion 504b of the needle shield 504, permits the needle shield 504 to be removed from the dispenser body 502.

Figure 61A:
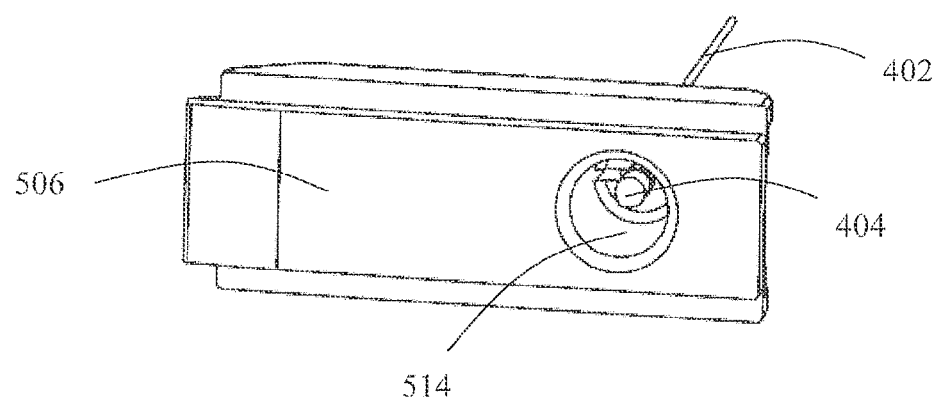
FIG. 61A is an enlarged perspective view of the needle retaining member.
Figure 61B:
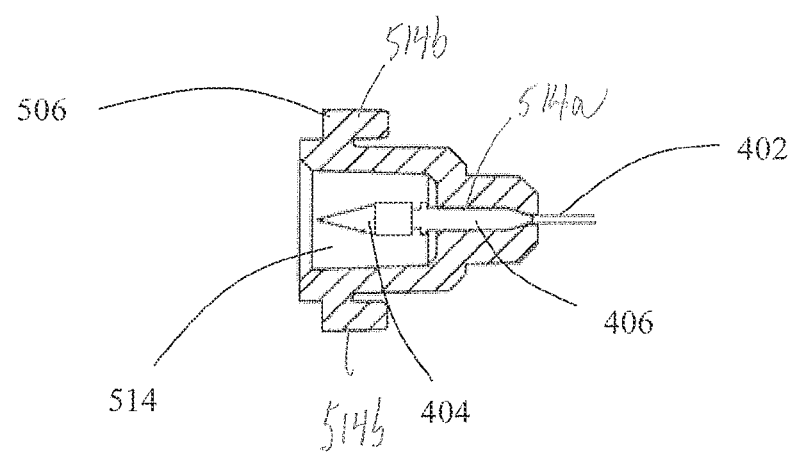
FIG. 61B is an enlarged partial cross-sectional view of the needle retaining member securing the removable needle assembly.

As previously mentioned, needle retaining member 506 includes a needle receiving cavity 514 as shown in FIGS. 61A and 61B where removable needle assembly 400 is held. As shown in the partial cross-section view of FIG. 61B, needle body 406 is frictionally held within an orifice 514a defined in the body of retaining member 506 (in much the same manner it is frictionally held in the needle holder arm 340 (FIG. 46) and the needle is connected to suture 402 which is wound on the suture spool. Needle tip 404 is accessible to the needle capture assembly 454 through needle receiving cavity 514; i.e., the cavity provides room around the needle tip to permit the needle capture assembly to enter the cavity and grab the needle. Also as shown in FIG. 61B, the needle retaining member 506 has laterally elongated upper and lower flanges 514b which are receiving and seat in the grooves formed by the walls 513a, 513b of the lower and upper bodies 508, 510 of the suture dispenser 500. The body of the needle retaining member has a cylindrical portion which extends backward through the orifice 513d of the inner wall 513a.

Figure 62A:
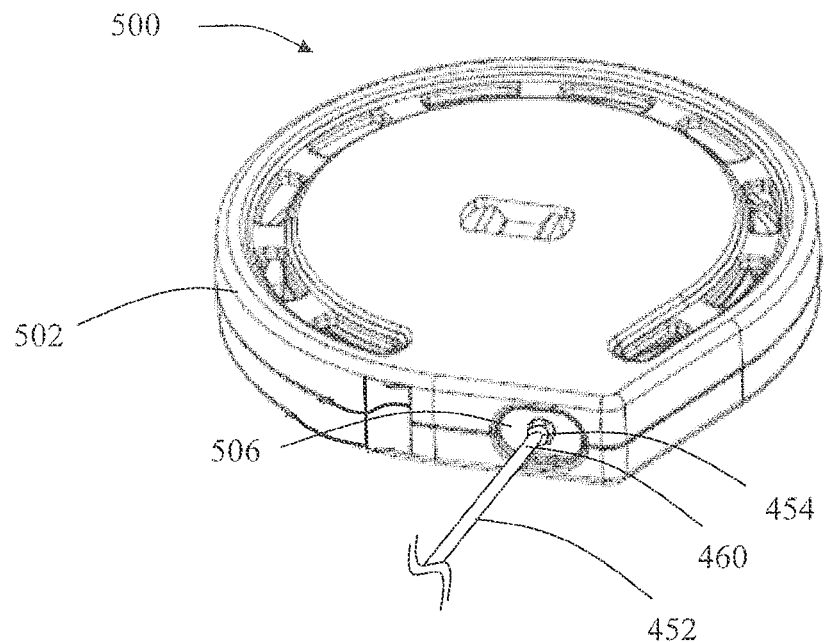
FIG. 62A is a perspective view illustrating the needle capture device engaging the suture dispenser.
Figure 62B:
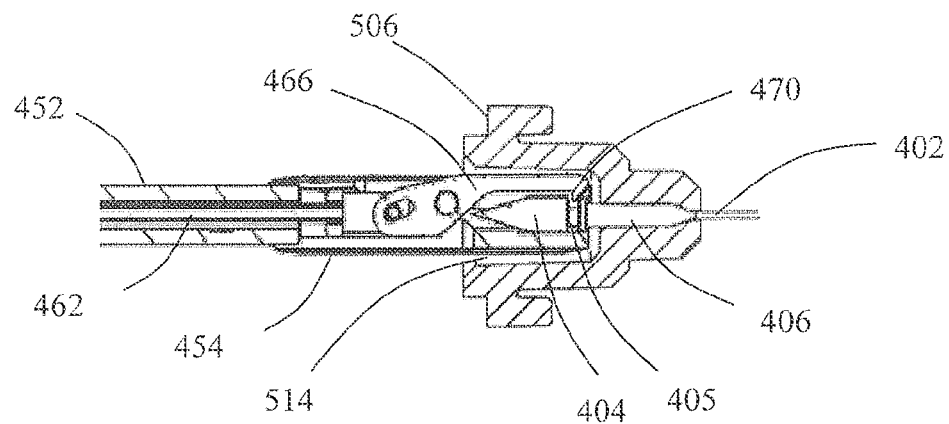
FIG. 62B is an enlarged partial cross-sectional view of the needle capture assembly interlockingly engaging the removable needle assembly positioned within the needle retaining member of the suture dispenser.

FIGS. 62A and 62B show the suture dispenser 500 receiving the needle capture assembly 454 of needle capture device 450. FIG. 62B shows a partial cross section view of the needle capture assembly 454 interlockingly engaged with the needle for removal from the dispenser.

Figure 63:
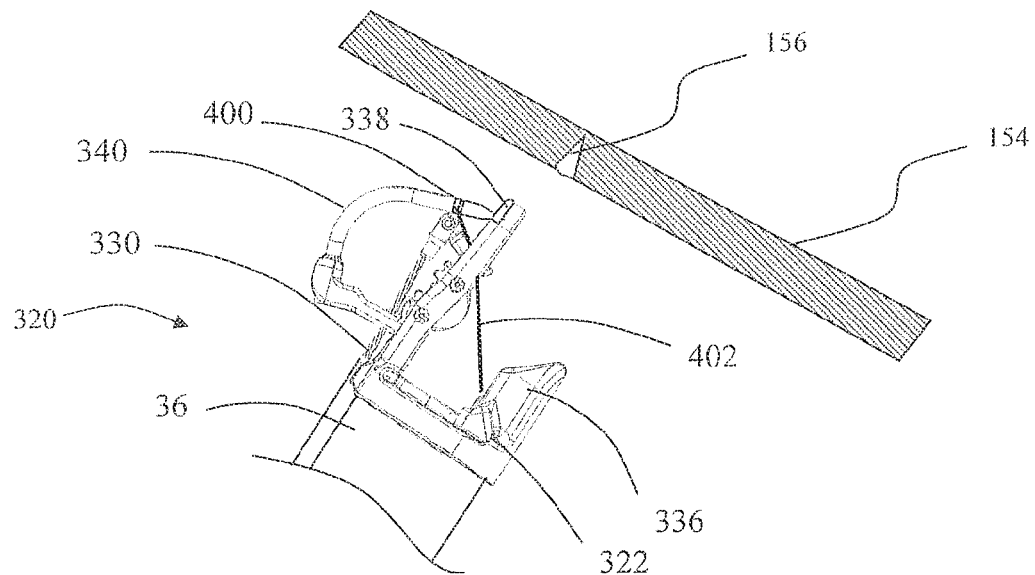
Figure 64:
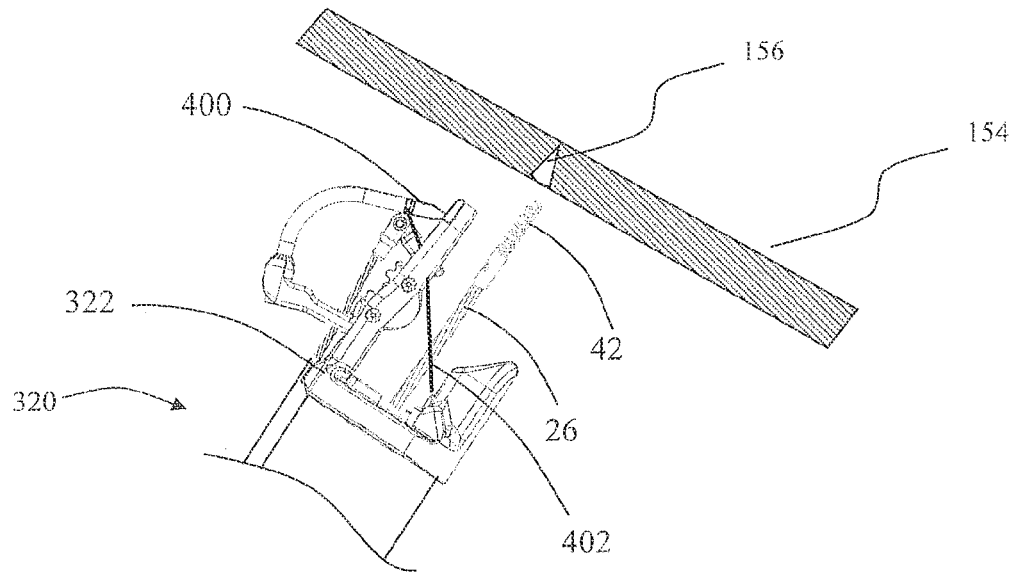
Figure 65:
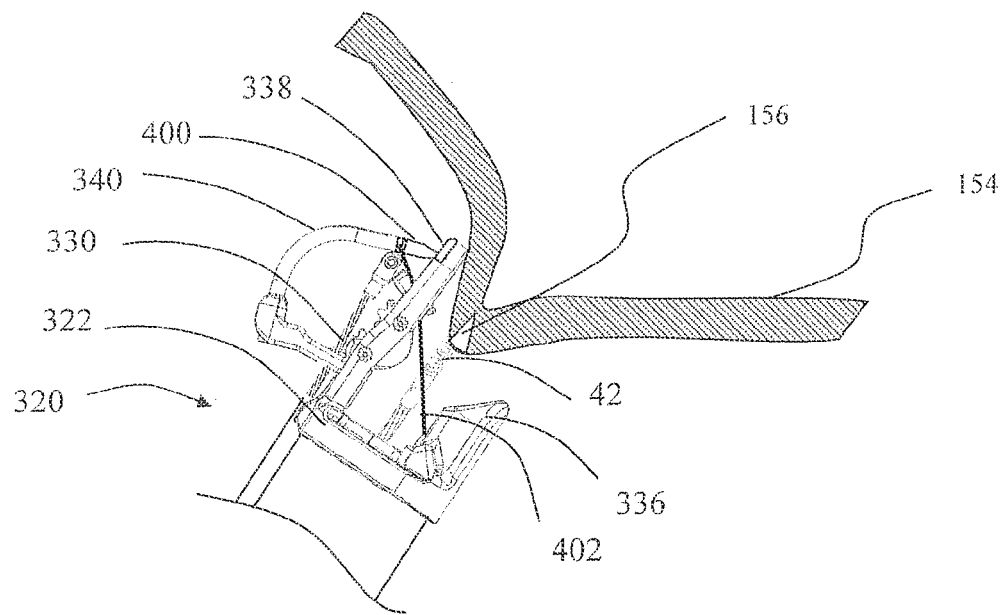
Figure 66:
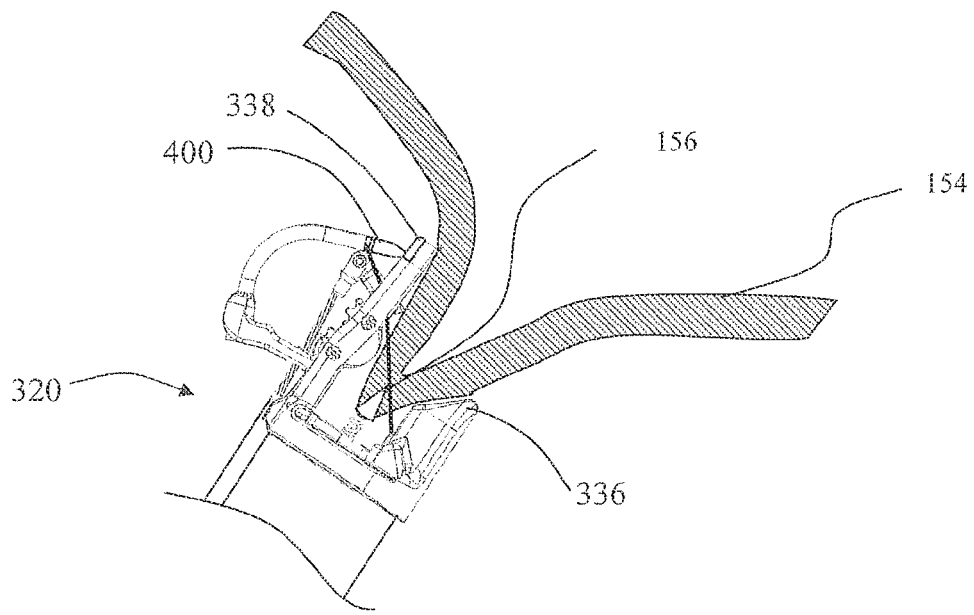
Figure 67:
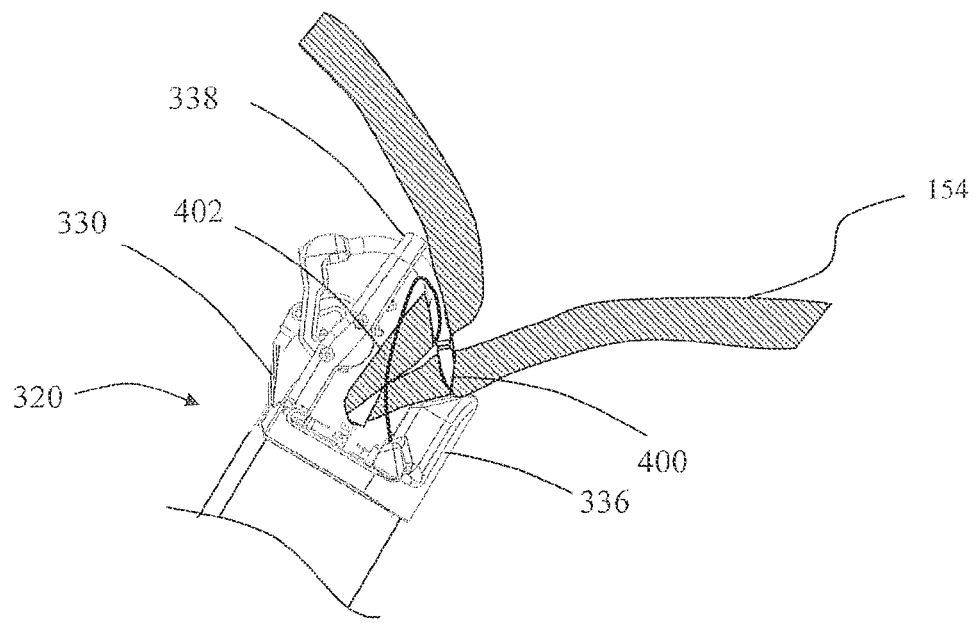
Figure 68:
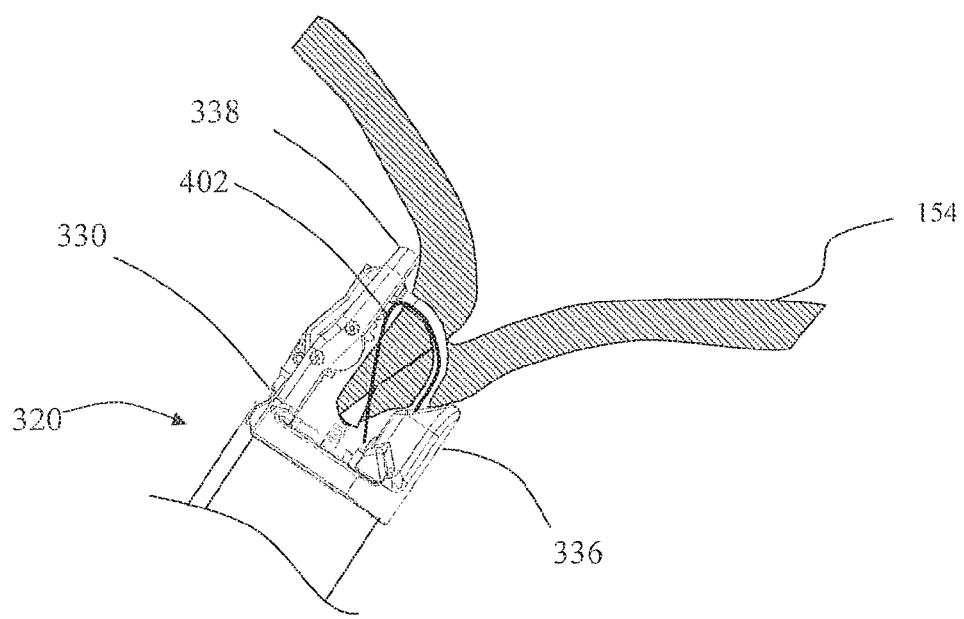
Figure 69:
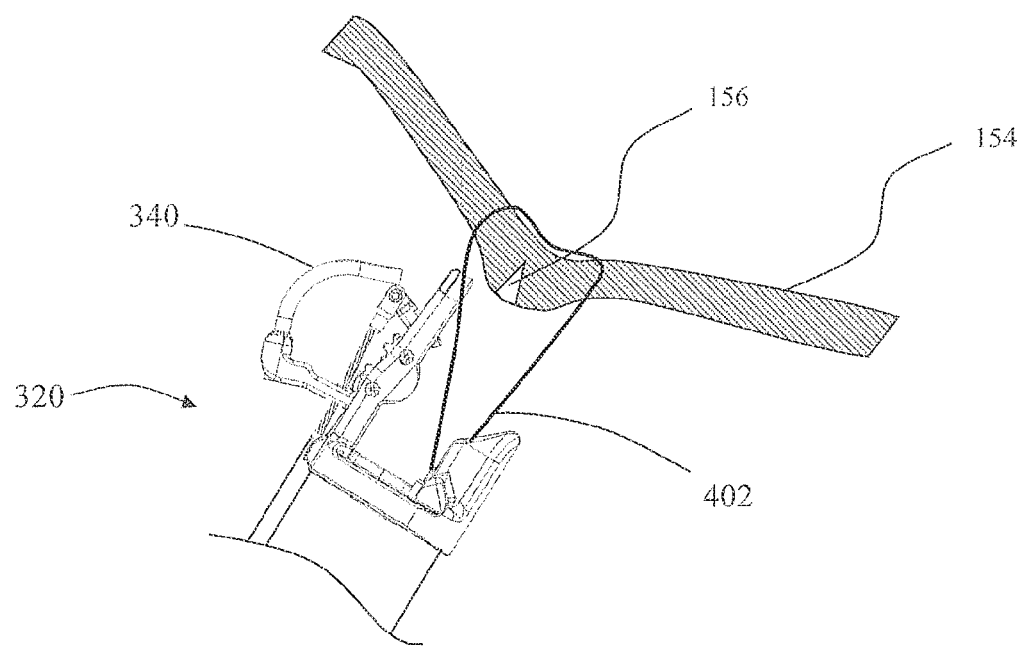

FIG. 63 through FIG. 69 depicts a method of performing a suturing operation using an endoscopic suturing device 320 of the present invention. As shown in FIG. 63, the endoscopic suturing device 320 is positioned adjacent tissue 154 which has a tissue defect 156 to be closed. The endoscopic suturing device 320 is in an open configuration and the tip of needle assembly 400 is shrouded by needle guard 338. FIG. 64 shows the tissue grasper 26 is extended from the endoscope instrument channel such that helical tip 42 is adjacent tissue defect 156. Rotation of the tissue grasper 26 causes the helical tip 42 to securely engage the tissue 154 adjacent to the tissue defect 156. The tissue 154 may be brought closer to the endoscope by slightly retracting the tissue grasper 26 into the instrument channel of the endoscope as shown in FIG. 65. During the retraction of tissue, the needle guard 338 prevents the tissue from dragging against the tip of needle assembly 400, thereby reducing inadvertent tissue damage. The degree of tissue retraction correlates to the size and location of the stitch. For instance to have a larger amount of tissue sutured, the tissue grasper may bring the tissue 154 close to the endoscope as shown in FIG. 66. When attempting to suture a large amount of tissue, the position of the angled distal end of tissue guard 336, in conjunction with the needle guard 338, aids in folding the tissue in preparation for suturing and preferably aids in preventing the tissue from locating immediately adjacent and thereby clogging the needle capture device. The needle holder arm 340 is actuated to move to a closed position causing the needle assembly 400 to pierce tissue 154. The angled portion of tissue guard 336 provides support for the tissue allowing the needle to more easily penetrate the tissue as shown in FIG. 67. The suture 402 is pulled through the tissue as shown in FIG. 68. The control over the amount of tissue retracted allows the physician the ability to perform a partial thickness stitch within the wall of a tissue or a full thickness stitch which extends through a wall of tissue. The needle capture device captures the needle assembly 400 and removes it from the needle holder arm 340(not shown). FIG. 69 shows the needle holder arm 340 moved to an open configuration and removed from tissue 154. Suture 402 remains through the tissue. To continue a running stitch, the needle holder arm can be reloaded with the needle assembly without needing to remove the endoscopic suturing device from the body as previously described. If only one stitch is required the suture may be tied into a surgical knot or a cinch device used to secure the suture, thereby closing the tissue defect.

Figure 70:
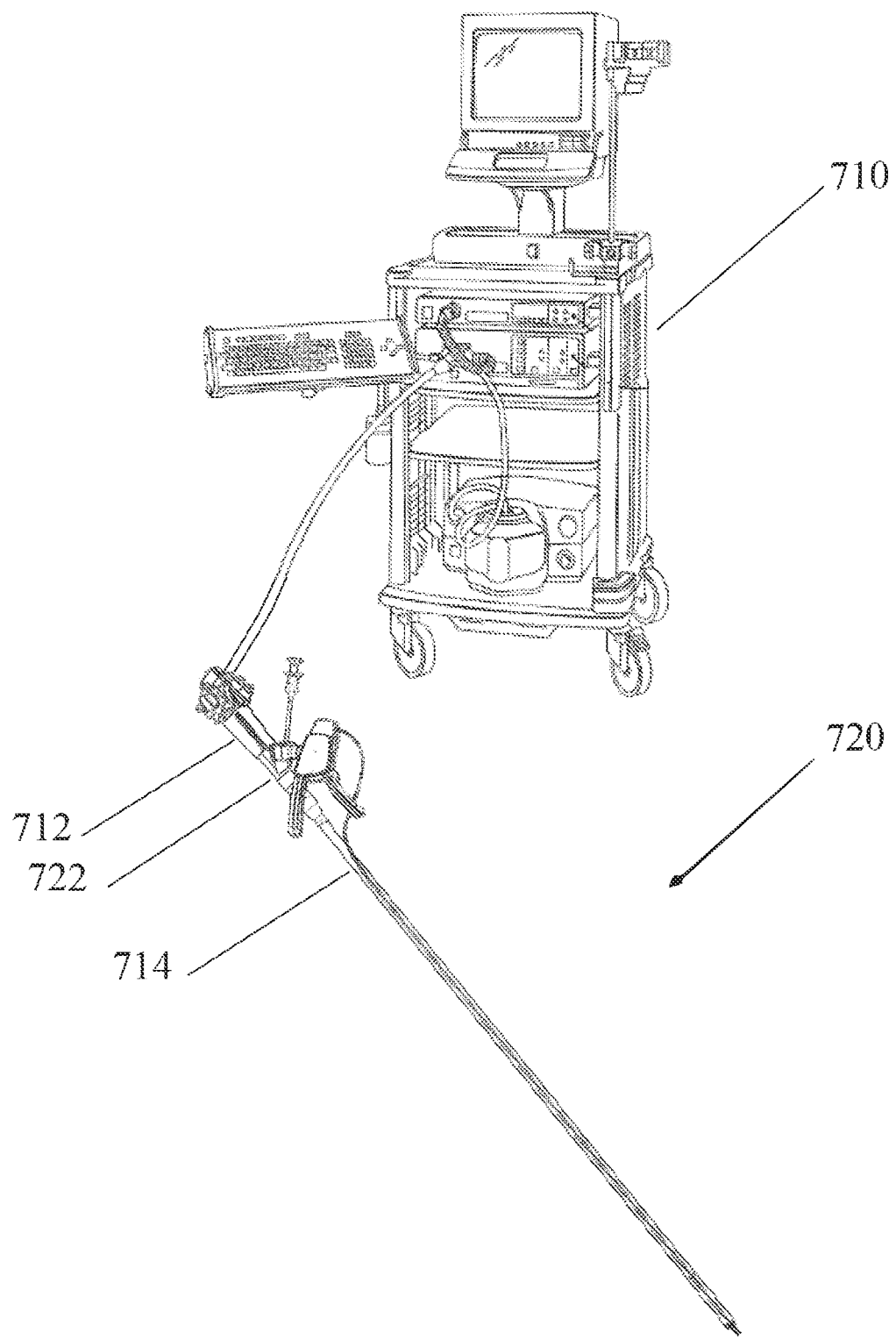
FIG. 70 is an illustrative view showing an endoscopic suturing system with endoscope system according to yet another embodiment of the present invention.
Figure 71:
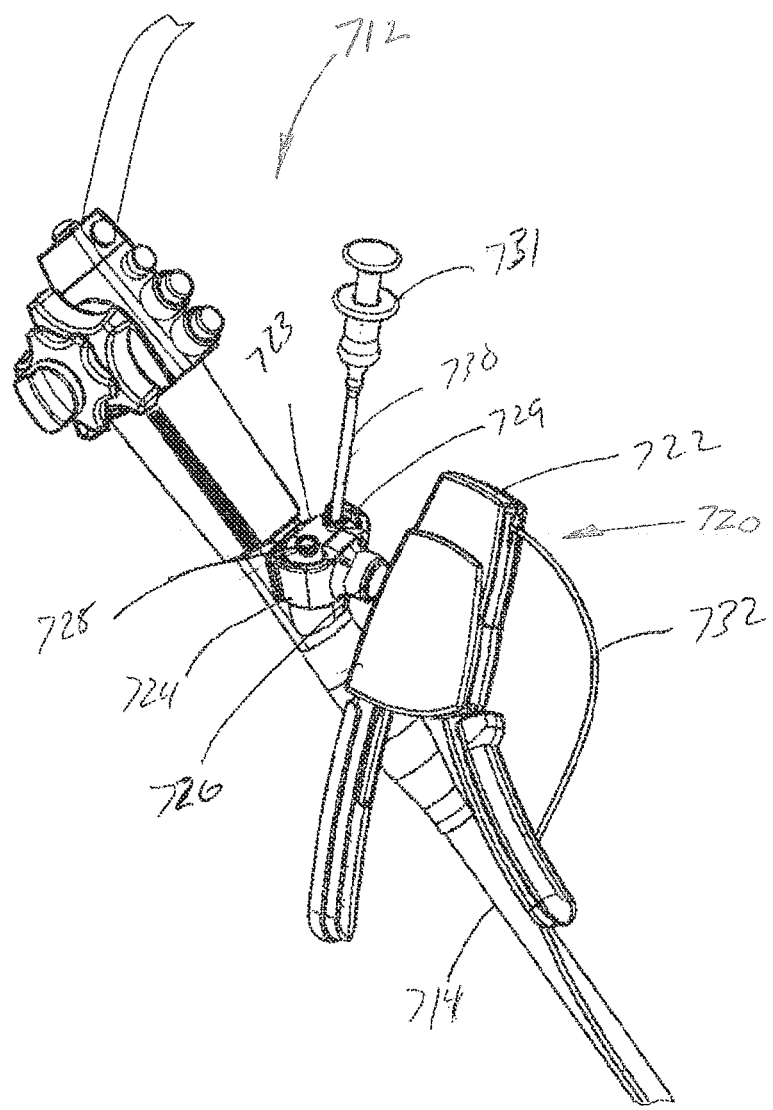
FIG. 71 is an enlarged view of the proximal portion of an endoscope and an endoscopic suturing system shown in FIG. 70.
Figure 72A:
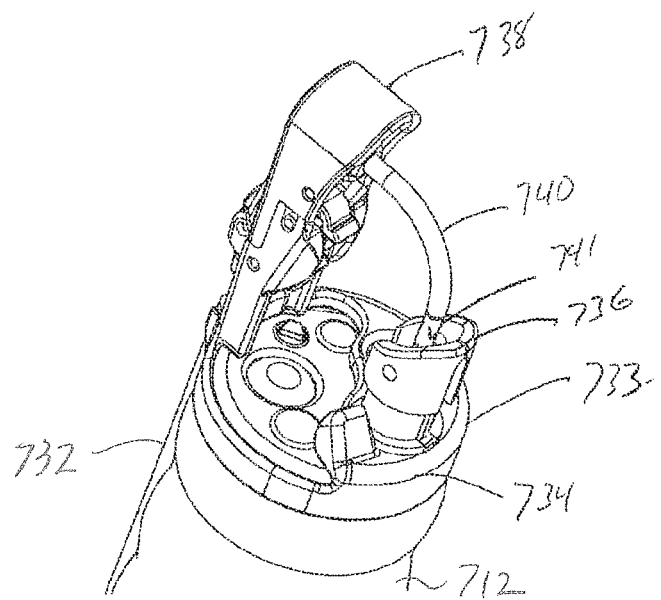
FIG. 72A is a perspective enlarged view of the distal end of an endoscopic suturing system according to an embodiment of the present invention where the needle holder arm of the suturing device is closed.
Figure 72B:
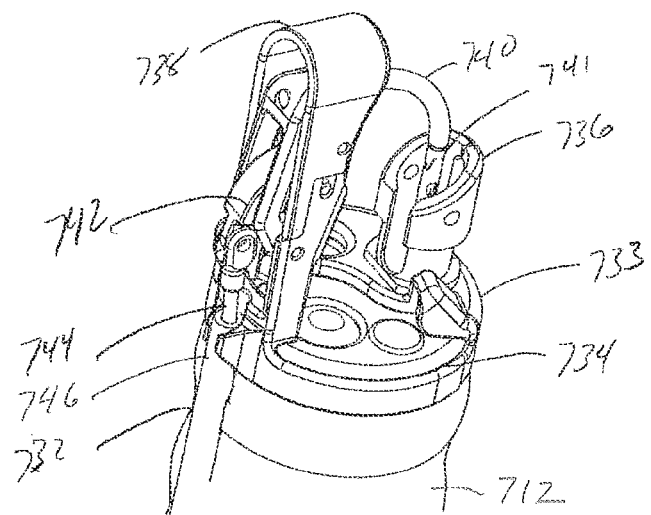
FIG. 72B is a perspective enlarged view of the distal end of the endoscopic suturing system in FIG. 72A from another viewing angle.
Figure 73A:
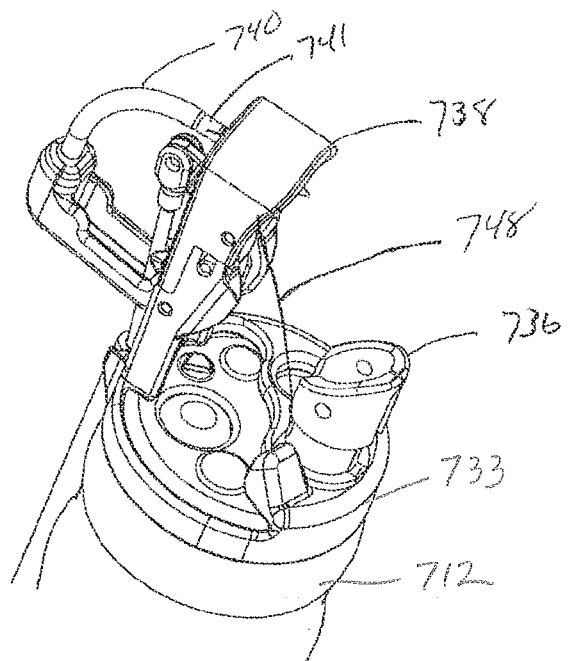
FIG. 73A is a perspective enlarged view of the distal end of an endoscopic suturing system according to an embodiment of the present invention where the needle holder arm of the suturing device is open.
Figure 73B:
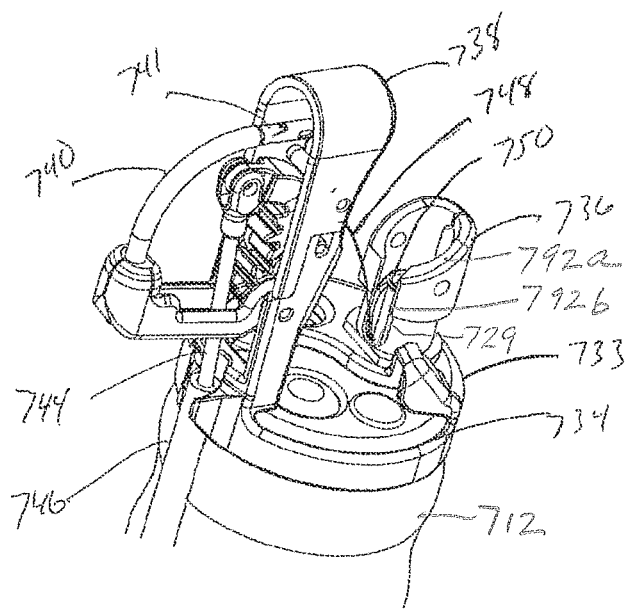
FIG. 73B is a perspective enlarged view of the distal end of the endoscopic suturing system in FIG. 73A from another viewing angle.

FIG. 70 illustrates an endoscope system 710 which comprises an endoscope 712 having an insertion tube 714 and an endoscopic suturing device 720 as part of an endoscopic treatment system according to another embodiment of the present invention. FIGS. 71 through 72B illustrate respectively the proximal and distal portions of endoscope 712 and endoscopic suturing device 720. The endoscopic suturing device 720 has an operable handle 722 which is removably coupled to endoscope 712 at the instrument channel housing 723 by handle bracket 724 with a movable joint 726. Instrument channel housing 723 of endoscope 712 allows access to first and second instrument channels 728 and 729, respectively. The endoscopic suturing device 720 includes an elongate needle capture device 730 that extends to the distal end of endoscope 712 and slidably positioned within instrument channel 729. The needle capture device 730 also includes a handle 731. The endoscopic suturing device 720 is operated by handle 722 which is proximally coupled to transmission assembly 732 which extends distally along the exterior of insertion tube 714 to the distal of endoscope 712. The transmission assembly 732 is coupled at its distal end to a cap assembly 733 which is positioned over the distal end of endoscope 712. FIGS. 72A and 72B shows cap assembly 733 having a cap base 734, a lower mounting portion 794 to mount the cap base to the endoscope, a tissue guard 736, a needle guard 738, a needle holder arm 740 and a needle assembly 741. The needle holder arm 740 is shown in a closed position which places needle assembly 741 partially inside of tissue guard 736. Needle holder arm 740 is rotatably coupled to gear assembly 742 and is operated by axial movement of elongated transmission member 744 through transmission catheter 746 of transmission assembly 732. The distal end of transmission catheter 746 is fixed to cap base 734. FIGS. 73A and 73B show cap assembly 733 coupled to the distal end of endoscope 712 where needle holder arm 740 is in an open position. In the open position, needle assembly 741, which is removably coupled to needle holder arm 740, is shielded within needle guard 738 and suture 748 is visible extending into instrument channel 729. In FIG. 73B suture 748 is shown extending into instrument channel 729 adjacent the needle capture device distal end 750.

FIG. 75 illustrates a detailed exploded view of the components of cap assembly 733. Transmission member 744 is fixedly coupled to a push member joint 752 having mounting bracket 754. Push member gear link 755, having a mounting hole 756, is pivotably coupled to mounting bracket 754 by securing pivot pin 757 through mounting bracket 754 and mounting hole 756. Push member gear link 755 also includes mounting hole 758 and lateral gear teeth 759. Needle holder arm gear link 760 includes a mounting hole 762, adjacent lateral gear teeth 764, and a needle holder arm mounting hole 766. Needle guard 738 is generally formed of two pieces comprising a "U" shaped upper portion 770, having a wide needle cover 772 and includes a pair of mounting holes 774 (one on each side of the "U") for additional components and a lower portion 776 that extends the legs of the "U" which is fixedly coupled to both the upper portion 770 and cap base 734 and includes two pair of mounting holes 778 and 780. Needle holder arm gear link 760 is secured to lower portion 776 by positioning pivot pin 782 through mounting hole 778 and mounting hole 762. The lateral gear teeth 759 of push member gear link 755 are positioned to intermesh with the lateral gear teeth 764 of needle holder arm gear link 760 and the two gear links are secured by positioning pivot pin 784 through mounting hole 780 in lower portion 776 and mounting hole 758 in push member gear link 755. Pin 786 is positioned in mounting hole 774 of upper portion 770 and serves to prevent undesirable movement of needle holder arm link 760. Needle holder arm end effector 740 is coupled to needle holder arm gear link 760 by fixedly securing needle holder arm end 788 within mounting hole 766. Needle holder arm 740 includes a straight tip member 790 adapted to engage needle assembly 741 and defining a longitudinal axis therethrough. Tissue guard 736 has a generally cylindrical shape and tubular form with a distal or upper portion 792 having a distal surface 792a obliquely angled relative to a longitudinal axis through the tissue guard, and a suture passage recess 792b through which suture may extend from within the working channel of the endoscope toward the retracted needle assembly 741 mounted on the needle holder arm 740 (FIG. 73B). The lower mounting portion 794 has a generally cylindrical shape and tubular form that is provided in axial alignment with the tissue guard 736. The tissue guard 736 and lower mounting portion 794 are preferably integrally formed from a common tubular member, and an opening extends longitudinally through both the tissue guard 736 and lower mounting portion 794. A proximal portion of the mounting portion 794 tapers to a smaller profile in a direction transverse to its longitudinal axis without decreasing the diameter of the opening through the mounting portion to aid in its insertion into the instrument channel 729, as discussed in more detail below. In one embodiment, the proximal end of the mounting portion 794 has a planar end surface 794a oriented at an oblique angle relative to the longitudinal axis through the mounting portion 794 (see also FIG. 74). Alternatively, the proximal portion may include a surface that taper along a sloped curve to a reduced end cross-sectional profile. A base mounting stop 796 is located between the upper and lower portions to properly position the guard 736 and mounting portion 794 on the cap base 734. An elongate slot 797 in the wall of tissue guard 736 extends from lower mounting portion 794 through base mounting stop 796 and a portion of upper portion 792. The slot 797 may be straight, as shown in FIG. 75, or as shown in the alternative embodiment of FIG. 75A, the slot 797a may be non-straight, e.g., extending in a zig-zag. Such non-straight extending slot 797a reduces potential interference with suture extending in proximity to the slot. Cap base 734 includes a mounting hole 798 in which to position lower mounting portion 794. Base mounting stop 796 mates about mounting hole 798 to properly longitudinally portion the tissue guard 736 and the mounting portion 794 and is subsequently fixedly secured, preferably by laser welding. Lower mounting portion 794 is preferably formed of a resilient material and has an outer diameter which is slightly larger than the diameter of the instrument channel of the endoscope. The outwardly biased diameter of lower mounting portion 794 may be temporarily compressed or squeezed using a fingers or a tool (not shown) to reduce the diameter for insertion into the instrument channel. Once the compression source is removed the resilient bias of the lower portion 794 outer diameter engages with the inner diameter wall of the instrument channel with sufficient force to retain cap assembly 733 on the distal end of endoscope 712.

Figure 77A:
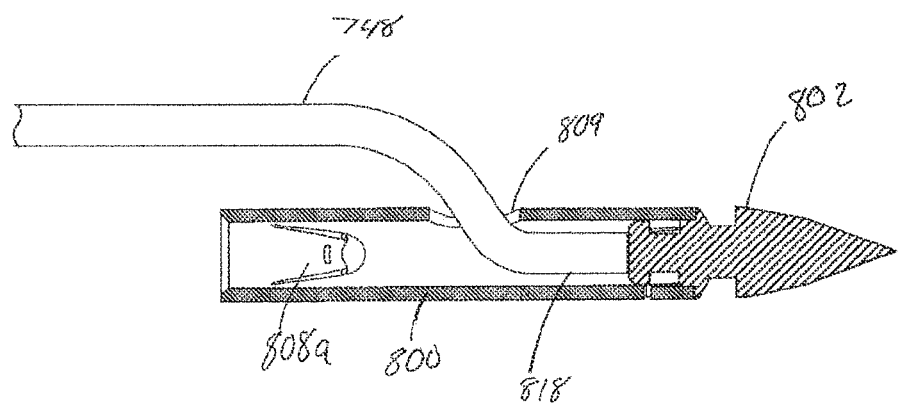
FIG. 77A is a partial section view of a needle assembly for use with an endoscopic suturing device according to an embodiment of the present invention.
Figure 77B:
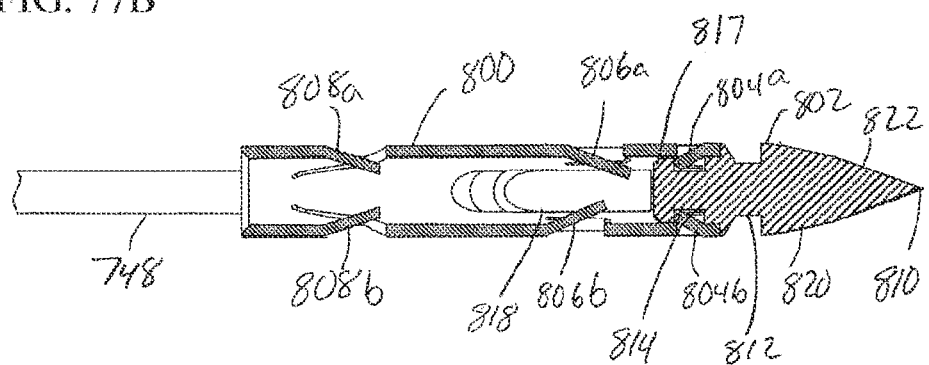
FIG. 77B is a partial section view of a needle assembly for use with an endoscopic suturing device according to an embodiment of the present invention.

FIG. 76A illustrates needle assembly 741 which comprises a preferably straight, hollow needle body 800, a straight needle tip 802 and suture 748. Needle body 800 is preferably formed from a hypotube of suitable biocompatible material. Needle body 800 is preferably processed, by laser cutting, to form various features in the wall of the tube along the length of the tube such as tip tabs 804a and 804b located at one end of the tube, suture tabs 806a and 806b, needle holder arm tabs 808a and 808b at the other end of the tube, as well as, suture hole 809 positioned generally in the middle of the tube. FIG. 76B shows an exploded view of needle assembly 741 to provide further component detail. Needle tip 802 has a sharp end 810, a capture groove portion 812, a tab groove portion 814, a cap plug portion 816 positioned between the grooves and a blunt end portion 817. FIG. 77A and FIG. 77B depict two partial cross sectioned views of needle assembly 741. As shown, blunt end portion 817 of needle tip 802 is positioned within the lumen of needle body 800 such that tip tabs 804a and 804b are adjacent tip groove portion 814. As shown, cap plug portion 816, plugs one end of needle body 800. Tip tabs 804a and 804b are plastically deformed towards the lumen of needle body 800 to engage tab groove portion 814 thereby providing a mechanical interlock securing needle tip 802 to needle body 800. Suture 748 has an end portion 818 that is positioned within needle body 800 through suture hole 809 adjacent blunt end portion 817. Suture tabs 806a and 806b are plastically deformed inwardly towards the lumen of needle body 800 to secure suture end 818 within the lumen of needle body 800. Needle holder arm tabs 808a and 808b are also plastically deformed towards the lumen of needle body 800. To aid in piercing tissue, sharp end 810 of needle tip 802 has a first taper region 820 and a second taper region 822.

Figure 78:
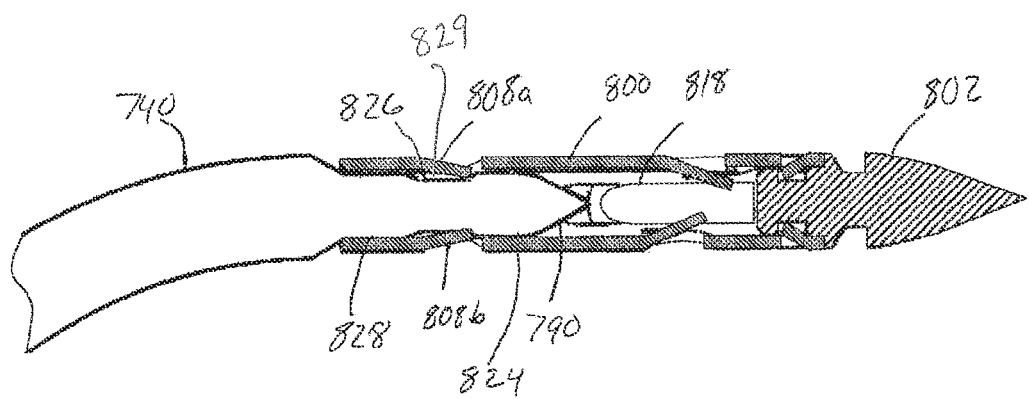
FIG. 78 is a partial section view of a needle assembly engaged with a needle holder arm for use with an endoscopic suturing device according to an embodiment of the present invention.

FIG. 78 illustrates a partial cross sectioned view of tip portion 790 of needle holder arm 740 engaged with needle assembly 741. Tip portion 790 having a first, a second and a third portion 824, 826 and 828 respectively, is positioned within the open end of needle body 800. As shown, the diameter of first and third portions 824, 826 are slightly smaller than the inner diameter of needle body 800 while the diameter second portion 826 appreciably smaller to define a circumferential groove 829 between the first and third portions 824, 828. Needle holder arm tabs 808a and 808b flex as first portion 824 enters the lumen of needle body 800 and elastically recover to engage second portion 826 of needle holder arm 740. To remove needle body 800 from tip portion 790 a noticeable force is required to cause the flexure of tabs 808a and 808b ensuring that needle body 800 does not inadvertently disengage from needle holder arm 740. The force to remove the needle body 800 from the tip portion 790 is applied in a direction away from the tip portion and coaxial with the axis of the tip portion. Alternatively, other means for attaching the needle body to the needle holder arm can be provided. For example, the needle body may be provided with a plurality of arms into which the needle holder arm is received.

Figure 79:
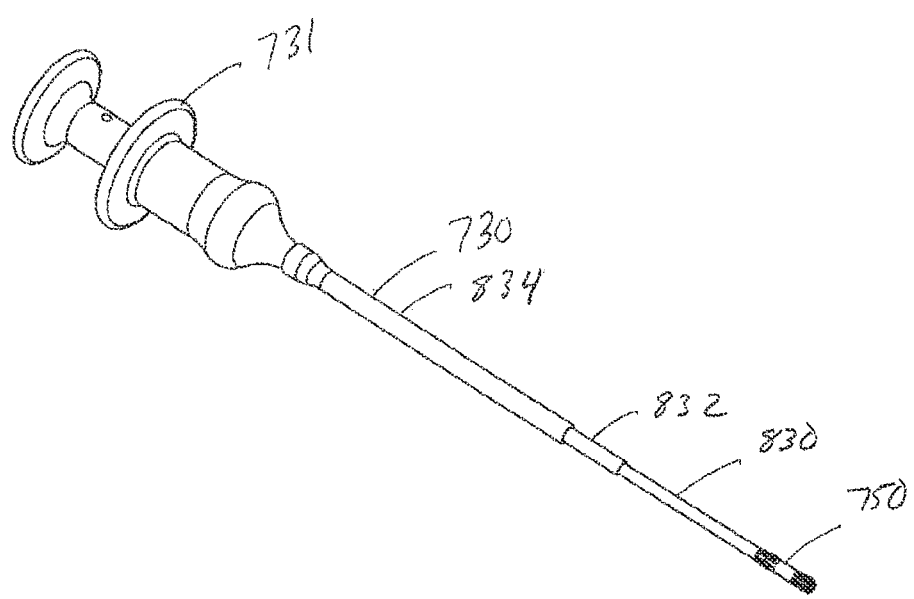
FIG. 79 is an illustrative view of a needle capture device for use with an endoscopic suturing device according to another embodiment of the present invention.
Figure 80:
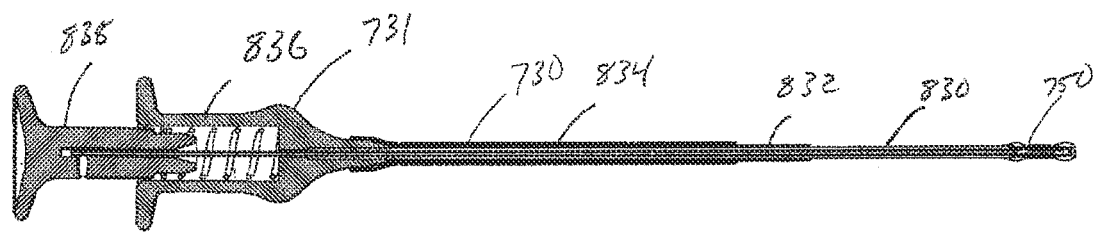
FIG. 80 is a section view of a needle capture device in FIG. 79 for use with an endoscopic suturing device according to another embodiment of the present invention.
Figure 81:
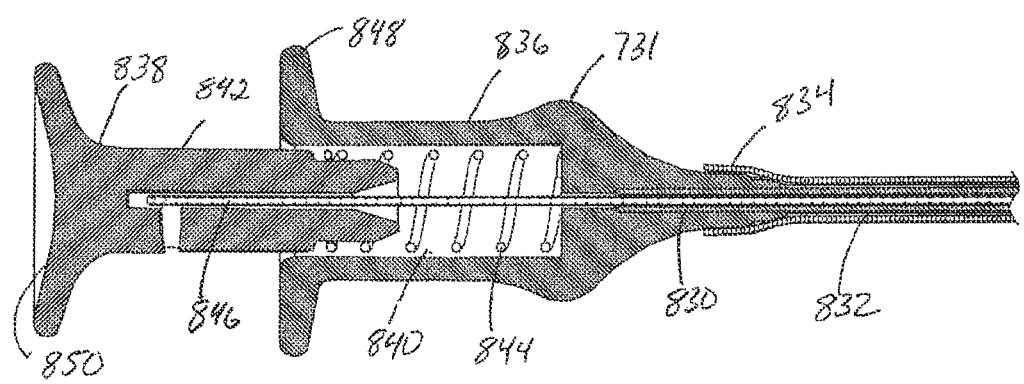
FIG. 81 is an enlarged partial section view of a proximal end of a needle capture device for use with an endoscopic suturing device according to another embodiment of the present invention.
Figure 82:
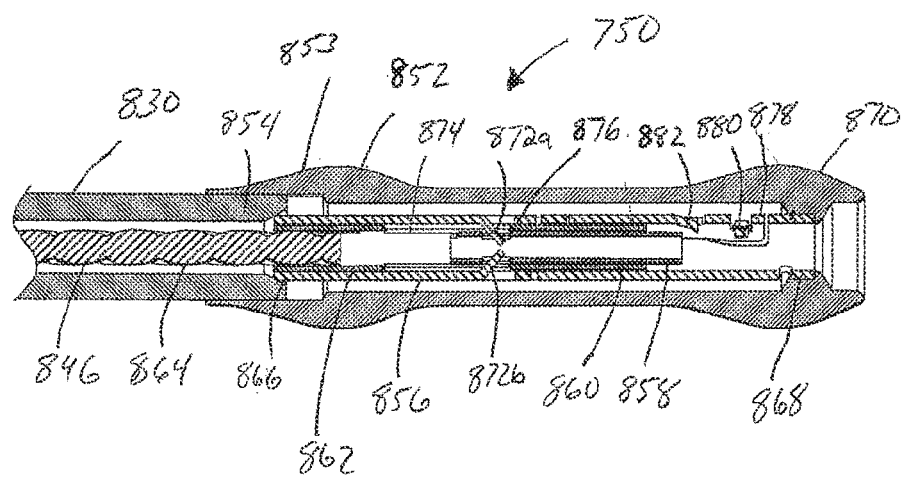
FIG. 82 is an enlarged partial section view of a distal end of a needle capture device for use with an endoscopic suturing device according to another embodiment of the present invention.

FIG. 79 depicts needle capture device 730 having an elongate primary catheter 830 that extends from distal end 750 to proximal handle 731. Also extending from the proximal handle 731 are stiffener sheaths 832 and 834. Primary catheter 830 may be formed as a coil catheter providing flexibility and some resistance to compression. FIG. 80 through FIG. 82. illustrate cross section views of needle capture device 730. FIG. 81 shows an enlarged cross section of handle 731. Handle 731 includes a main body 836 and a button member 838. Main body 836 has a cavity 840 that is dimensioned to receive shaft portion 842 of button member 838. A spring member 844 is positioned within cavity 840 and couples to button member 838. An elongate cable 846 is coupled to shaft 842 and extends through main body 836 coupled to primary catheter 830 to distal end 750. Main body 836 includes a flange portion 848, while button member 838 includes a primary contact point 850. Flange portion 848 is adapted to hold main body 836 by two fingers while primary contact point 850 is adapted to engage a thumb to depress button member 838. The distal end 750 of needle capture device 730 includes a capture housing 852 having a proximal end 853 that is coupled to the distal end 854 of primary catheter 830 as illustrated in FIG. 82. The primary catheter 830 and cable 846 are sized in length to locate a distal end of the capture housing 852 at the distal end of the instrument channel without protruding therefrom when the needle capture device 730 is fully inserted into the instrument channel 729 of the endoscope.

Within the capture housing there is an outer rigid hypotube 856, and inner rigid hypotube 858 and an intermediate rigid hypotube 860. Inner hypotube 858 is positioned within the lumen of intermediate hypotube 860 which is positioned within the lumen outer hypotube 856. The intermediate hypotube 860 has a proximal end 862 that is connected to distal end 864 of cable 846. The proximal end 866 of outer hypotube 856 is coupled to distal end 854 of primary catheter 830, while the outer hypotube distal end 868 is coupled to the distal end 870 of capture housing 852. Outer hypotube 856 includes laser cut tab features 872a and 872b cut from the wall. Intermediate hypotube 860 includes elongate laser cut slots 874. Inner hypotube 858 also includes laser cut slots 876. Tab features 872a and 872b are plastically deformed through slots 874 of intermediate hypotube 860 to engage the slots 876 of inner hypotube 858, thereby fixedly securing the position of the inner hypotube 858 relative to the outer hypotube 856 but allowing the intermediate hypotube 860 to slide between them for the length of slots 874. Outer hypotube 856 has additional laser cut features within the wall that include a live hinge tab 878 that includes a latch tab 880, and latch release ramp 882.

Figure 83A:
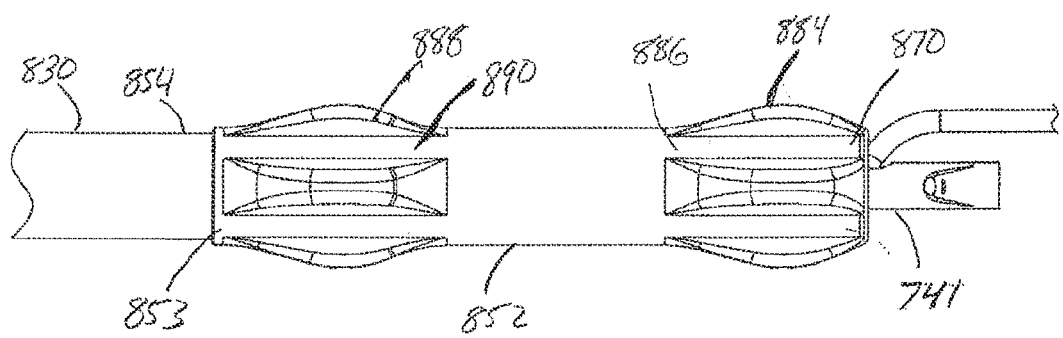
FIG. 83A is an enlarged illustrative view of a distal end of a needle capture device engaged with a needle assembly for use with an endoscopic suturing device according to another embodiment of the present invention.
Figure 83B:
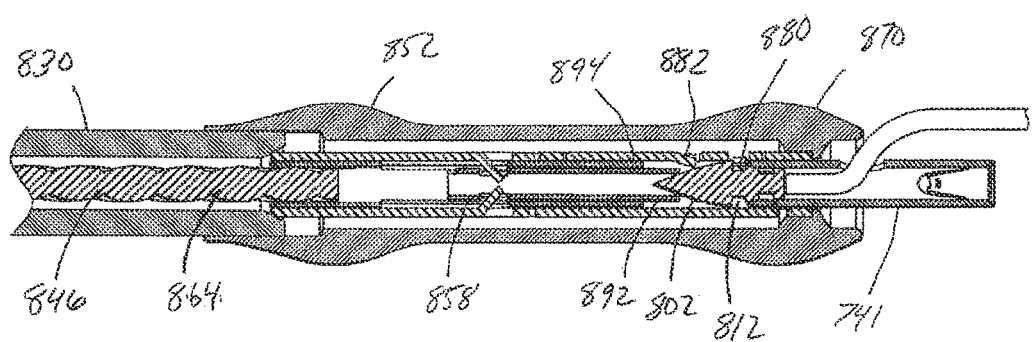
FIG. 83B is an enlarged partial section view of a distal end of a needle capture device engaged with a needle assembly for use with an endoscopic suturing device according to another embodiment of the present invention.

FIG. 83A depicts an enlarged view of the distal end 750 of needle capture device 730 engaged with needle assembly 741. Capture housing 853 includes a plurality of flights 884 separated by space 886 radially arrayed about distal end 870 and a plurality of flights 888 separated by space 890 radially arrayed about proximal end 853. Flights 884 and 888 aid in centering distal end 750 within tissue guard 736 to aid in reliably capturing needle assembly 741 from needle holder arm 740 during suturing. Spaces 886 and 890 between flights allow suture within the instrument channel along side needle capture device 730 to be freely dispensed as needed during suturing. FIG. 83B is a cross section view of capture housing 852 with needle assembly 741 engaged. As needle assembly 741 enters outer hypotube 856, needle tip 802 lifts latch tab 880. When needle tip 802 contacts the distal end 892 of inner hypotube 858, latch tab 880 returns to its normal inward biased position and engages capture groove portion 812 thereby locking needle assembly 741 within capture housing 852. The strength of this capture engagement is substantially higher than the engagement strength of the needle assembly 741 to needle holder arm 740, such that rotation of the needle holder arm 740 relative to the engaged needle capture device 730 or retraction of the engaged needle capture device 730 relative to the needle holder arm 740 in a longitudinal direction coaxial with away from the needle coupling tip portion 790, will exceed the force by which the needle assembly 741 is retained on the needle coupling tip portion 790 causing the needle assembly 741 to disengage from the needle holder arm 740. The distal end 894 of intermediate hypotube 860 is positioned proximal to latch release ramp 882.

Figure 84:
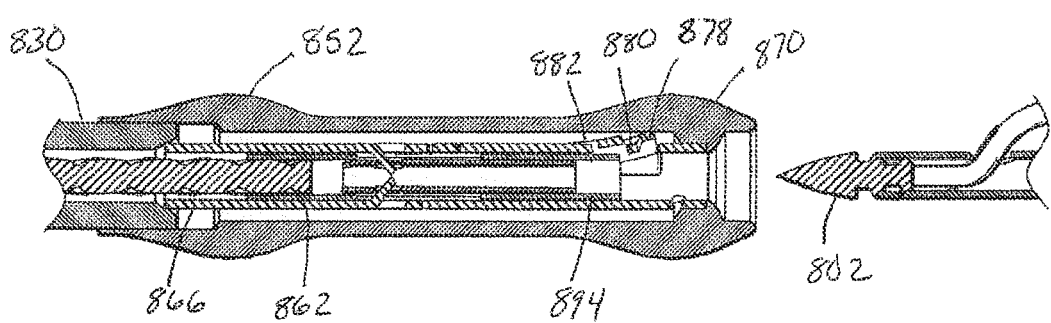
FIG. 84 is an enlarged partial section view of a distal end of a needle capture device disengaged with a needle assembly for use with an endoscopic suturing device according to another embodiment of the present invention.

The ability to controllably release needle assembly 741 is very desirable during an endoscopic suturing procedure. The controlled release allows the physician to reload the needle assembly on the needle holder arm to perform a continuous stitch to release to needle assembly for use as an anchor or t-tag. FIG. 84 illustrates a needle assembly 741 that has been released from needle capture device 730. Upon depression of button member 838, cable 846 is advanced distally causing the proximal end 862 of intermediate hypotube 860 to move distally relative to outer hypotube 856. As the distal end 894 of intermediate hypotube 860 contacts latch release ramp 882 it causes live hinge tab 878 to raise thereby causing latch tab 880 to be removed from latch groove portion 812 of needle tip 802.

Figure 85A:
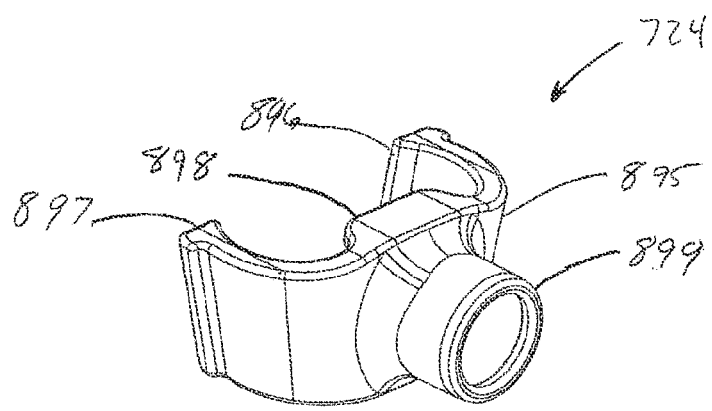
FIG. 85A is an enlarged illustrative view of a handle bracket for use with an endoscopic suturing device according to another embodiment of the present invention.
Figure 85B:
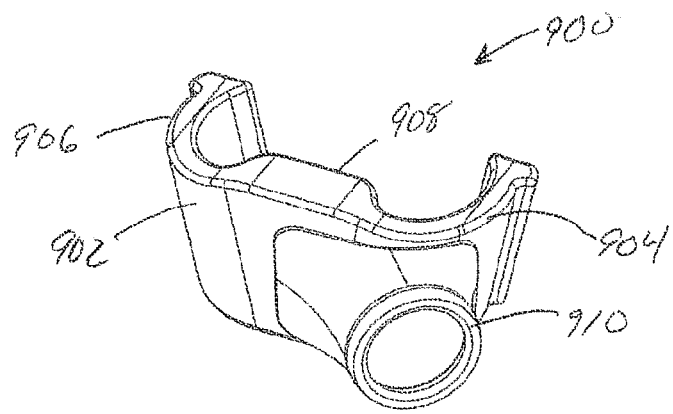
FIG. 85B is an enlarged illustrative view of an alternative handle bracket for use with an endoscopic suturing device according to another embodiment of the present invention.

FIG. 85A depicts an embodiments of a handle bracket 724 that includes a molded body portion 895 having sides 896 and 897. A molded flange 898 extends around the upper portion of body portion 895 and sides 896 and 897. A molded socket portion 899 is positioned at a centered location for coupling with operable handle 722. FIG. 85B illustrates an alternate handle bracket 900 having a molded body portion 902 with sides 904 and 906 and a flange 908 extending around the upper portion of body portion 902 and sides 904 and 906. A molded socket portion 910 is positioned at an off center location adjacent to side 904 for coupling with operable handle 722.

Figure 86:
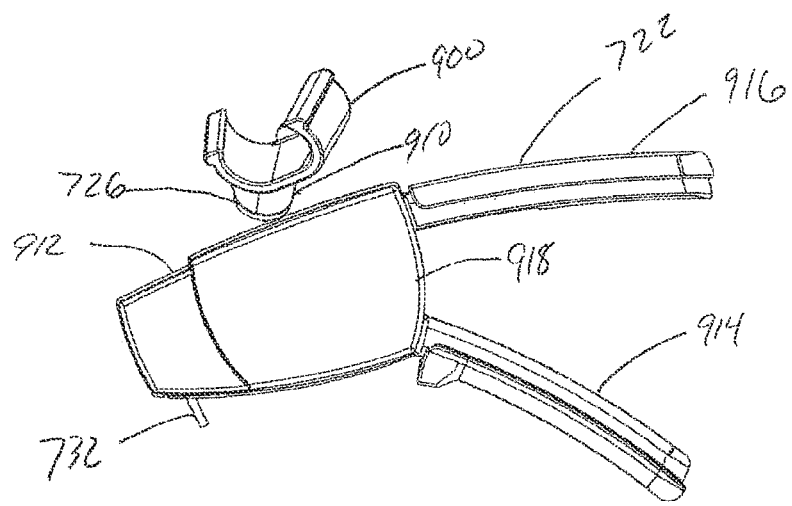
FIG. 86 is an illustrative view of a handle assembly for use with an endoscopic suturing device according to another embodiment of the present invention.
Figure 87A:
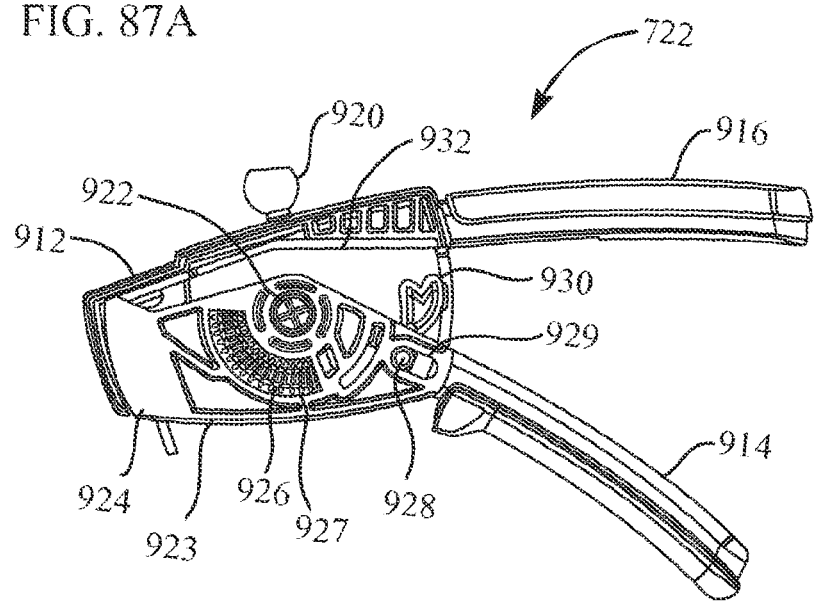
FIG. 87A is an illustrative internal view of a handle assembly in an opened position for use with an endoscopic suturing device according to another embodiment of the present invention.
Figure 87B:
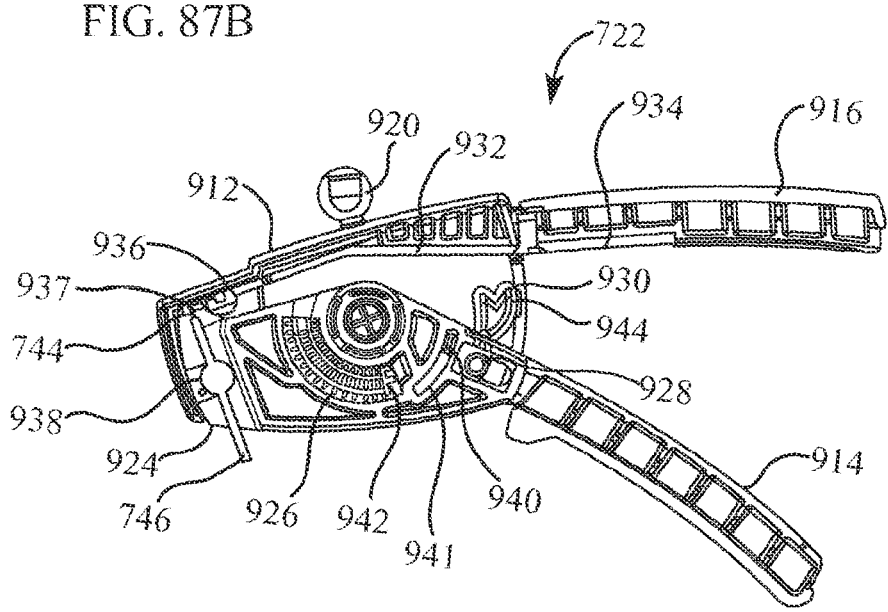
FIG. 87B is a partial section view of a handle assembly in FIG. 87A.
Figure 88A:
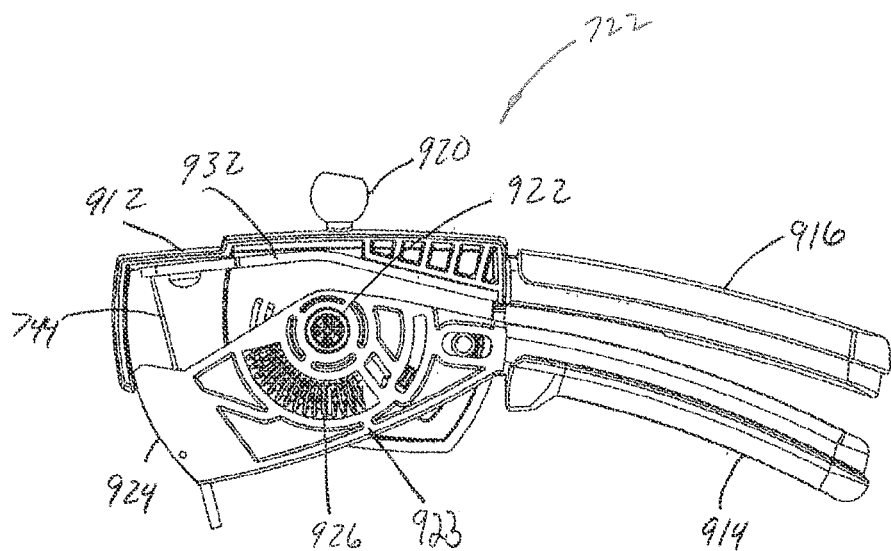
FIG. 88A is an illustrative internal view of a handle assembly in a closed position for use with an endoscopic suturing device according to another embodiment of the present invention.
Figure 88B:
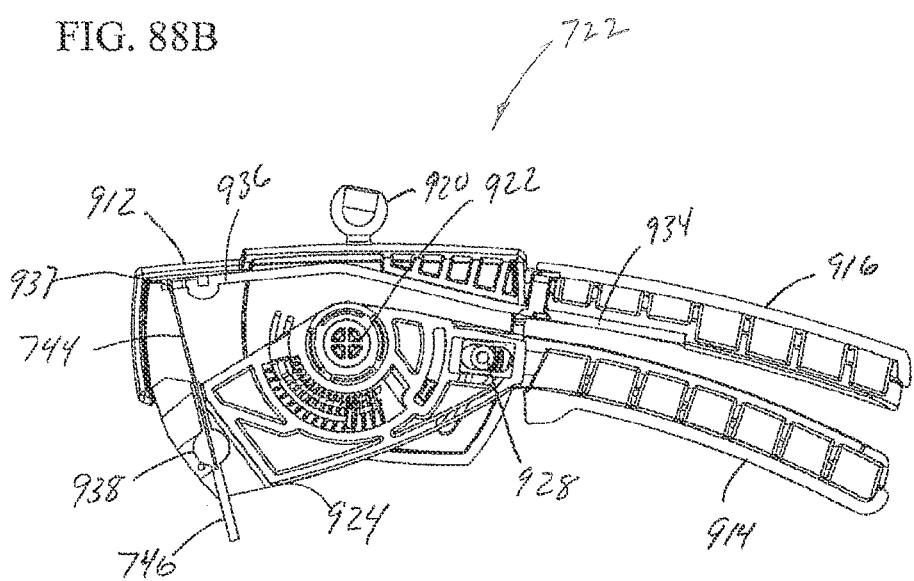
FIG. 88B is a partial section view of a handle assembly in FIG. 88A.

FIG. 86 illustrates a back view of operable handle 722 coupled to handle bracket 900 having a movable joint 726. Handle 722 includes a molded main body 912 having a first handle arm 914, a second handle arm 916 and a cover member 918. FIG. 87A shows handle 722 without cover member 918 and handle bracket 900 revealing the inner assembly of main body 912 and affixed ball member 920. Spindle member 922 is centrally positioned within main body 912. First handle arm 914 is integrally formed with plate 923 and transmission member housing 924 and rotatably positioned on spindle member 922. Spring member 926 is shown protruding through spring slot 927 in plate 923. Indexer member 928 is shown protruding through indexer slot 929 of plate 923. Movement of indexer member 928 is restricted to positions defined by indexer path 930 which takes the form of a molded guide path in main body 912. FIG. 87B shows a partial section view of handle 722 revealing the inner portion of transmission member housing 924. Leaf spring member 932 has a second arm end 934 positioned adjacent second arm handle 916 and a transmission member end 936 positioned adjacent to transmission member 744. Transmission member 744 is fixedly coupled to leaf spring 932 at joint 937. Retaining member 938 is coupled to transmission catheter 746 and positioned within transmission member housing 924 of plate 923. To ensure that plate 923 rotates about spindle 922 appropriately, guide member 940 positioned on main body 912 extends through arcuate guide slot 941 of plate 923. Also positioned on main body 912 is spring stop member 942 that maintains the position of one end of spring member 926. Indexer path 930 includes lock position 944 in which first arm handle 914 may be temporarily locked when closed. FIGS. 88A and 88B show handle 722 in a closed and locked position. First handle arm 914 is shown positioned adjacent second handle arm 916. Transmission member housing 924 is shown rotated about spindle 922 such that transmission catheter 746 is advanced distally relative to transmission member 744 causing needle holder arm 740 of cap assembly 733 to close. (FIG. 74) Spring member 926 is compressed due to the rotation of plate 923 about spindle member 922. Further compression of first handle arm 914 causes indexer member 928 to move from temporary lock position 944 and follow indexer path 930 to a position where the stored energy of compressed spring member 926 is released to cause the rotation of transmission member housing 924 which retracts transmission catheter 746 relative to transmission member 744 to thereby open needle holder arm 740 of cap assembly 733.

Figure 89:
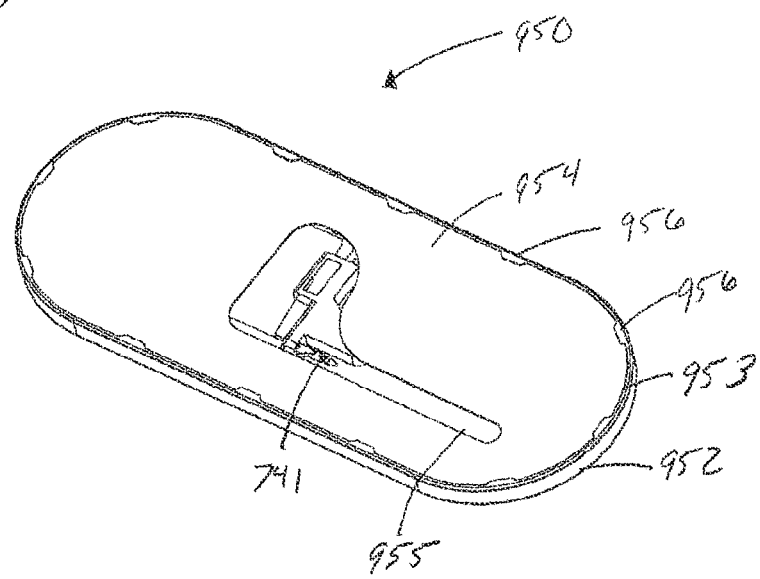
FIG. 89 is a perspective view of a molded suture dispenser including a removable cover.
Figure 90:
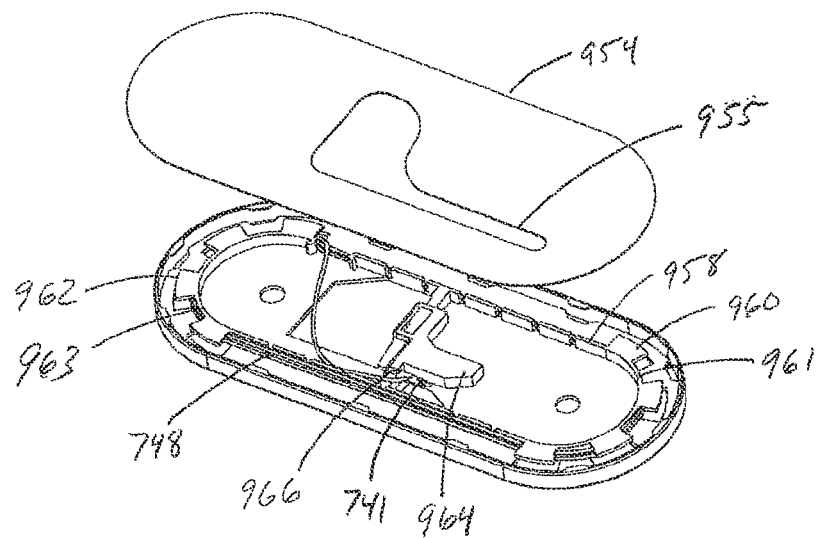
FIG. 90 is an exploded perspective view illustrating the components of the molded suture dispenser.
Figure 91:
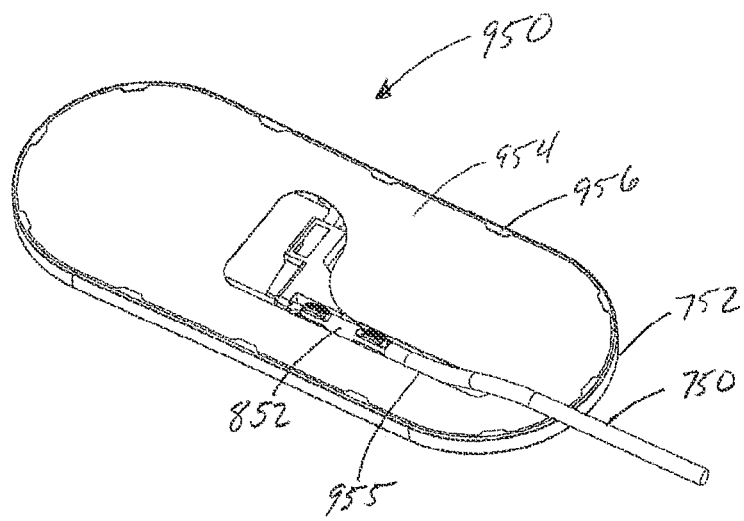
FIG. 91 is a perspective view illustrating the needle capture device engaging the suture dispenser.

FIG. 89 illustrates a suture dispenser 950 that includes a molded base member 952 having a generally oval shape, a raised outer wall 953 and a flexible cover member 954. Cover member 954 has an access aperture 955 to access needle assembly 741. Cover member 954 has a shape and dimensions to be inserted within outer wall 953 and is secured to base member 952 via a plurality of molded tabs 956 attached to outer wall 953 and being projected inwardly in a plane generally parallel to base member 952. FIG. 90 shows an exploded view of suture dispenser 950. Molded base member 952 also includes a raised inner wall 958 having a plurality of molded winding tabs 960 and 962 attached to inner wall 958 curved sections 961 and 963 extending towards the outer wall 953 in a plane generally parallel to base member 952. Molded base member 952 further includes a needle housing support member 964 having a needle holding aperture 966 for holding needle assembly 741. Suture 748 is wound around the inner wall 958 and positioned between winding tabs 960 and 962 and base member 952 with needle assembly 741 being positioned in needle holding aperture 966. FIG. 91 illustrates capture housing 852 of the distal end 750 of needle capture device 730 engaging needle assembly 741 through access aperture 955 of suture dispenser 950.

Figure 92:
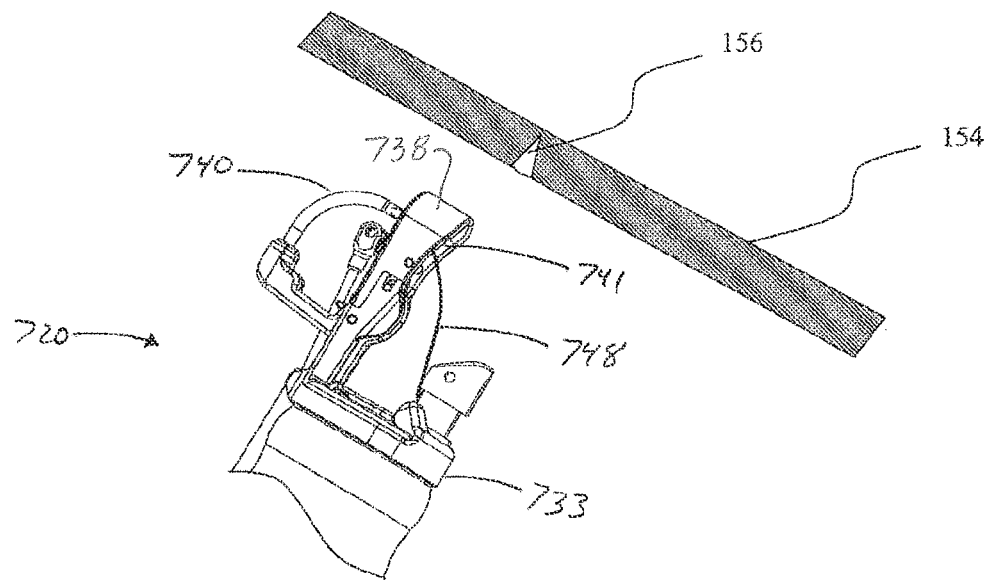
Figure 93:
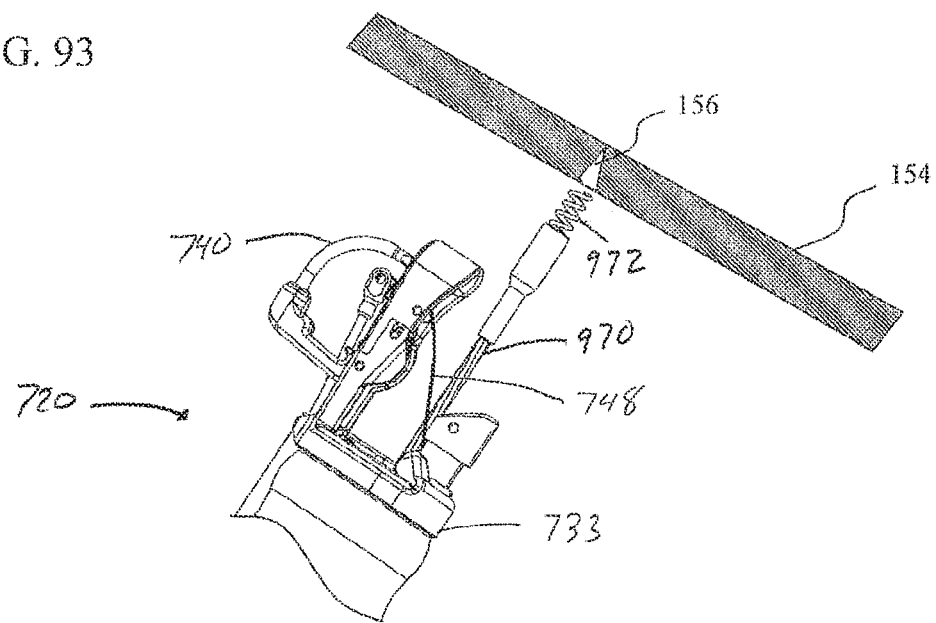
Figure 94:
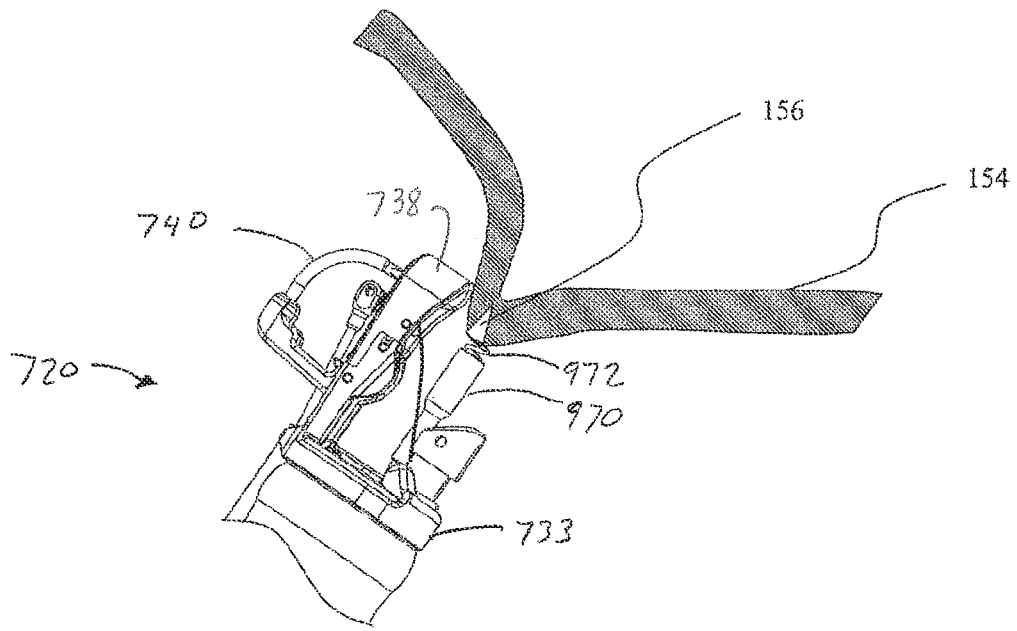
Figure 95:
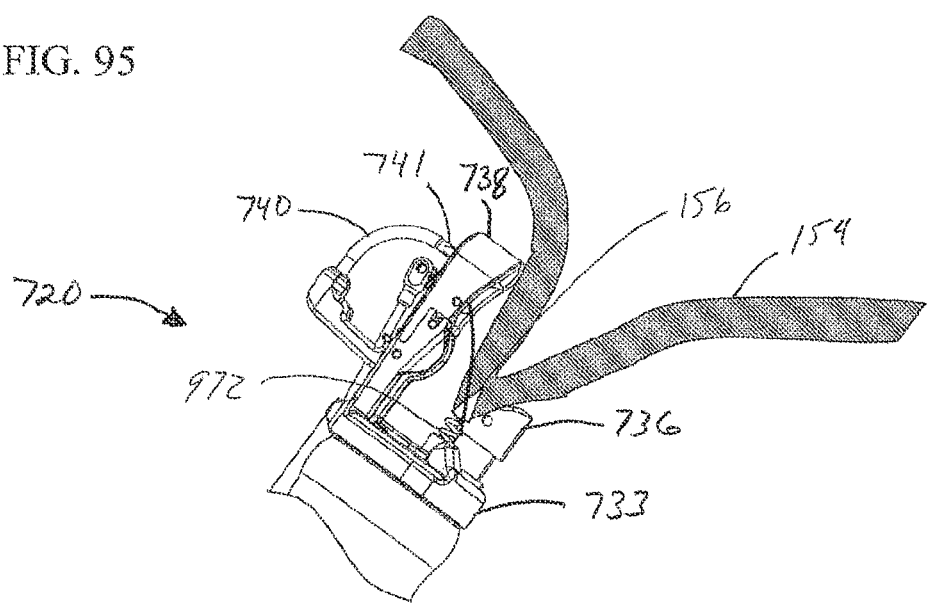
Figure 96:
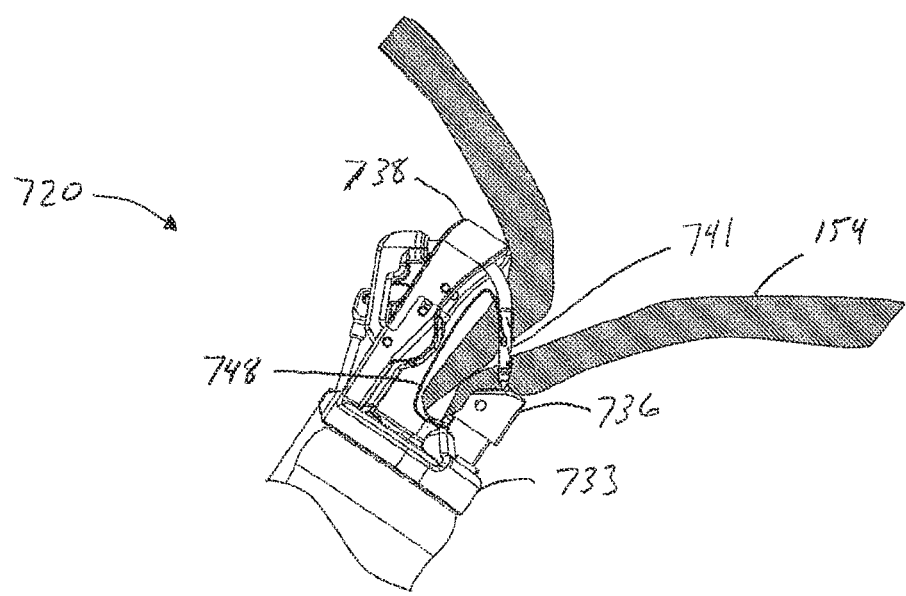
Figure 97:
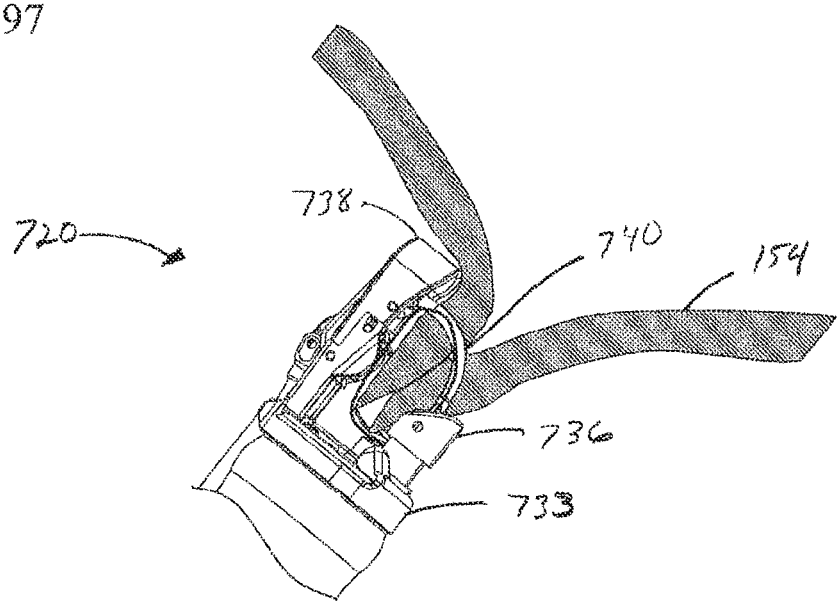
Figure 98:
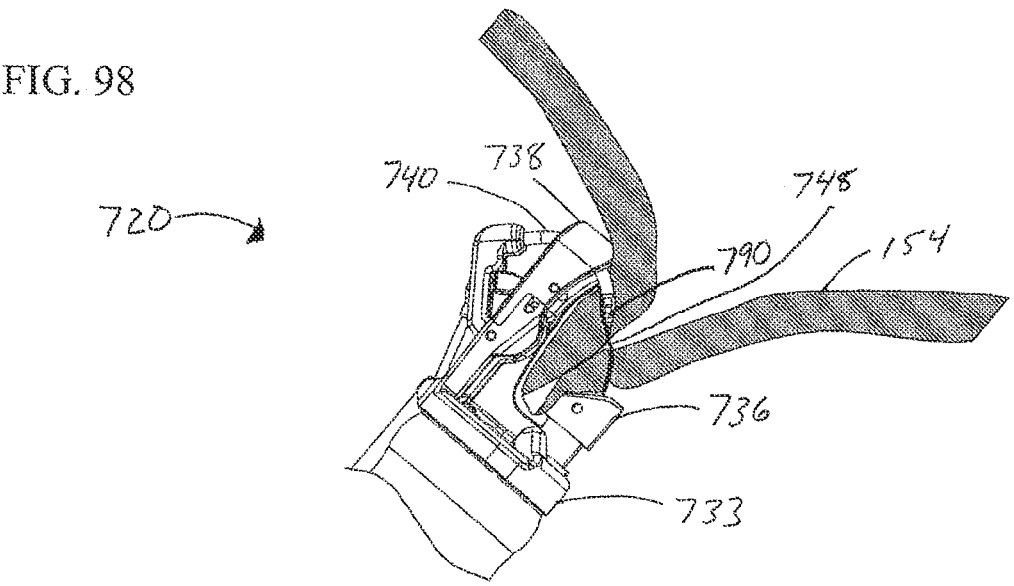
Figure 99:
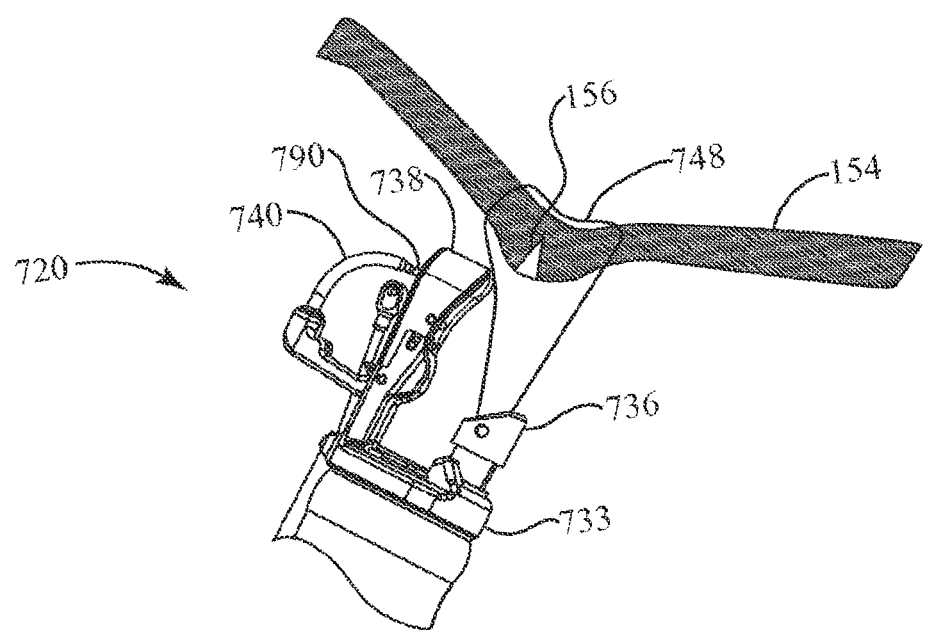

FIG. 92 through FIG. 99 depicts a method of performing a suturing operation using an endoscopic suturing device 720 of the present invention. As shown in FIG. 92, the endoscopic suturing device 720 is positioned adjacent tissue 154 which has a tissue defect 156 to be closed. The endoscopic suturing device 720 is in an open configuration and the tip of needle assembly 741 is shrouded by needle guard 738. FIG. 93 shows the tissue grasper 970 is extended from the endoscope instrument channel such that helical tip 972 is adjacent tissue defect 156. Rotation of the tissue grasper 970 causes the helical tip 972 to securely engage the tissue 154 adjacent to the tissue defect 156. The tissue 154 may be brought closer to the endoscope by slightly retracting the tissue grasper 970 into the instrument channel of the endoscope as shown in FIG. 94. During the retraction of tissue, the needle guard 738 prevents the tissue from dragging against the tip of needle assembly 741, thereby reducing inadvertent tissue damage. The degree of tissue retraction correlates to the size and location of the stitch. For instance to have a larger amount of tissue sutured, the tissue grasper may bring the tissue 154 close to the endoscope as shown in FIG. 95. When attempting to suture a large amount of tissue, the position of the angled distal end of tissue guard 736, in conjunction with the needle guard 738, aids in folding the tissue in preparation for suturing and preferably aids in preventing the tissue from locating immediately adjacent and thereby clogging the needle capture device. The needle holder arm 740 is actuated to move to a closed position causing the needle assembly 741 to pierce tissue 154. The angled portion of tissue guard 736 provides support for the tissue allowing the needle to more easily penetrate the tissue as shown in FIG. 96. The suture 748 is pulled through the tissue as shown in FIG. 97. The control over the amount of tissue retracted allows the physician the ability to perform a partial thickness stitch within the wall of a tissue or a full thickness stitch which extends through a wall of tissue. The needle capture device captures the needle assembly 741 and removes it from the needle holder arm 740(not shown). FIG. 98 shows the needle holder arm partially retracted from the tissue illustrating needle holder arm tip 790 contacting tissue. FIG. 99 shows the needle holder arm 740 moved to an open configuration and removed from tissue 154. Suture 748 remains through the tissue. To continue a running stitch, the needle holder arm can be reloaded with the needle assembly without needing to remove the endoscopic suturing device from the body as previously described. If only one stitch is required the suture may be tied into a surgical knot or a cinch device used to secure the suture, thereby closing the tissue defect.

Figure 100:
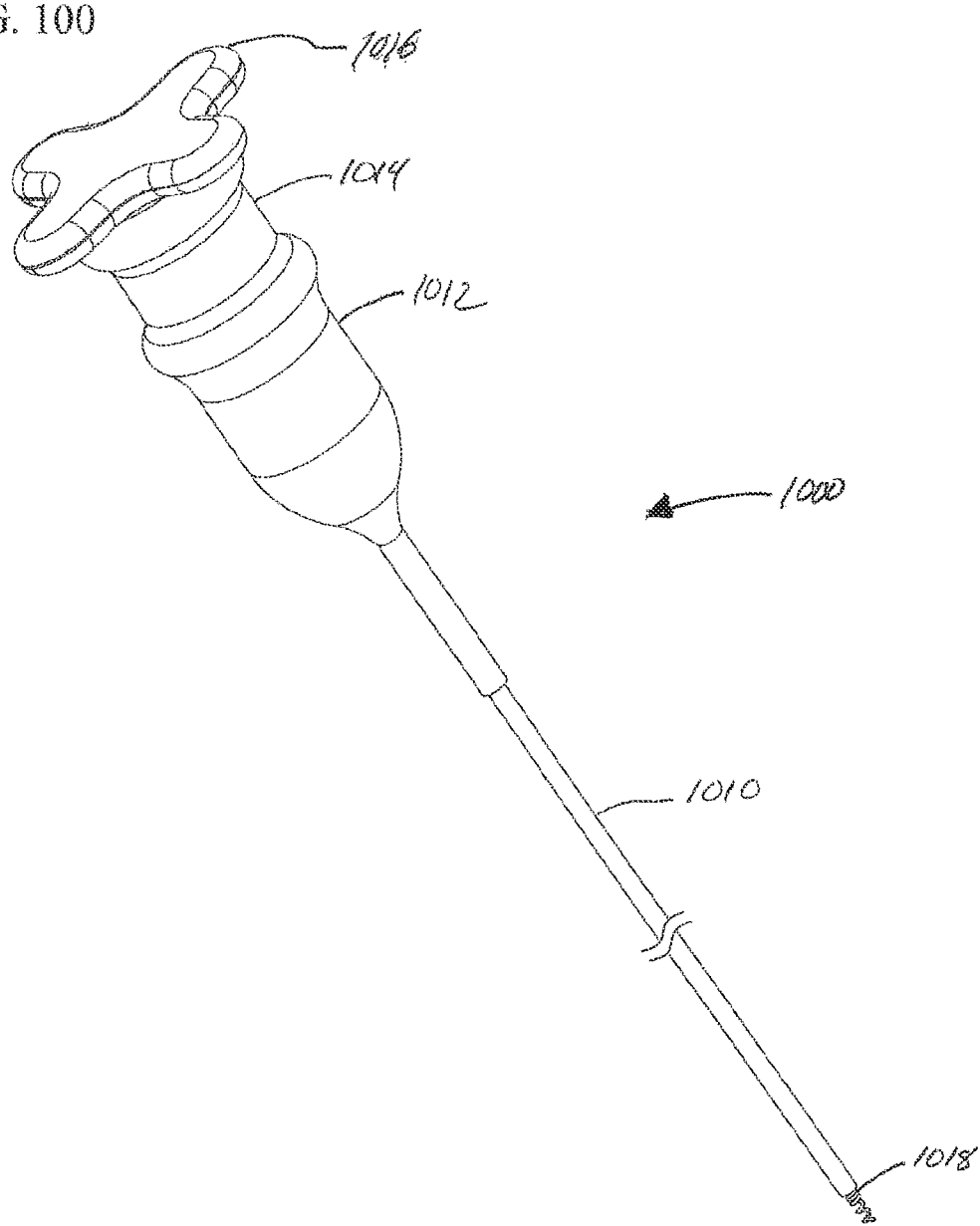
FIG. 100 is a view of a helical tissue grasper according to another embodiment.
Figure 101A:
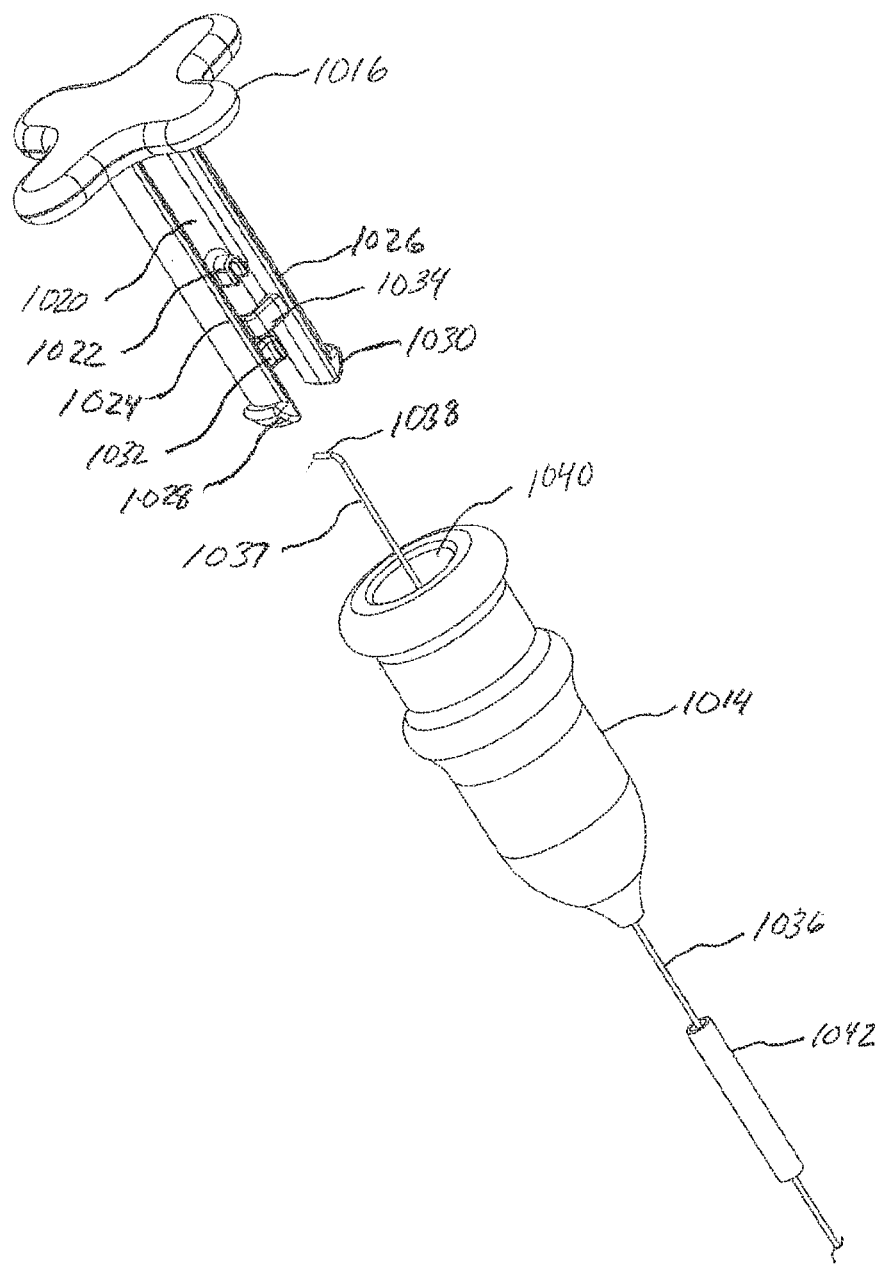
FIGS. 101A and 101B are exploded views of a helical tissue grasper.
Figure 101B:
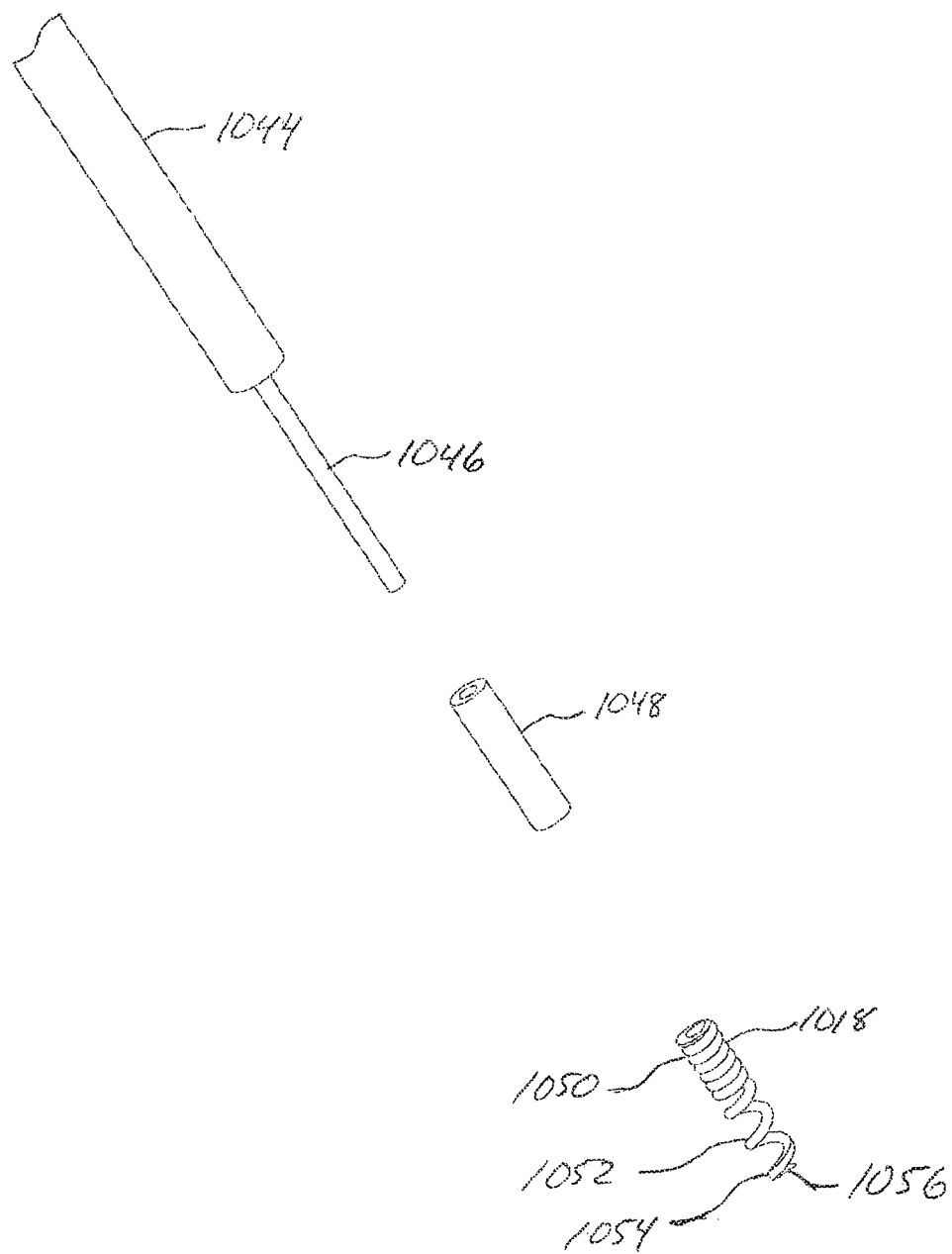

FIG. 100 illustrates tissue grasping instrument according to another embodiment of the present invention. Helical tissue grasper 1000 is shown having an elongate catheter 1010 with a handle 1012 positioned at its proximal end. Handle 1012 has a main body 1014 coupled to catheter 1010 and rotatable knob 1016 for rotating helix member 1018 positioned at the distal end of catheter 1010. FIG. 101A shows exploded view of the proximal portion of helical tissue grasper 1000. Rotatable knob 1016 includes an elongate shaft 1020, a mounting portion 1022 positioned between extension arms 1024 and 1026 that extend from shaft 1020. Positioned at the ends of extension arms 1024 and 1026 are engagement tabs 1028 and 1030 respectively. Proximal to engagement tabs 1028 and 1030 also positioned on extension arms 1024 and 1026 are guide members 1032 and 1034 respectively. Rotatable knob 1016 is preferably formed as a molded plastic part with shaft 1020, mounting portion 1022, extension arms 1024 and 1026, engagement tabs 1028 and 1030, guide members 1032 and 1034 all being integrally formed. Guide members 1032 and 1034 are spaced apart and extend from their respective extension arm towards the other extension arm. Actuation member 1036 having proximal end 1037 and angled proximal tip 1038 is shown extending through receiving cavity 1040 of main body 1014 and strain relief member 1042. FIG. 101B shows an exploded view of the distal portion of helical tissue grasper 1000. Shown extending from Distal end 1044 of catheter 1010 is distal end 1046 of actuation member 1036. Actuation member 1036 preferably takes the form of an elongate flexible resilient wire, however, other forms such flexible torque transmitting multi-filament cables, laser cut hypotubes or catheters may also be suitable. Also shown are bearing sleeve 1048 and helix member 1018 having proximal portion 1050, intermediate portion 1052, distal portion 1054 and distal tip 1056. Helix member 1018 preferably takes the form of a coil formed of round wire having a closed pitch at proximal portion 1050 and an expanded pitch at intermediate and distal portions 1052 and 1054. Distal portion 1054 of helix member 1018 is preferably flattened towards sharpened distal tip 1056.

Figure 102A:
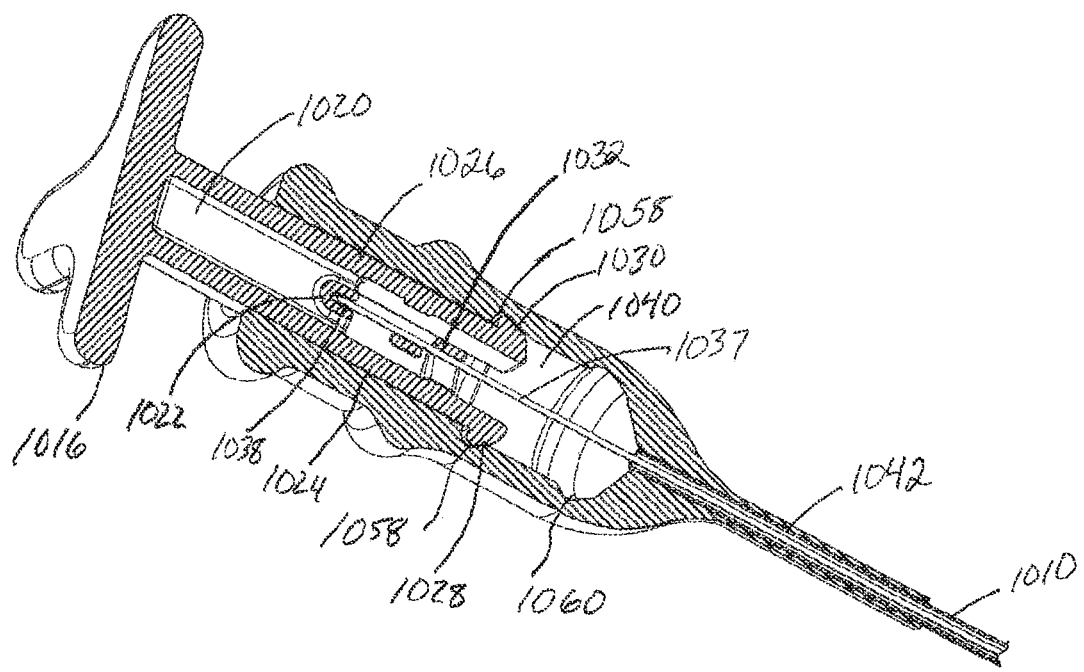
FIGS. 102A and 102B are cross sectional views of the proximal and distal portions of a helical tissue grasper in a first position.
Figure 102B:
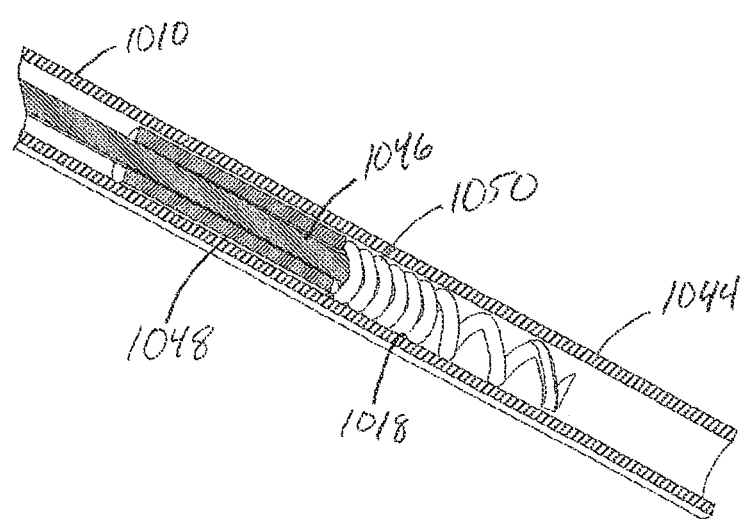
Figure 103A:
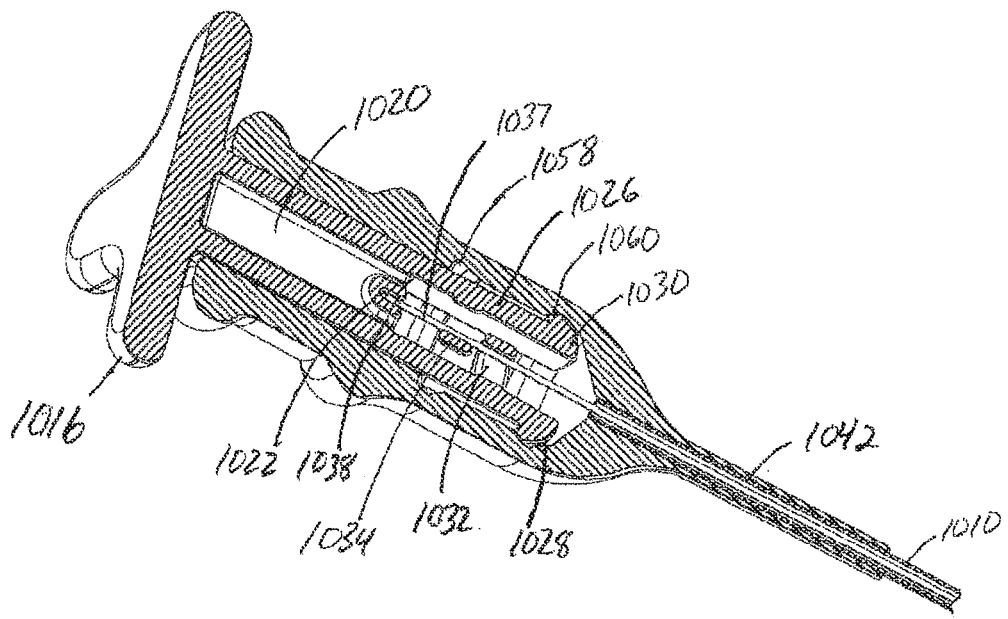
Figure 103B:
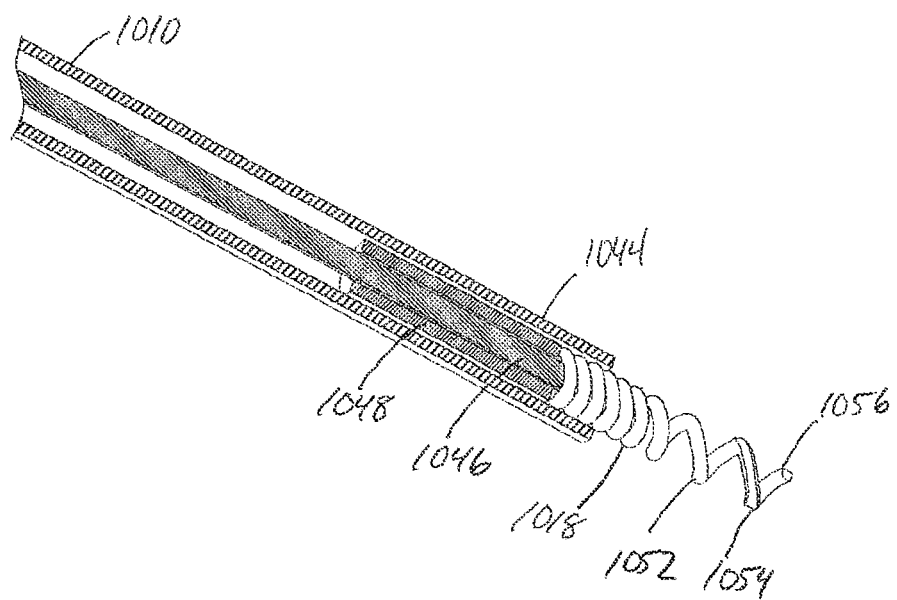

FIGS. 102A and 102B illustrate partial sectioned views of proximal and distal portions of assembled helical tissue grasper 1000 where helix member 1018 is in a delivery configuration. Rotatable knob 1016 is shown coupled to main body 1014 such that shaft 1022 is inserted into receiving cavity 1040. Engagement tabs 1028 and 1030 of extension arms 1024 and 1026 interlockingly engage circular first groove 1058 of main body 1014. Positioned distal to circular first groove 1058 in cavity 1040 is circular second groove 1060. Proximal tip 1038 of actuation member 1036 is coupled to mounting portion 1022 of shaft 1020 thereby restricting longitudinal movement of actuation member 1036 relative to rotatable knob 1016. Guide members 1032 and 1034 are positioned about proximal end 1037 of actuation member 1036 to restrict lateral movement of proximal end 1037 relative to rotatable knob 1016. Actuation member 1036 extends through the proximal end of catheter 1010 and strain relief 1042 which are coupled to the distal end of main body 1014 to catheter distal end 1044. Distal end 1046 of actuation member 1036 is positioned through the lumen of bearing sleeve 1048 adjacent proximal portion 1050 of helix member 1018. Actuation member distal end 1046 is preferably secured to both bearing sleeve 1048 and proximal portion 1050 through laser welding. Additionally, proximal portion 1050 of helix member 1018 may be joined directly to bearing sleeve 1048. As depicted in FIGS. 102A and 102B when engagement tams 1028 and 1030 are interlockingly positioned within circular first groove 1058, helix member 1018 is fully positioned within the lumen of catheter 1010 at distal end 1044 providing a delivery configuration for helical tissue grasper 1000. In the delivery configuration, sharpened distal tip 1056 is shielded by catheter 1010 preventing potential damage to the instrument channel during insertion through the endoscope. FIGS. 103A and 103B illustrate partial sectioned views of proximal and distal portions of assembled helical tissue grasper 1000 where helix member 1018 in a deployed configuration. Rotatable knob 1016 is advanced distally relative to main body 1014 such that engagement tabs 1028 and 1030 disengage from circular first groove 1058 and interlockingly engage circular second groove 1060. Distal movement of rotatable knob 1016 relative to main body 1014 causes actuation member 1036 and helix member 1018 to move distal relative to catheter 1010 such that the intermediate and distal portions 1052 and 1054 and sharpened distal tip 1056 extend distal to catheter distal end 1044 providing a deployed configuration. While in the delivery or deployed configurations rotation of rotatable knob causes the rotation of helix member 1018 through the rotation of actuation member 1036. In the deployed configuration sharpened distal tip 1056 is exposed and free to engage tissue.

Figure 104A:
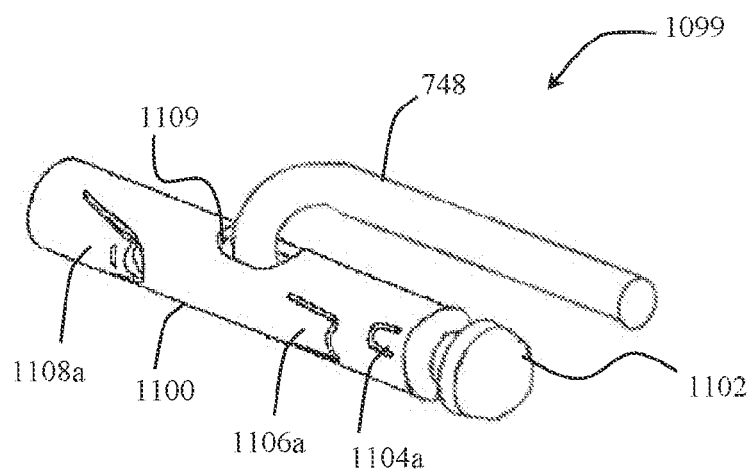
Figure 104B:
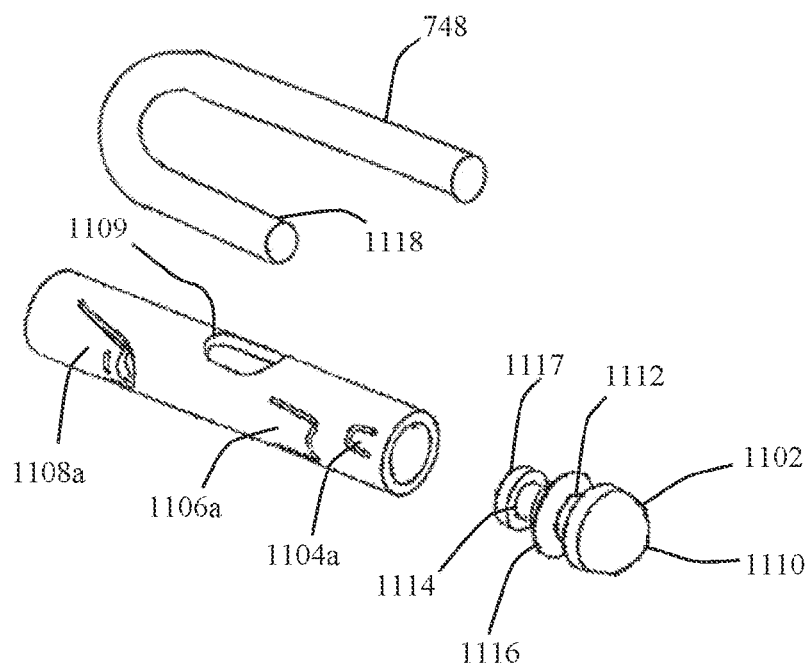
Figure 105A:
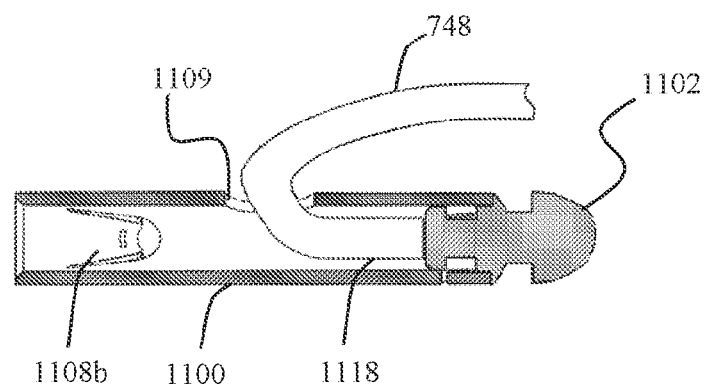
Figure 105B:
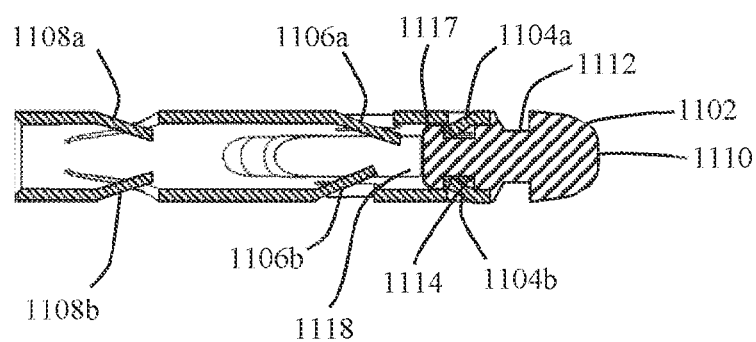

FIG. 104A illustrates anchor assembly 1099 which comprises a preferably straight, hollow anchor body 1100, a blunt anchor tip 1102 and suture 748. Anchor body 1100 is preferably formed from a hypotube of suitable biocompatible material. Anchor body 1100 is preferably processed, by laser cutting, to form various features in the wall of the tube along the length of the tube such as tip tabs 1104a and 1104b located at one end of the tube, suture tabs 1106a and 1106b, needle arm tabs 1108a and 1108b at the other end of the tube, as well as, suture hole 1109 positioned generally in the middle of the tube. FIG. 104B shows an exploded view of anchor assembly 1099 to provide further component detail. Anchor tip 1102 has a blunt end 1110, a capture groove portion 1112, a tab groove portion 1114, a cap plug portion 1116 positioned between the grooves and a blunt end portion 1117. FIG. 105A and FIG. 105B depict two partial cross sectioned views of anchor assembly 1099. As shown, blunt end portion 1117 of anchor tip 1102 is positioned within the lumen of needle body 1100 such that tip tabs 1104a and 1104b are adjacent tip groove portion 1114. As shown, cap plug portion 1116, plugs one end of anchor body 1100. Tip tabs 1104a and 1104b are plastically deformed towards the lumen of anchor body 1100 to engage tab groove portion 1114 thereby providing a mechanical interlock securing anchor tip 1102 to anchor body 1100. Suture 748 has an end portion 1118 that is positioned within anchor body 1100 through suture hole 1109 adjacent blunt end portion 1117. Suture tabs 1106a and 1106b are plastically deformed inwardly towards the lumen of anchor body 1100 to secure suture end 1118 within the lumen of anchor body 1100. Needle arm tabs 1108a and 1108b are also plastically deformed towards the lumen of anchor body 1100.

Figure 106:
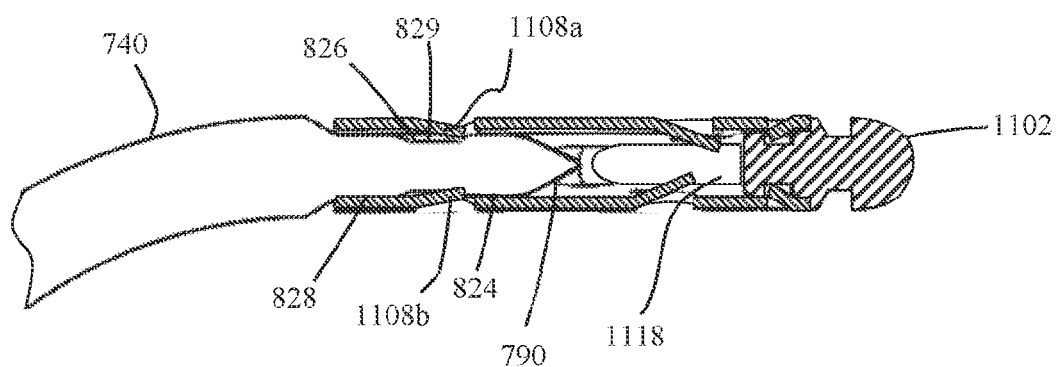

FIG. 106 illustrates a partial cross sectioned view of tip portion 790 of needle holder arm 740 engaged with anchor assembly 1099. Tip portion 790 having a first, a second and a third portion 824, 826 and 828 respectively, is positioned within the open end of anchor body 1100. As shown, the diameter of first and third portions 824, 826 are slightly smaller than the inner diameter of anchor body 1100 while the diameter second portion 826 appreciably smaller to define a circumferential groove 829 between the first and third portions 824, 828. Needle holder tabs 1108a and 1108b flex as first portion 824 enters the lumen of anchor body 1100 and elastically recover to engage second portion 826 of needle holder arm 740. To remove anchor body 1100 from tip portion 790 a noticeable force is required to cause the flexure of tabs 1108a and 1108b ensuring that anchor body 1100 does not inadvertently disengage from needle holder arm 740. The force to remove the anchor body 1100 from the tip portion 790 is applied in a direction away from the tip portion and coaxial with the axis of the tip portion.

Figure 107:
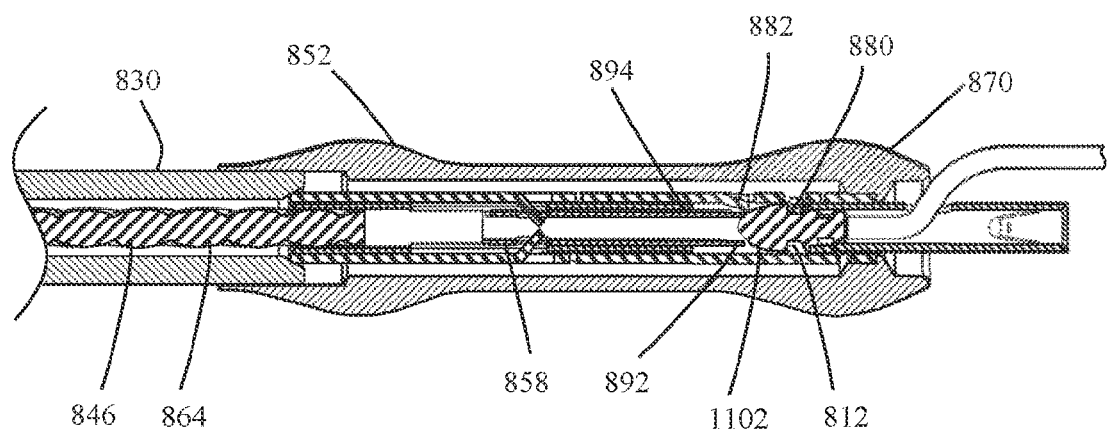

Capture device 730 operates to engage, capture and release anchor assembly 1099 in much the same way as it operates with needle assembly 741. FIG. 107 is a cross section view of capture housing 852 with anchor assembly 1099 engaged. As anchor assembly 1099 enters outer hypotube 856, anchor tip 1102 lifts latch tab 880. When anchor tip 1102 contacts the distal end 892 of inner hypotube 858, latch tab 880 returns to its normal inward biased position and engages capture groove portion 1112 thereby locking anchor assembly 1099 within capture housing 852. The strength of this capture engagement is substantially higher than the engagement strength of the anchor assembly 1099 to needle holder arm 740, such that rotation of the needle holder arm 740 relative to the engaged needle capture device 730 or retraction of the engaged needle capture device 730 relative to the needle holder arm 740 in a longitudinal direction coaxial with away from the needle coupling tip portion 790, will exceed the force by which the anchor assembly 1099 is retained on the needle coupling tip portion 790 causing the anchor assembly 1099 to disengage from the needle holder arm 740. The distal end 894 of intermediate hypotube 860 is positioned proximal to latch release ramp 882.

Figure 108:
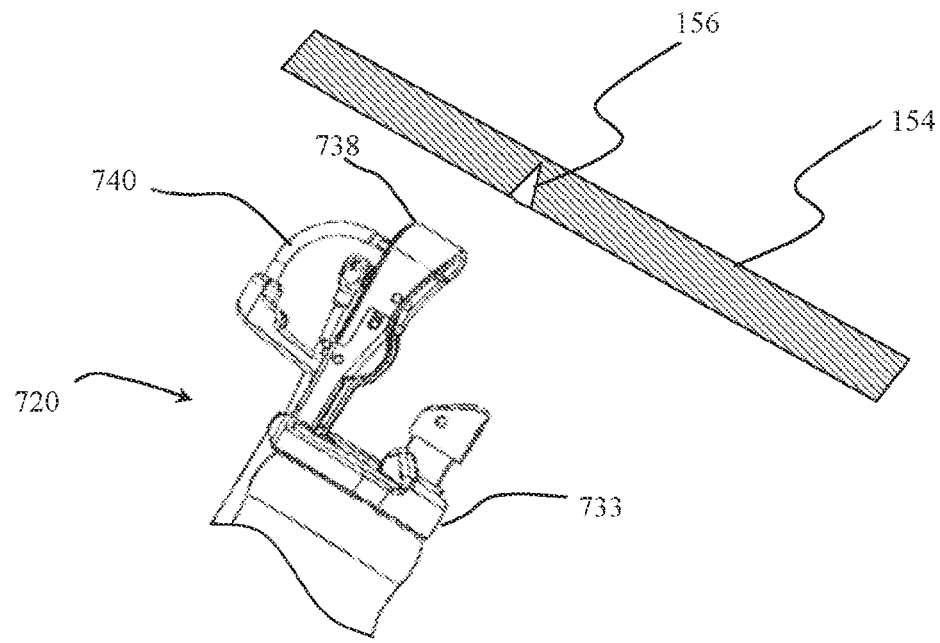
Figure 109:
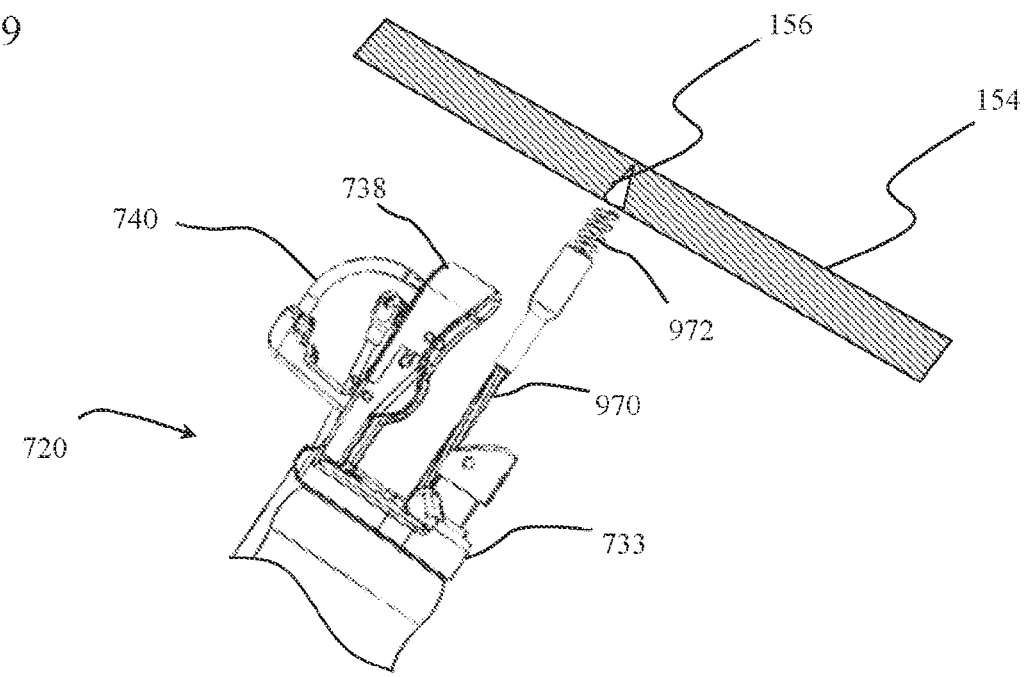
Figure 110:
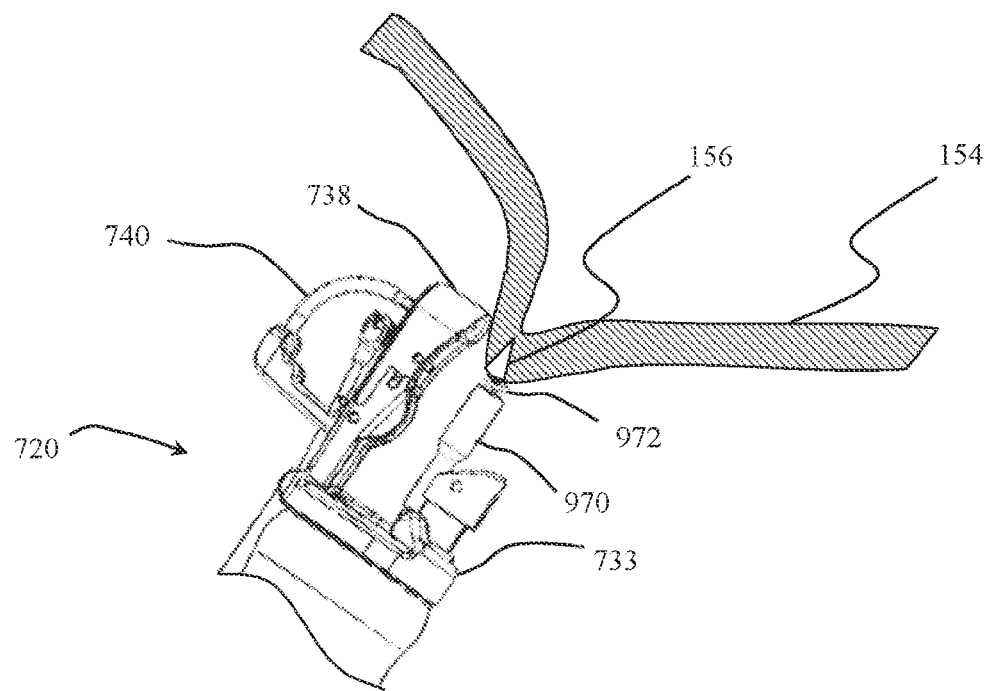
Figure 111:
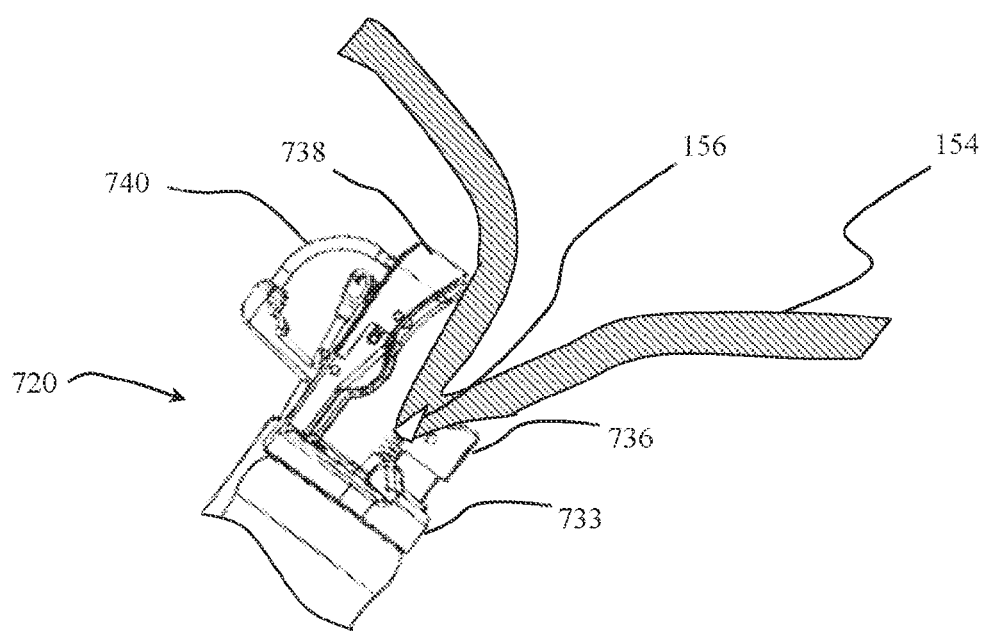
Figure 112:
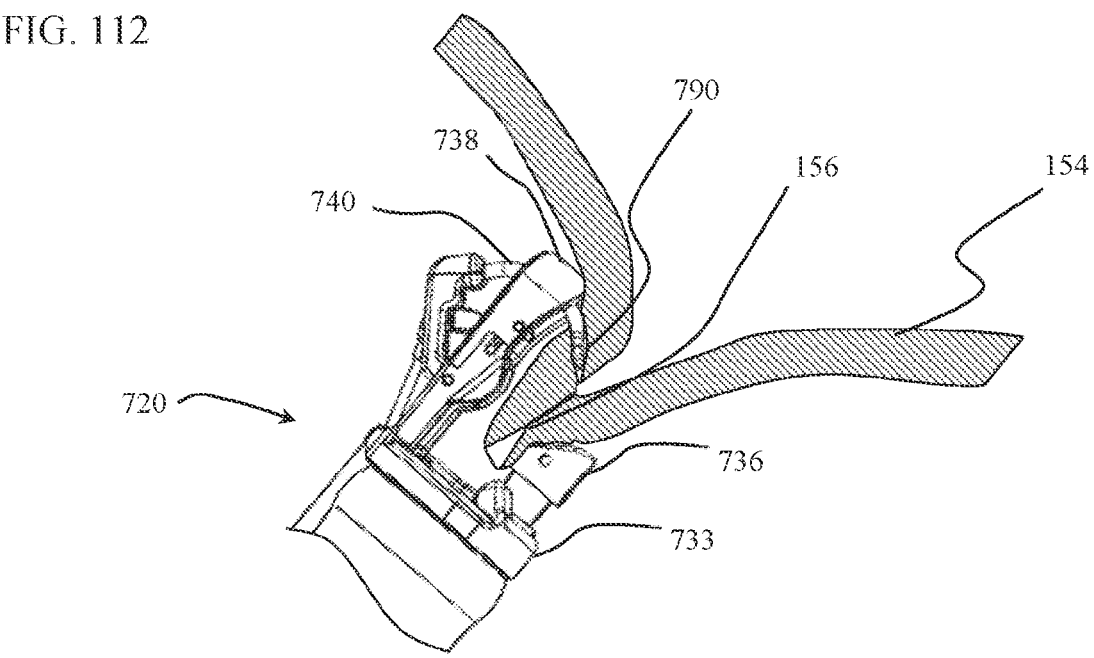

FIG. 108 through FIG. 115 depicts another method of performing a suturing operation using an endoscopic suturing device 720 of the present invention. As shown in FIG. 108, the endoscopic suturing device 720 is positioned adjacent tissue 154 which has a tissue defect 156 to be closed. The endoscopic suturing device 720 is in an open configuration and the tip of needle holder arm 740 is shrouded by needle guard 738. FIG. 109 shows the tissue grasper 970 is extended from the endoscope instrument channel such that helical tip 972 is adjacent tissue defect 156. Rotation of the tissue grasper 970 causes the helical tip 972 to securely engage the tissue 154 adjacent to the tissue defect 156. The tissue 154 may be brought closer to the endoscope by slightly retracting the tissue grasper 970 into the instrument channel of the endoscope as shown in FIG. 110. During the retraction of tissue, the needle guard 738 prevents the tissue from dragging against the sharp tip of needle holder arm 740, thereby reducing inadvertent tissue damage. The degree of tissue retraction correlates to the size and location of the stitch. For instance to have a larger amount of tissue sutured, the tissue grasper may bring the tissue 154 close to the endoscope as shown in FIG. 111. When attempting to suture a large amount of tissue, the position of the angled distal end of tissue guard 736, in conjunction with the needle guard 738, aids in folding the tissue in preparation for suturing and preferably aids in preventing the tissue from locating immediately adjacent and thereby clogging the needle capture device. The needle holder arm 740 is actuated to move to a closed position causing the sharp tip of the needle holder arm 740 to pierce tissue 154. The angled portion of tissue guard 736 provides support for the tissue allowing the needle to more easily penetrate the tissue as shown in FIG. 112. While in the closed position, the tip 790 of needle holder arm 740 is positioned within tissue guard 736 and capture device 730 which is loaded with anchor assembly 1099 is advanced longitudinally within the endoscope channel leading to tissue guard 736 to position anchor assembly 1099 onto tip 790. Anchor assembly 1099 is released from capture device 730 and is retained on needle holder arm 740 as shown in FIG. 113. The needle holder arm 740 is then opened, causing anchor assembly 1099, along with suture 748 to be pulled through the previously pierced tissue as shown in FIG. 114. FIG. 115 shows the needle holder arm 740 moved to an open configuration and removed from tissue 154. Suture 748 remains through the tissue and anchor assembly 1099 is engaged on needle holder arm 740. To continue a running stitch, the capture device is be used to remove the anchor assembly and the needle holder arm can be used to pierce tissue in another location. As previously discussed the anchor assembly can be reloaded onto the needle holder arm without needing to remove the endoscopic suturing device from the body as previously described. If only one stitch is required the suture may be tied into a surgical knot or a cinch device used to secure the suture, thereby closing the tissue defect.

The present invention has been described in conjunction with the preferred embodiments shown in various drawings. Obviously, however, other similar embodiments can be used to realize the same functions as those of the present invention, the above embodiments can be modified, or other embodiments can be added. The present invention is not therefore limited to any single embodiment. For example, each treatment device described above can be used together with a rigid endoscope, trocar, or the like as well as flexible endoscopes. Also, while particular sizes and shapes were described with respect to the end cap, needle guard, tissue guard, etc. of a particular embodiment, other sizes and shapes could be utilized. For purposes of understanding the specification and claims, where the terms "substantially" or "approximately" are used, they should be understood to provide a range of plus or minus 20%, For example, an angle of "approximately 180 degrees" should be understood to include an angle in the range of 144 to 216 degrees. A size of "substantially 2 mm" should be understood to include a size in the range of 1.6 to 2.4 mm. Further, it should be appreciated that different aspects of each embodiment can be used in conjunction with the other embodiment. By way of example only, the handle assemblies for the needle capture device and for the endoscopic suturing device of the various embodiments may be used interchangeably across the various embodiments. It will therefore be appreciated by those skilled in the art that yet other modifications could be made to the provided invention without deviating from its spirit and scope as claimed.

What is claimed is:

1. A method of performing a suturing operation using an endoscopic suturing device provided on a distal end of an endoscope, said method comprising:

positioning the endoscopic suturing device adjacent a first location along a patient's tissue, the suturing device having a needle holder arm with a sharp tip and a needle guard, wherein the suturing device is initially positioned adjacent the first location with the sharp tip of the needle holder arm shrouded by the needle guard and distally spaced from the distal end of the endoscope;

extending the sharp tip of the needle holder arm through tissue at the first location;

extending the sharp tip proximally towards the distal end of the endoscope and into engagement with a first end of an anchor assembly distal to a second end positioned within a needle capture device extending from the endoscope;

releasing the anchor assembly from the needle capture device to retain the anchor assembly on the needle holder arm; and returning the needle holder arm to a position shrouded by the needle guard.

2. The method of claim 1, wherein a suture is coupled to the anchor assembly, said method further comprising pulling the suture with the anchor assembly from the needle capture device through tissue to return the needle holder arm carrying the anchor assembly to the position shrouded by the needle guard.

3. The method of claim 2, further comprising:
moving the endoscopic suturing device to a second location along the patient's tissue spaced apart from the first location; and
moving the needle holder arm to extend the distal end of the anchor assembly, including the suture, through the second location.

4. The method of claim 3, further comprising extending the distal end of the anchor assembly into the needle capture device to remove the anchor assembly from the needle holder arm and to retain the anchor assembly with respect to the needle capture device.

5. The method of claim 4, further comprising tying the suture after a desired number of stitches have been completed.

6. The method of claim 3, wherein the distal end of the anchor assembly is sharp, and extending the distal end of the anchor assembly through the second location comprises piercing tissue with the distal end of the anchor assembly.

7. A method of performing a suturing operation using an endoscopic suturing device provided on a distal end of an endoscope and having a needle holder arm movable from a first position to a second position, said method comprising:
positioning the endoscopic suturing device adjacent a first location along a patient's tissue with the needle holder arm in the first position;
extending the distal end of the needle holder arm through tissue at the first location to move the needle holder arm from the first position to the second position;
extending a distal end of the needle holder arm into engagement with a first end of an anchor assembly having a second end positioned proximal to the first end and within a needle capture device extending from the endoscope; and
returning the needle holder arm to the first position.

8. The method of claim 7, wherein a suture is coupled to the anchor assembly, said method further comprising pulling the suture with the anchor assembly from the needle capture device through tissue to return the needle holder arm carrying the anchor assembly to the first position.

9. The method of claim 8, further comprising:
moving the endoscopic suturing device to a second location along the patient's tissue spaced apart from the first location; and
moving the needle holder arm to extend the distal end of the anchor assembly, including the suture, through the second location.

10. The method of claim 9, further comprising moving the needle holder arm to the second position to extend the distal end of the anchor assembly into the needle capture device to remove the anchor assembly from the needle holder arm and to retain the anchor assembly with respect to the needle capture device.

11. The method of claim 10, further comprising tying the suture after a desired number of stitches have been completed.

12. The method of claim 9, wherein the distal end of the anchor assembly is sharp, and extending the distal end of the anchor assembly through the second location comprises piercing tissue with the distal end of the anchor assembly.

13. The method of claim 7, wherein the anchor assembly is securely held by the needle capture device, said method further comprising releasing the anchor assembly from the needle capture device to be carried by the needle holder arm through tissue.

14. The method of claim 7, wherein the first position of the needle holder arm is a position in which the distal end of the needle holder arm is shrouded from the patient's tissue.

15. The method of claim 7, wherein the second position of the needle holder arm is a position engaging the anchor assembly held by the needle capture device.

16. The method of claim 7, wherein the needle holder arm is closer to the patient's tissue when in the first position than when in the second position.

17. A method of performing a suturing operation using an endoscopic suturing device, said method comprising:
transluminally advancing the endoscopic suturing device operatively associated with a distal end of an endoscope to a first location along a patient's tissue;
advancing a distal end of a needle holder arm of the suturing device from a first position thereof through tissue at the first location;
extending a distal end of the needle holder arm to a second position thereof closer to the endoscope and into engagement with an anchor assembly held by a needle capture device of the endoscopic suturing device;
releasing the anchor assembly from the needle capture device to retain the anchor assembly on the needle holder arm; and
returning the needle holder arm to the first position thereof, distal to the endoscope.

18. The method of claim 17, wherein a suture is coupled to the anchor assembly, said method further comprising pulling the suture with the anchor assembly from the needle capture device through tissue to return the needle holder arm carrying the anchor assembly to the first position.

19. The method of claim 18, further comprising:
moving the endoscopic suturing device to a second location along the patient's tissue spaced apart from the first location; and
moving the needle holder arm to extend the anchor assembly, including the suture, through the second location.

20. The method of claim 19, further comprising capturing the anchor assembly with the needle capture device to remove the anchor assembly from the needle holder arm and to retain the anchor assembly with respect to the needle capture device.

* * * * *